US011752130B2

(12) United States Patent
Hagel et al.

(10) Patent No.: US 11,752,130 B2
(45) Date of Patent: Sep. 12, 2023

(54) CARBOXYLATED PSILOCYBIN DERIVATIVES AND METHODS OF USING

(71) Applicant: Enveric Biosciences Canada Inc., Calgary (CA)

(72) Inventors: Jillian M. Hagel, Calgary (CA); Peter J. Facchini, Calgary (CA); Chang-Chun Ling, Calgary (CA)

(73) Assignee: Enveric Biosciences Canada Inc., Calgary (CA)

( * ) Notice: Subject to any disclaimer, the term of this patent is extended or adjusted under 35 U.S.C. 154(b) by 0 days.

(21) Appl. No.: 17/951,530

(22) Filed: Sep. 23, 2022

(65) Prior Publication Data

US 2023/0044066 A1 Feb. 9, 2023

Related U.S. Application Data

(63) Continuation of application No. PCT/CA2021/051712, filed on Dec. 1, 2021.

(60) Provisional application No. 63/248,037, filed on Sep. 24, 2021, provisional application No. 63/119,786, filed on Dec. 1, 2020.

(51) Int. Cl.
*A61K 31/404* (2006.01)
*A61P 25/18* (2006.01)
*C07D 209/32* (2006.01)
*C07D 209/16* (2006.01)
*C07D 209/30* (2006.01)

(52) U.S. Cl.
CPC ............ *A61K 31/404* (2013.01); *A61P 25/18* (2018.01); *C07D 209/16* (2013.01); *C07D 209/30* (2013.01); *C07D 209/32* (2013.01)

(58) Field of Classification Search
CPC ..... A61K 31/404; A61P 25/18; C07D 209/30; C07D 209/32
See application file for complete search history.

(56) References Cited

FOREIGN PATENT DOCUMENTS

WO WO2007070892 A2 6/2007
WO WO2018148605 A1 8/2018
WO WO2021/155470 A1 8/2021

OTHER PUBLICATIONS

Registry (Registry Databse, RN 2497017-35-1, Entered STN: Oct. 27, 2020).*
Glennon et al. (J. Med. Chem. 1980, 23, 1222-1226).*
Finnin, B. and Morgan, T.M., Transdermal penetration enhancers: applications, limitations, and potential J Pharm Sci. Oct. 1999;88(10):955-8.
Romeo et al. Clinical and biological predictors of psychedelic response in the treatment of psychiatric and addictive disorders: A systematic review. J Psychiatr Res 137: 273-282, 2021.
Daniel, J. et al. Clinical potential of psilocybin as a treatment for mental health conditions. Mental Health Clin/, 2017;7(1): 24-28.
Grob, C. et al. Pilot study of psilocybin treatment for anxiety in patients with advanced-stage cancerArch. Gen. Psychiatry, 2011, 68(1) 71-78.
Cathart-Harris, R.L. et al. Psilocybin with psychological support for treatment-resistant depression: an open-label feasibility study. Lancet Psychiatry, 2016, 3: 619-627.
Inserra et al., Psychedelics in Psychiatry: Neuroplastic. Immunomodulatory, and Neurotransmitter Mechanisms. 2020. Pharmacol Rev 73: 202.
Terrasso et al., Human neuron-astrocyte 3D co-culture-based assay for evaluation of neuroprotective compounds. 2017, J Pharmacol Toxicol Methods 83: 72.
Pyrgiotakis G. et al. Cell death discrimination with Raman spectroscopy and support vector machines. 2009, Ann Biomed. Eng. 37: 1464-1473.
Weaver et al., Test systems in drug discovery for hazard identification and risk assessment of human drug-induced liver injury. 2017, Expert Opin Drug Metab Toxicol 13: 767.
Donato et al., Culture and Functional Characterization of Human Hepatoma HepG2 Cells. 2015, Methods Mol Biol 1250: 77.
Núñez et al., Target-drug interactions: first principles and their application to drug discovery. 2012, Drug Disc Today 17:10.
Maguire et al.,Radioligand binding assays and their analysis. 2012, Methods Mol Biol 897: 31.
Kim K. et al.,Structure of a Hallucinogen-Activated Gq-Coupled 5-HT 2A Serotonin Receptor. 2020, Cell 182:1574-1588.
Wuensch C. et al., Regioselective Enzymatic Carboxylation of Phenols and Hydroxystyrene Derivatives. 2012, Org Lett. 14 (8) 1974-1977.
Lack, A. and Fuchs, G., Carboxylation of phenylphosphate by phenol carboxylase, an enzyme system of anaerobic phenol metabolism. 1992, J. Bacteriol. 174 (11) 3629-3636.
Chang et al., Isolation and Characterization of O-methyltransferases Involved in the Biosynthesis of Glaucine in Glaucium flavum. 2015, Plant Physiol. 169: 1127-1140.
Ross et al., Acute and Sustained Reductions in Loss of Meaning and Suicidal Ideation Following Psilocybin-Assisted Psychotherapy for Psychiatric and Existential Distress in Life-Threatening Cancer. ACS Pharmacol. Transl. Sci. 4: 553-562, 2021.
Palangsuntikul, R. et al. Holographic Quantitative Structure-Activity Relationships of Tryptamine Derivatives at NMDA, 5HT1A and 5HT2A Receptors. Molecules 2013, 18, 8799-8811.
Luo J. and Larrosa I., C-H Carboxylation of Aromatic Compounds through CO2 Fixation. 2017, ChemSusChem, 10, 3317-3332.
Sherwood, A.M. et al. Synthesis and Biological Evaluation of Tryptamines Found in Hallucinogenic Mushrooms: Norbaeocystin, Baeocystin, Norpsilocin, and Aeruginascin. J. Nat. Prod. 2020, 83, 461-46.
Berger, M.L. Screening of 64 Tryptamines at NMDA, 5-HT1A, and 5-HT2A Receptors: A Comparative Binding and Modeling Study. Current Medicinal Chemistry, 2012, 19, 3044-3057.

* cited by examiner

*Primary Examiner* — Robert H Havlin
(74) *Attorney, Agent, or Firm* — Bereskin & Parr LLP/S.E.N.C.R.L., s.r.l.; Michael Fenwick

(57) ABSTRACT

Disclosed are novel carboxylated psilocybin derivative compounds and pharmaceutical and recreational drug formulations containing the same. The compounds may be produced by reacting a reactant psilocybin derivative with a carboxyl or Carboxylic acid derivative containing compound.

17 Claims, 36 Drawing Sheets

CARBOXYLATED PSILOCYBIN DERIVATIVES AND METHODS OF USING

RELATED APPLICATIONS

This application is a continuation of PCT Application No. PCT/CA2021/051712 filed Dec. 1, 2021, which claims the benefit of U.S. Provisional Application No. 63/119,786 filed Dec. 1, 2020 and U.S. Provisional Application No. 63/248,037 filed Sep. 24, 2021; the entire contents of Patent Application Nos. PCT/CA2021/051712, 63/119,786 and 63/248,037 are hereby incorporated by reference.

FIELD OF THE DISCLOSURE

The compositions and methods disclosed herein relate to a chemical compound known as psilocybin. Furthermore, the compositions and methods disclosed herein relate in particular to carboxylated forms of psilocybin.

BACKGROUND OF THE DISCLOSURE

The following paragraphs are provided by way of background to the present disclosure. They are not however an admission that anything discussed therein is prior art or part of the knowledge of a person of skill in the art.

The biochemical pathways in the cells of living organisms may be classified as being part of primary metabolism, or as being part of secondary metabolism. Pathways that are part of a cell's primary metabolism are involved in catabolism for energy production or in anabolism for building block production for the cell. Secondary metabolites, on the other hand, are produced by the cell without having an obvious anabolic or catabolic function. It has long been recognized that secondary metabolites can be useful in many respects, including as therapeutic compounds.

Psilocybin, for example, is a secondary metabolite that is naturally produced by certain mushrooms which taxonomically can be classified as belonging the Basidiomycota division of the fungi kingdom. Mushroom species which can produce psilocybin include species belonging to the genus *Psilocybe*, such as *Psilocybe azurescens, Psilocybe semilanceata, Psilocybe serbica, Psilocybe mexicana*, and *Psilocybe cyanescens*, for example. The interest of the art in psilocybin is well established. Thus, for example, psilocybin is a psychoactive compound and is therefore used as a recreational drug. Furthermore, psilocybin is used as a research tool in behavioral and neuro-imaging studies in psychotic disorders, and has been evaluated for its clinical potential in the treatment of mental health conditions (Daniel, J. et al., Mental Health Clin, 2017; 7(1): 24-28), including to treat anxiety in terminal cancer patients (Grob, C. et al., Arch. Gen. Psychiatry, 2011, 68(1) 71-78) and to alleviate symptoms of treatment-resistant depression (Cathart-Harris, R. L. et al., Lancet Psychiatry, 2016, 3: 619-627).

Although the toxicity of psilocybin is low, adverse side effects, including, for example, panic attacks, paranoia, and psychotic states, sometimes together or individually referred to as "a bad trip", are not infrequently experienced by recreational psilocybin users.

There exists therefore a need in the art for improved psilocybin compounds.

SUMMARY OF THE DISCLOSURE

The following paragraphs are intended to introduce the reader to the more detailed description, not to define or limit the claimed subject matter of the present disclosure.

In one aspect, the present disclosure relates to psilocybin and derivative compounds.

In another aspect, the present disclosure relates to carboxylated psilocybin derivative compounds and methods of making and using these compounds.

Accordingly, in one aspect, the present disclosure provides, in at least one embodiment, in accordance with the teachings herein, a chemical compound having the formula (I):

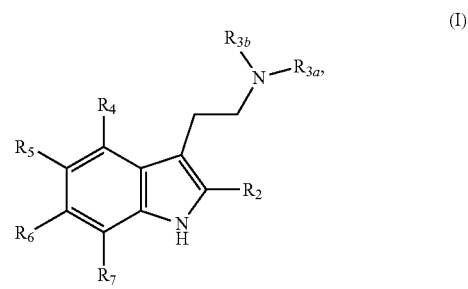

wherein, at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group.

In at least one embodiment, in an aspect, the carboxyl group can be a carboxylate ion and forms a carboxylic acid salt having the formula $COO^-M^+$.

In at least one embodiment, in an aspect, $M^+$ can be selected from $Na^+$, $K^+$ or $NH_4^+$.

In at least one embodiment, in an aspect, the carboxylic acid derivative can be a carboxyl group, wherein the hydroxy group of the carboxyl group is substituted by a substituent having the formula —OR', wherein R' is an alkyl group or an aryl group, to thereby form an ester.

In at least one embodiment, in an aspect, at least two of $R_2$, $R_5$, $R_6$, or $R_7$ can be a carboxyl group or a carboxylic acid derivative.

In at least one embodiment, in an aspect, at least three of $R_2$, $R_5$, $R_6$, or $R_7$ can be a carboxyl group or a carboxylic acid derivative.

In at least one embodiment, in an aspect, all four of $R_2$, $R_5$, $R_6$, or $R_7$ can be a carboxyl group or a carboxylic acid derivative.

In at least one embodiment, in an aspect, $R_5$ or $R_7$ can be a carboxyl group or a carboxylic acid derivative and $R_4$ can be an O-alkyl group.

In at least one embodiment, in an aspect, $R_5$ or $R_7$ can be a carboxyl group or a carboxylic acid derivative and $R_4$ can be an O-acyl group.

In at least one embodiment, in an aspect, $R_5$ or $R_7$ can be a carboxyl group or a carboxylic acid derivative and $R_4$ can be a phosphate group.

In at least one embodiment, in an aspect, $R_5$ or $R_7$ can be a carboxyl group or a carboxylic acid derivative and $R_4$ can be a glycosyloxy group.

In at least one embodiment, in an aspect, $R_5$ or $R_7$ can be a carboxyl group or a carboxylic acid derivative and $R_4$ can be a hydroxy group.

In at least one embodiment, in an aspect, $R_5$ or $R_7$ can be a carboxyl group or a carboxylic acid derivative and $R_4$ can be a hydrogen atom.

In at least one embodiment, in an aspect, $R_5$ and $R_7$ can a carboxyl group or a carboxylic acid derivative and $R_4$ can be an O-alkyl group.

In at least one embodiment, in an aspect, $R_5$ and $R_7$ can be a carboxyl group or a carboxylic acid derivative and $R_4$ can be an O-acyl group.

In at least one embodiment, in an aspect, $R_5$ and $R_7$ can be a carboxyl group or a carboxylic acid derivative and $R_4$ can be a phosphate group.

In at least one embodiment, in an aspect, $R_5$ and $R_7$ can be a carboxyl group or a carboxylic acid derivative and $R_4$ can be a glycosyloxy group.

In at least one embodiment, in an aspect, $R_5$ and $R_7$ can be a carboxyl group or a carboxylic acid derivative and $R_4$ can be a hydroxy group.

In at least one embodiment, in an aspect, $R_5$ and $R_7$ can be a carboxyl group or a carboxylic acid derivative and $R_4$ can be a hydrogen atom.

In at least one embodiment, in an aspect, $R_7$ can be a carboxyl group.

In at least one embodiment, in an aspect, the chemical compound can be selected from the group consisting of compounds having formulas (VI), (VII) and (VIII):

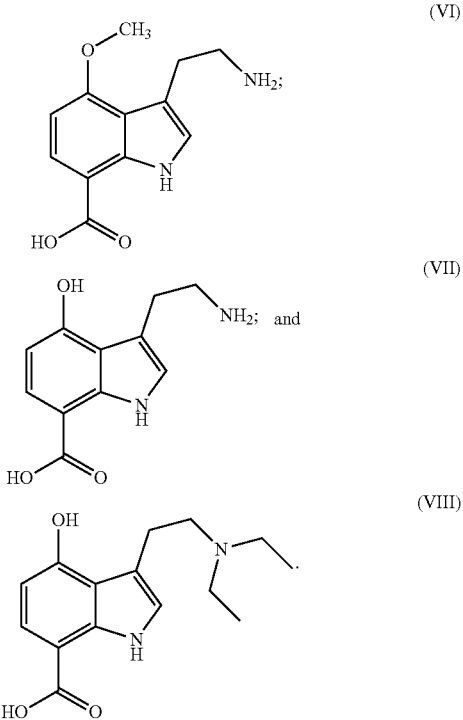

In another aspect, the present disclosure relates to pharmaceutical and recreational drug formulations comprising carboxylated psilocybin derivatives. Accordingly, in one aspect, the present disclosure provides, in at least one embodiment, a pharmaceutical or recreational drug formulation comprising an effective amount of a chemical compound having the formula (I):

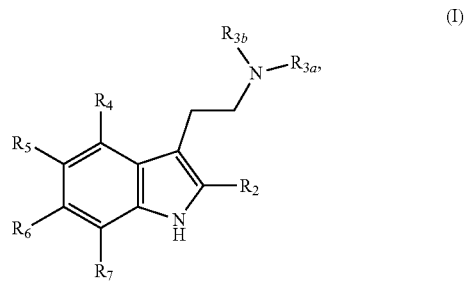

wherein, at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group, together with a pharmaceutically acceptable excipient, diluent or carrier.

In another aspect, the present disclosure relates to methods of treatment of psychiatric disorders. Accordingly, the present disclosure further provides, in one embodiment a method for treating a psychiatric disorder, the method comprising administering to a subject in need thereof a pharmaceutical formulation comprising a chemical compound having the formula (I):

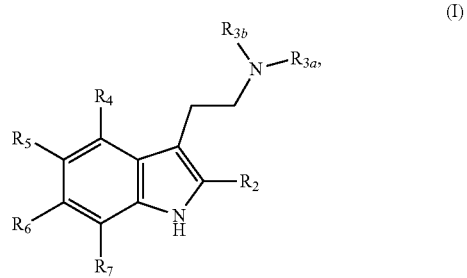

wherein, at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group, wherein the pharmaceutical formulation is administered in an effective amount to treat the psychiatric disorder in the subject.

In at least one embodiment, in an aspect, the disorder can be a 5-$HT_{2A}$ receptor mediated disorder or a 5-$HT_{1A}$ receptor mediated disorder.

In at least one embodiment, in an aspect, a dose can be administered of about 0.001 mg to about 5,000 mg.

In another aspect, the present disclosure relates to methods of making carboxylated psilocybin derivatives. Accordingly, in one aspect, the present disclosure provides, in at least one embodiment, a method of making a carboxylated psilocybin derivative, the method comprising reacting a reactant psilocybin derivative compound with a carboxy-group containing compound under conditions sufficient to form a carboxylated psilocybin derivative.

In at least one embodiment, in an aspect, the reactant psilocybin derivative can be a chemical compound having the formula (II):

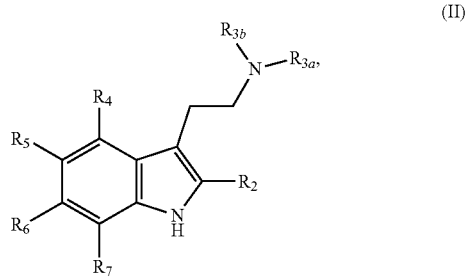

wherein, at least one of $R_2$, $R_5$, $R_6$, or $R_7$ is a hydrogen atom, an alkyl group, O-alkyl group, or a halogen atom, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group.

In at least one embodiment, in an aspect, all of $R_2$, $R_5$, $R_6$, or $R_7$ of chemical compound having formula (II) can be a hydrogen atom.

In at least one embodiment, in an aspect at least one of $R_2$, $R_5$, $R_6$, or $R_7$ of chemical compound having formula (II) can be a hydrogen atom, and wherein at least one of $R_2$, $R_5$, $R_6$, or $R_7$ which are not a hydrogen atom are a carboxyl group or a carboxylic acid derivative.

In at least one embodiment, in an aspect, at least one of $R_2$, $R_5$, $R_6$, or $R_7$ of chemical compound having formula (II) can be a hydrogen atom, and wherein at least two of $R_2$, $R_5$, $R_6$, or $R_7$ which are not a hydrogen atom are a carboxyl group or a carboxylic acid derivative.

In at least one embodiment, in an aspect, at least one of $R_2$, $R_5$, $R_6$, or $R_7$ of chemical compound having formula (II) can be a hydrogen atom, and wherein at least three of $R_2$, $R_5$, $R_6$, or $R_7$ which are not a hydrogen atom are a carboxyl group or a carboxylic acid derivative.

In at least one embodiment, in an aspect, in the formed carboxylated psilocybin derivative at least one of $R_5$ or $R_7$ can be a carboxyl group or a carboxylic acid derivative, and wherein $R_5$, or $R_7$ which are not a carboxyl group or a carboxylic acid derivative, and $R_2$ and $R_6$ are each a hydrogen atom.

In at least one embodiment, in an aspect, in the formed carboxylated psilocybin derivative $R_5$ and $R_7$ can be a carboxyl group or a carboxylic acid derivative, and $R_2$ and $R_6$ are a hydrogen atom.

In at least one embodiment, in an aspect, in chemical compound having formula (II) $R_4$ can be an O-alkyl group, and in the formed carboxylated psilocybin derivative at least one of $R_5$ or $R_7$ can be a carboxyl group or a carboxylic acid derivative, and wherein $R_5$, or $R_7$ which are not a carboxyl group or a carboxylic acid derivative, and $R_2$ and $R_6$ are each a hydrogen atom, and $R_4$ is an O-alkyl group.

In at least one embodiment, in an aspect, in chemical compound having formula (II) $R_4$ can be an O-acyl group, and in the formed carboxylated psilocybin derivative at least one of $R_5$ or $R_7$ can be a carboxyl group or a carboxylic acid derivative, and wherein $R_5$, or $R_7$ which are not a carboxyl group or a carboxylic acid derivative and $R_2$ and $R_6$ are each a hydrogen atom, and $R_4$ is an O-acyl group.

In at least one embodiment, in an aspect, in chemical compound having formula (II) $R_4$ can be a hydroxy group, and in the formed carboxylated psilocybin derivative at least one of $R_5$ or $R_7$ can be a carboxyl group or a carboxylic acid derivative, and wherein $R_5$ or $R_7$ which are not a carboxyl group or a carboxylic acid derivative, and $R_2$ and $R_6$ are each a hydrogen atom, and $R_4$ is a hydroxy group.

In at least one embodiment, in an aspect, in chemical compound having formula (II) $R_4$ can be a phosphate group, and in the formed carboxylated psilocybin derivative at least one of $R_5$ or $R_7$ can be a carboxyl group or a carboxylic acid derivative, and wherein $R_5$ or $R_7$ which are not a carboxyl group or a carboxylic acid derivative and $R_2$ and $R_6$ are each a hydrogen atom, wherein $R_4$ is a phosphate group.

In at least one embodiment, in an aspect, in chemical compound having formula (II) $R_4$ can be a glycosyloxy group, and the formed carboxylated psilocybin derivative at least one of $R_5$ or $R_7$ can be a carboxyl group or a carboxylic acid derivative, and wherein $R_5$, or $R_7$ which are not a carboxyl group or a carboxylic acid derivative and $R_2$ and $R_6$ are each a hydrogen atom, and $R_4$ is a glycosyloxy group.

In at least one embodiment, in an aspect, in chemical compound having formula (II) $R_4$ can be a hydrogen atom, and in the formed carboxylated psilocybin derivative at least one of $R_5$ or $R_7$ can be a carboxyl group or a carboxylic acid derivative, and wherein $R_5$, or $R_7$ which are not a carboxyl group or a carboxylic acid derivative and $R_2$ and $R_6$ are each a hydrogen atom, and $R_4$ is a hydrogen atom.

In at least one embodiment, in an aspect, in chemical compound having formula (II) $R_4$ can be an O-alkyl group, and in the formed carboxylated psilocybin derivative $R_5$ and $R_7$ can be a carboxyl group or a carboxylic acid derivative, and $R_2$ and $R_6$ are a hydrogen atom, and $R_4$ is an O-alkyl group.

In at least one embodiment, in an aspect, in chemical compound having formula (II) $R_4$ can be an O-acyl group, and in the formed carboxylated psilocybin derivative $R_5$ and $R_7$ can be a carboxyl group or a carboxylic acid derivative, and $R_2$ and $R_6$ are a hydrogen atom, and $R_4$ is an O-acyl group.

In at least one embodiment, in an aspect, in chemical compound having formula (II) $R_4$ can be a hydroxy group, and in the formed carboxylated psilocybin derivative at $R_5$ and $R_7$ can be a carboxyl group or a carboxylic acid derivative, and $R_2$ and $R_6$ are a hydrogen atom, and $R_4$ is a hydroxy group.

In at least one embodiment, in an aspect, in chemical compound having formula (II) $R_4$ can be a phosphate group, and in the formed carboxylated psilocybin derivative at $R_5$ and $R_7$ can be a carboxyl group or a carboxylic acid derivative, and $R_2$ and $R_6$ are a hydrogen atom, and $R_4$ is a phosphate group.

In at least one embodiment, in an aspect, in chemical compound having formula (II) $R_4$ can be a glycosyloxy, and in the formed carboxylated psilocybin derivative at $R_5$ and $R_7$ can be a carboxyl group or a carboxylic acid derivative, and $R_2$ and $R_6$ are a hydrogen atom, and $R_4$ is a glycosyloxy group.

In at least one embodiment, in an aspect, in chemical compound having formula (II) $R_4$ can be a hydrogen atom, and in the formed carboxylated psilocybin derivative at $R_5$ and $R_7$ can be a carboxyl group or a carboxylic acid derivative, and $R_2$ and $R_6$ are a hydrogen atom, and $R_4$ is a hydrogen atom.

In at least one embodiment, in an aspect, at least one of $R_2$, $R_5$, $R_6$ or $R_7$ can be a halogen atom and the compound having formula (II) is first reacted with a metallic element or metal containing compound to form an organometallic intermediate, the organometallic intermediate being reacted with carbon dioxide and HCl to form a carboxylated psilocybin derivative, wherein the carboxyl group of the carboxylated psilocybin is being replaced by the halogen atom.

In at least one embodiment, in an aspect, the metallic element can be magnesium.

In at least one embodiment, in an aspect, the metal containing compound can be sec-butyllithium.

In at least one embodiment, in an aspect, the amine nitrogen atom in the compound having formula (II) can be protected by a protective group from reaction with the metallic element or metal containing compound.

In at least one embodiment, in an aspect, $R_4$ in the compound having formula (II) can be a hydroxy group which is protected by a protective group from reaction with the metallic element or metal containing compound.

In at least one embodiment, in an aspect, the protective group can be a benzyl group.

In at least one embodiment, in an aspect, the amine nitrogen atom in the compound having formula (II) can be protected by a protective group and reacted with acetic anhydride to form an acetylated intermediate, the acetylated intermediated being reacted with a halogen to form a carboxylated psilocybin derivative.

In at least one embodiment, the protective group can be a benzyl group, an alkyl group, or an acyl group.

In at least one embodiment, in an aspect, $R_4$ in the compound having formula (II) can be a hydroxy group which is protected by a protective group, wherein the protective group is a benzyl group, an alkyl group, or an acyl group.

In at least one embodiment, in an aspect, $R_7$ can be a carboxyl group.

In at least one embodiment, in an aspect, the method can be a method of making a carboxylated psilocybin compound, the carboxylated psilocybin compound having a chemical formula (IX), (IX)

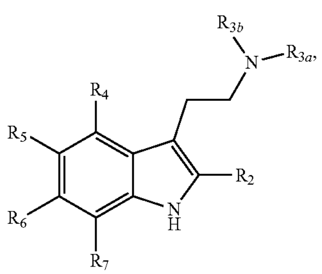

wherein at least one of $R_2$, $R_5$, $R_6$, or $R_7$ is a carboxyl group and wherein each non-carboxylated $R_2$, $R_5$, $R_6$, or $R_7$ is a hydrogen atom, wherein $R_4$ is an O-alkyl group, an O-acyl group, a hydroxy group, a phosphate group, or a glycosyloxy group, and wherein $R_{3A}$ and $R_{3B}$ are each a hydrogen atom, the method comprising:

(a) providing a compound having formula (X):

(X)

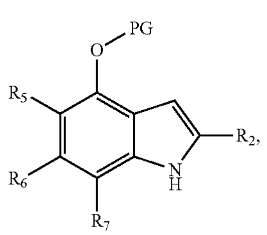

wherein, PG is a protective group, and $R_2$, $R_5$, $R_6$, and $R_7$ are each a hydrogen atom;

(b) nitrovinylating the compound having chemical formula (X) to form a first intermediate compound having chemical formula (XI):

(XI)

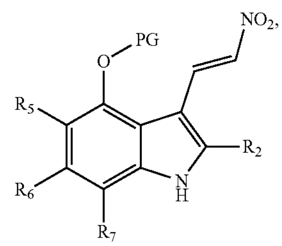

wherein PG is a protective group, and $R_2$, $R_5$, $R_6$, and $R_7$ are each a hydrogen atom;

(c) conjugating the vinyl group of the first intermediate compound to form a second intermediate compound having chemical formula (XII):

(XII)

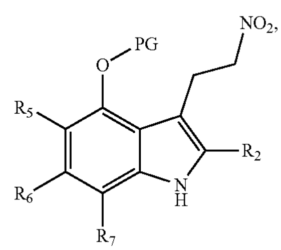

wherein PG is a protective group, and $R_2$, $R_5$, $R_6$, and $R_7$ are each a hydrogen atom;

(d) reacting the second intermediate compound with trifluoracetic anhydride to form a third intermediate compound having chemical formula (XIII):

(XIII)

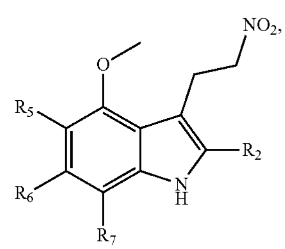

wherein PG is a protective group, at least one of $R_2$, $R_5$, $R_6$, and $R_7$ is a trifluoro-acetyl group, and each of $R_2$, $R_5$, $R_6$, and $R_7$ which are not a trifluoro-acetyl group are a hydrogen atom;

(e) reacting the third intermediate compound under conditions sufficient to remove trifluoro-methyl groups from the third intermediate compound to form in their place carboxyl groups, thereby forming a fourth intermediate compound having chemical formula (XIV):

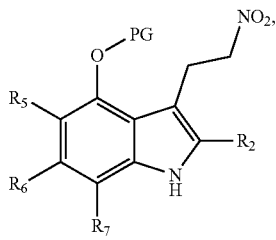

(XIV)

wherein PG is a protective group, at least one of $R_2$, $R_5$, $R_6$, and $R_7$ is a carboxy group, and each of $R_2$, $R_5$, $R_6$, and $R_7$ which are not a carboxy group are a hydrogen atom, and (f) reacting the fourth intermediate compound under reducing conditions to thereby reduce the nitro group and form an amino group and optionally remove the protective group, to form the chemical compound having chemical formula (IX).

In at least one embodiment, in an aspect, at least $R_7$ in step (d) cam acquire a trifluoracetyl group, and $R_7$ in step (e) can be carboxylated.

In at least one embodiment, in an aspect, $R_7$ in step (d) can acquire a trifluoracetyl group and $R_7$ in step (e) can be carboxylated, and wherein $R_2$, $R_5$, and $R_6$, do not acquire a trifluoracetyl group in step (d), and are not carboxylated in step (e).

In at least one embodiment, in an aspect, at least $R_5$ and $R_7$ can acquire a trifluoracetyl group in step (d), and $R_5$ and $R_7$ in step (e) can be carboxylated.

In at least one embodiment, in an aspect, $R_5$ and $R_7$ in step (d) can acquire a trifluoracetyl group and $R_5$ and $R_7$ in step (e) can be carboxylated, and wherein $R_2$ and $R_6$ do not acquire a trifluoracetyl group in step (d), and are not carboxylated in step (e).

In at least one embodiment, in an aspect, O-PG together can be a benzyloxy group, an O-alkyl group, and O-acyl group, a phosphate group, or a glycosyloxy group.

In at least one embodiment, in an aspect, O-PG together can be a benzyloxy group, and wherein the protective group is removed to form a hydroxy group.

In at least one embodiment, in an aspect, O-PG can be an O-alkyl group, an O-acyl group, a phosphate group, or a glycosyloxy group and wherein in step (f) the protective group is not removed.

In at least one embodiment, in an aspect, in step (e) the third intermediate compound can be reacted with a base.

In at least one embodiment, in an aspect, the carboxylated psilocybin derivative having formula (I) or (IX) can be selected from the group consisting of compounds having formulas (VI), (VII), and (VIII):

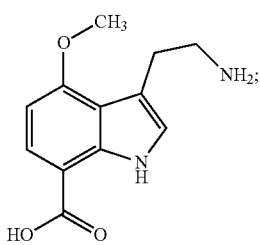

(VI)

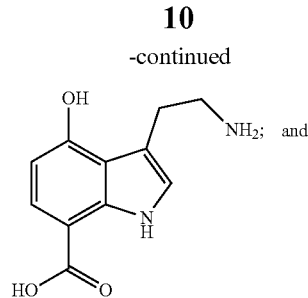

(VII)

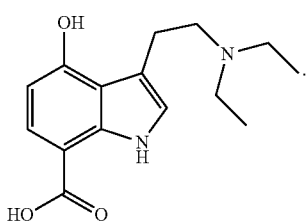

(VIII)

In another aspect, the present disclosure provides, in at least one embodiment, a method for modulating a 5-$HT_{2A}$ receptor or a 5-$HT_{aA}$ receptor, the method comprising contacting a 5-$HT_{2A}$ receptor or a 5-$HT_{aA}$ receptor with a chemical compound or salt thereof having formula (I):

(I)

wherein, at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group, or an acyl group, under reaction conditions sufficient to thereby modulate receptor activity.

In some embodiments, in an aspect, the reaction conditions can be in vitro reaction conditions.

In some embodiments, in an aspect, the reaction conditions can be in vivo reaction conditions.

In another aspect the present disclosure provides, in at least one embodiment, a use of a chemical compound having the formula (I):

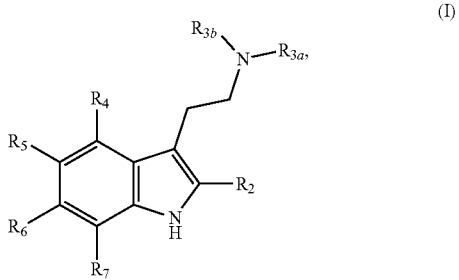

(I)

wherein, at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group, in the manufacture of a pharmaceutical or recreational drug formulation.

In at least one embodiment, in an aspect, the manufacture can comprise formulating the chemical compound with an excipient, diluent or carrier.

In another aspect, the present disclosure provides, in at least one embodiment, a use of a chemical compound having the formula (I):

(I)

wherein, at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group, together with a diluent, carrier, or excipient as a pharmaceutical or recreational drug formulation.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

FIG. 1 depicts the chemical structure of psilocybin.

FIG. 2 depicts a certain prototype structure of psilocybin and psilocybin derivative compounds, namely an indole. Certain carbon and nitrogen atoms may be referred to herein by reference to their position within the indole structure, i.e., $N_1$, $C_2$, $C_3$ etc. The pertinent atom numbering is shown.

FIGS. 3A, 3B, 3C, 3D, 3E, 3F, 3G and 3H depict the chemical structures of certain example carboxylated psilocybin derivatives, notably a 2-carboxyl-psilocybin derivative (FIG. 3A), a 5-carboxyl-psilocybin derivative (FIG. 3B), a 6-carboxyl-psilocybin derivative (FIG. 3C), a 7-carboxyl-psilocybin derivative (FIG. 3D), a 2-OH-substituted-carboxyl-psilocybin derivative (FIG. 3E), a 5-OH-substituted-carboxyl-psilocybin derivative (FIG. 3F), a 6-OH-substituted-carboxyl-psilocybin derivative (FIG. 3G), and a 7-OH-substituted carboxyl-psilocybin derivative (FIG. 3H).

FIGS. 4A and 4B depict the chemical structures of certain example carboxylated psilocybin derivatives, notably a carboxylic acid salt of a 5-carboxyl psilocybin derivative (FIG. 4A) and a 5-OH-ester-substituted carboxyl psilocybin derivative (FIG. 4B).

FIGS. 5A, 5B, 5C, 5D, 5E, 5F, 5G, 5H, 5I, 5J, 5K, 5L, 5M, 5N, 5O, 5P, 5Q, 5R, 5S, 5T, 5U, 5V, 5W and 5X depict the chemical structures of certain example carboxylated psilocybin derivatives, notably alkylated hydroxy-containing psilocybin derivatives, notably a 2,5-di-carboxyl-psilocybin derivative (FIG. 5A), a 2,6-di-carboxyl-psilocybin derivative (FIG. 5B), a 2,7-di-carboxyl-psilocybin derivative (FIG. 5C), a 5,6-di-carboxyl-psilocybin derivative (FIG. 5D), a 5,7-di-carboxyl-psilocybin derivative (FIG. 5E), a 6,7-di-carboxyl-psilocybin derivative (FIG. 5F), a 2,5,6-tri-carboxyl-psilocybin derivative (FIG. 5G), a 2,5,7-tri-carboxyl-psilocybin derivative (FIG. 5H), a 2,6,7-tri-carboxyl-psilocybin derivative (FIG. 5I) a 5,6,7-tri-carboxyl-psilocybin derivative (FIG. 5J), a 2,5,6,7-tetra-carboxyl-psilocybin derivative (FIG. 5K), a 2-OH,5-OH-di-substituted-carboxyl-psilocybin derivative (FIG. 5L), a 2-OH,6-OH-di-substituted-carboxyl-psilocybin derivative (FIG. 5M), a 2-OH,7-OH-di-substituted-carboxyl-psilocybin derivative (FIG. 5N), a 5-OH,6-OH-di-substituted-carboxyl-psilocybin derivative (FIG. 5O), a 5-OH,7-OH-disubstituted-carboxyl-psilocybin derivative (FIG. 5P), a 6-OH,7-OH-di-substituted-carboxyl-psilocybin derivative (FIG. 5Q), a 2-OH,5-OH,6-OH-tri-substituted-carboxyl-psilocybin derivative (FIG. 6R), a 2-OH,5-OH,7-OH-tri-substituted-carboxyl-psilocybin derivative (FIG. 5S), a 2-OH, 6-OH,7-OH-tri-substituted-carboxyl-psilocybin derivative (FIG. 6T) a 5-OH,6-OH,7-OH-tri-substituted-carboxyl-psilocybin derivative (FIG. 5U), a 2-OH,5-OH,6-OH,7-OH-tetra-substituted-carboxyl-psilocybin derivative (FIG. 6V), a 5-carboxyl, 7-OH-substituted-carboxyl-psilocybin derivative (FIG. 5W), and a 5-OH-substituted-carboxyl, 7-carboxyl-psilocybin derivative (FIG. 5X).

FIGS. 6A, 6B, 6C, 6D, 6E, 6F, 6G and 6H depict the chemical structures of certain example carboxylated psilocybin derivatives, notably O-alkylated carboxylated psilocybin derivatives, notably a 4-O-methyl-5-carboxyl-psilocybin derivative (FIG. 6A), a 4-O-ethyl-5-carboxyl-psilocybin derivative (FIG. 68), O-acylated carboxylated psilocybin derivatives, notably a 4-acetyl-5-carboxyl-psilocybin derivative (FIG. 6C), a 4-propanoyl-5-carboxyl-psilocybin derivative (FIG. 6D), a 4-hydroxy-5-carboxyl-psilocybin derivative (FIG. 6E), and a 4-phospho-5-carboxylpsilocybin derivative (FIG. 6F), a 4-glycosyl-5-carboxyl-psilocybin derivative (FIG. 6G), and 5-carboxyl-psilocybin derivative (FIG. 6H).

FIGS. 7A, 7B, 7C, 7D, 7E, 7F, 7G and 7H depict the chemical structures of certain example carboxylated psilocybin derivatives, notably O-alkylated carboxylated psilocybin derivatives, notably a 4-O-methyl-7-carboxyl-psilocybin derivative (FIG. 7A), a 4-O-ethyl-7-carboxyl-psilocybin derivative (FIG. 7B), O-acylated carboxylated psilocybin derivatives, notably a 4-acetyl-7-carboxyl-psilocybin derivative (FIG. 7C), a 4-propanoyl-7-carboxyl-psilocybin derivative (FIG. 7D), a 4-hydroxy-7-carboxyl-psilocybin derivative (FIG. 7E), a 4-phospho-7-carboxyl-psilocybin derivative (FIG. 7F), a 4-glycosyl-7-carboxyl-psilocybin derivative (FIG. 7G), and a 7-carboxyl-psilocybin derivative (FIG. 7H).

FIGS. 8A, 8B, 8C, 8D, 8E, 8F, 8G and 8H depict the chemical structures of certain example carboxylated psilocybin derivatives, notably O-alkylated carboxylated psilocybin derivatives, notably a 4-O-methyl-5,7-di-carboxyl-psilocybin derivative (FIG. 8A), a 4-O-ethyl-5,7-di-carboxyl-psilocybin derivative (FIG. 8B), O-acylated carboxylated psilocybin derivatives, notably a 4-acetyl-5,7-di-carboxyl-psilocybin derivative (FIG. 8C), a 4-propanoyl-5,7-di-carboxyl-psilocybin derivative (FIG. 8D), a 4-hydroxy-5,7-di-carboxyl-psilocybin derivative (FIG. 8E), a 4-phospho-5,7-di-carboxyl-psilocybin derivative (FIG. 8F), a 4-glycosyl-5,7-di-carboxyl-psilocybin derivative (FIG. 8G), and a 5,7-di-carboxyl-psilocybin derivative (FIG. 8H).

FIGS. 9A, 9B, 9C, 9D, 9E, 9F, 9G and 9H depict the chemical structures of certain example psilocybin derivatives, notably O-alkylated psilocybin derivatives, notably a 4-O-methyl-psilocybin derivative (FIG. 9A), a 4-O-ethyl-psilocybin derivative (FIG. 9B), a 4-acetyl-psilocybin derivative (FIG. 9C), a 4-propanoyl-psilocybin derivative (FIG. 9D), a 4-hydroxy-psilocybin derivative, a chemical compound also known as psilocin when $R_{3A}$ and $R_{3B}$ each are each a methyl group (FIG. 9E), a 4-phospho-psilocybin derivative (FIG. 9F), a 4-glycosyl-psilocybin derivative (FIG. 9G), and a 4-hydro-psilocybin derivative (FIG. 9H).

FIGS. 10A, 10B, 10C and 10D depict example chemical reactions showing the formation of a 4-hydroxy-5-carboxyl psilocybin derivative using a 4-O-hydroxy-psilocybin derivative as a reactant (FIG. 10A); a 4-hydroxy-7-carboxyl psilocybin derivative using an aryl halide-psilocybin derivative as a reactant (FIG. 10B); a carboxylated protected psilocybin derivate using a protected psilocybin derivative as a reagent (FIG. 10C), and a sodium salt of a carboxylated psilocybin derivative (a); an OH substituted carboxyl group forming an ester; (b) or an OH substituted carboxyl group forming an amide (c), using a carboxylated psilocybin derivative as a reagent (FIG. 10D).

Figure 13A:
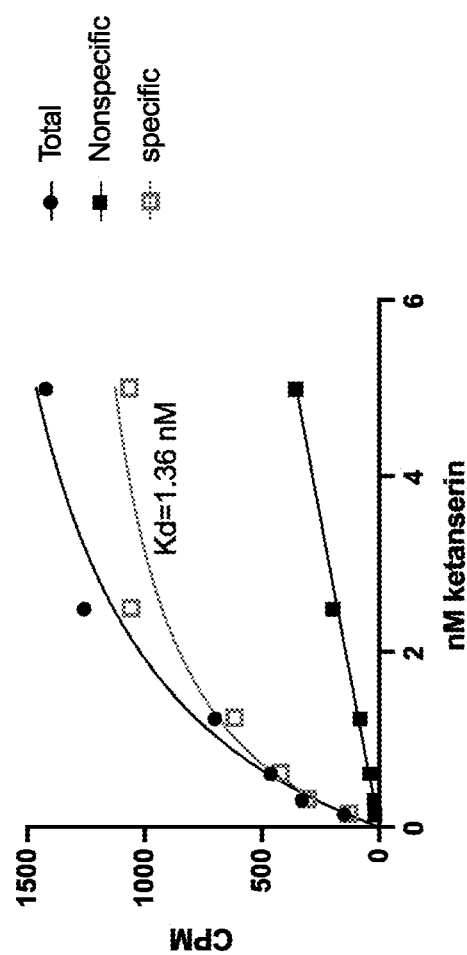
Figure 13A:
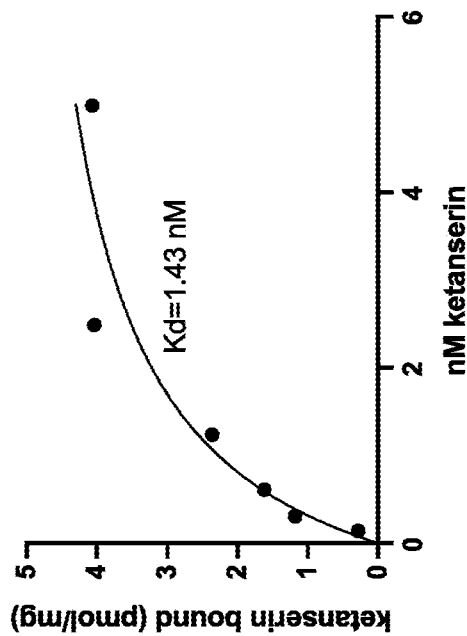
Figure 13B:
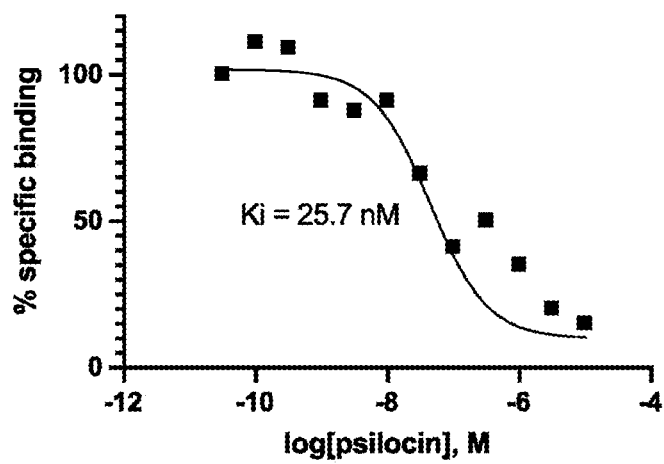
Figure 13C:
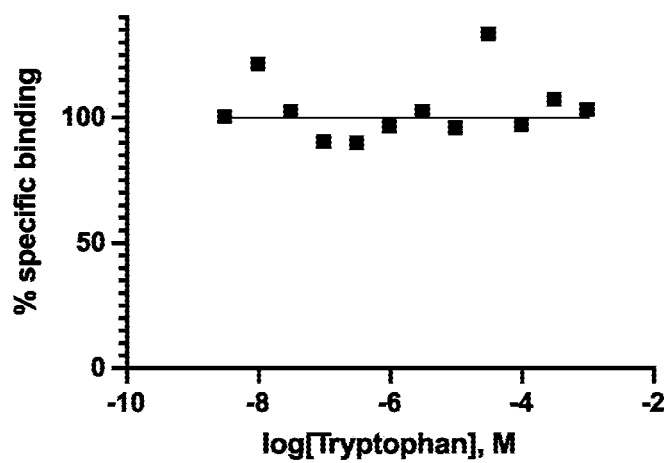
Figure 13D:
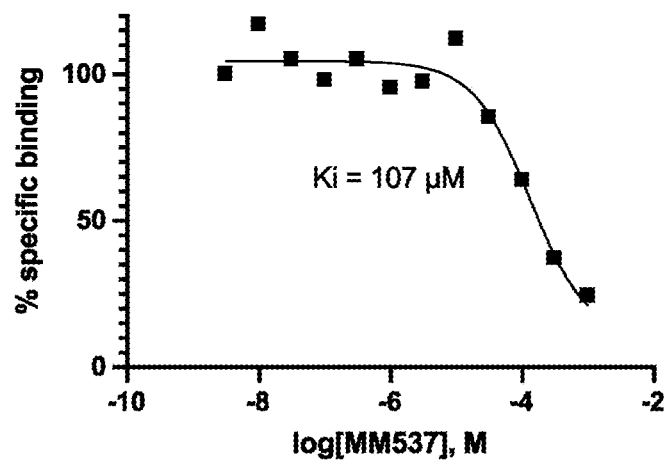
Figure 13E:
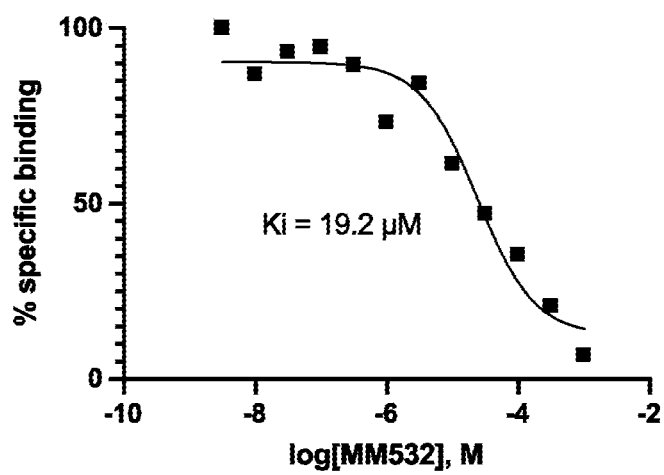

FIGS. 13A, 13B, 13C, 13D and 13E depict various graphs obtained in the performance of experimental assays to evaluate the efficacy of certain example carboxylated psilocybin derivatives, notably carboxylated psilocybin derivatives having the chemical formula (VI) and (VII) set forth herein, notably a saturation binding assay for [$^3$H]ketanserin at the 5-HT$_{2A}$ receptor (FIG. 13A), a competition assay for psilocin as a positive control (binding) (FIG. 13B), a competition assay for tryptophan as a negative control (no binding) (FIG. 13C), a competition assay for a carboxylated psilocybin compound with formula (VI), designated "VI" (FIG. 13D), and another carboxylated psilocybin compound with formula (VII), designated "VII" (FIG. 13E).

Figure 14A:
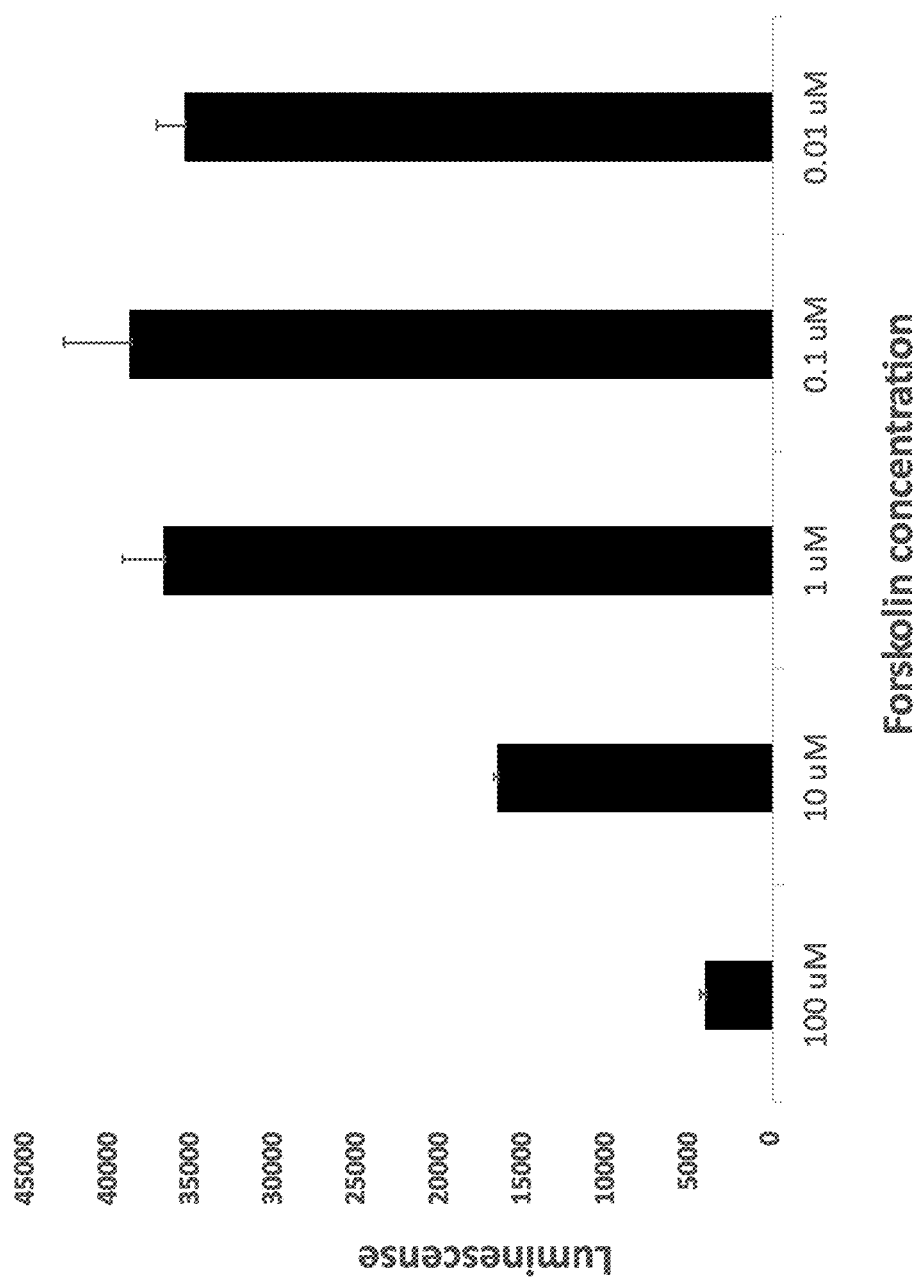
Figure 14B:
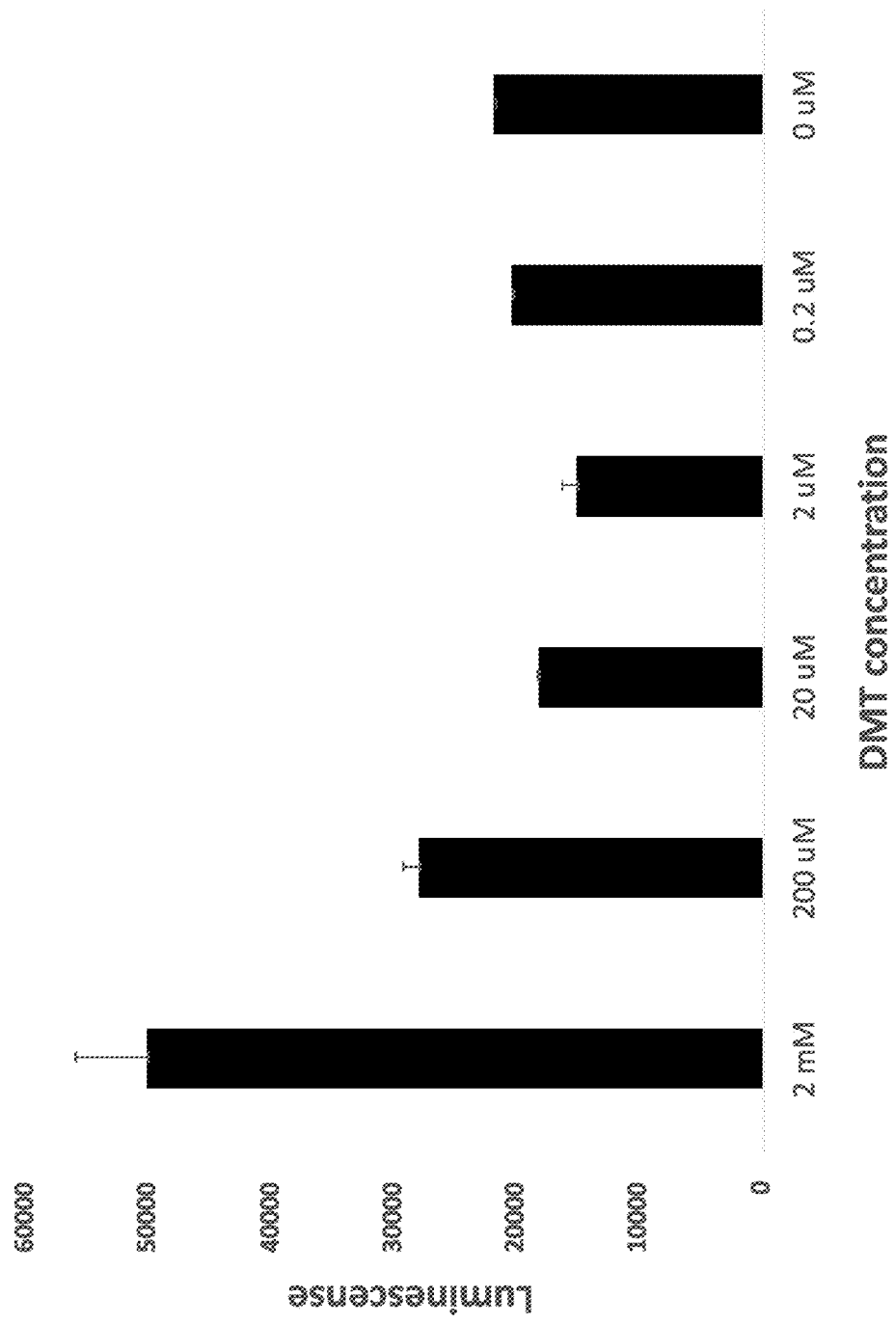
Figure 14C:
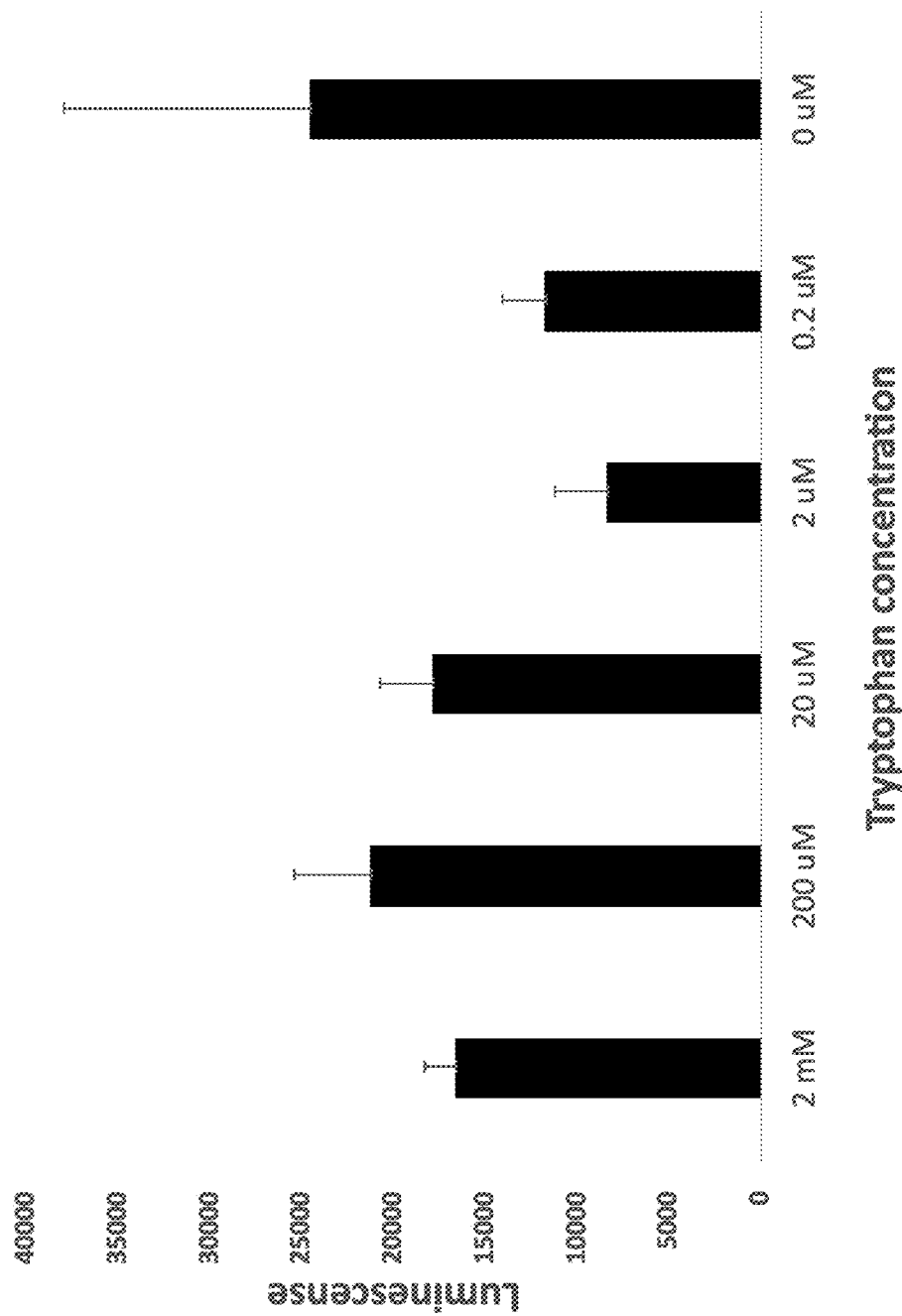
Figure 14D:
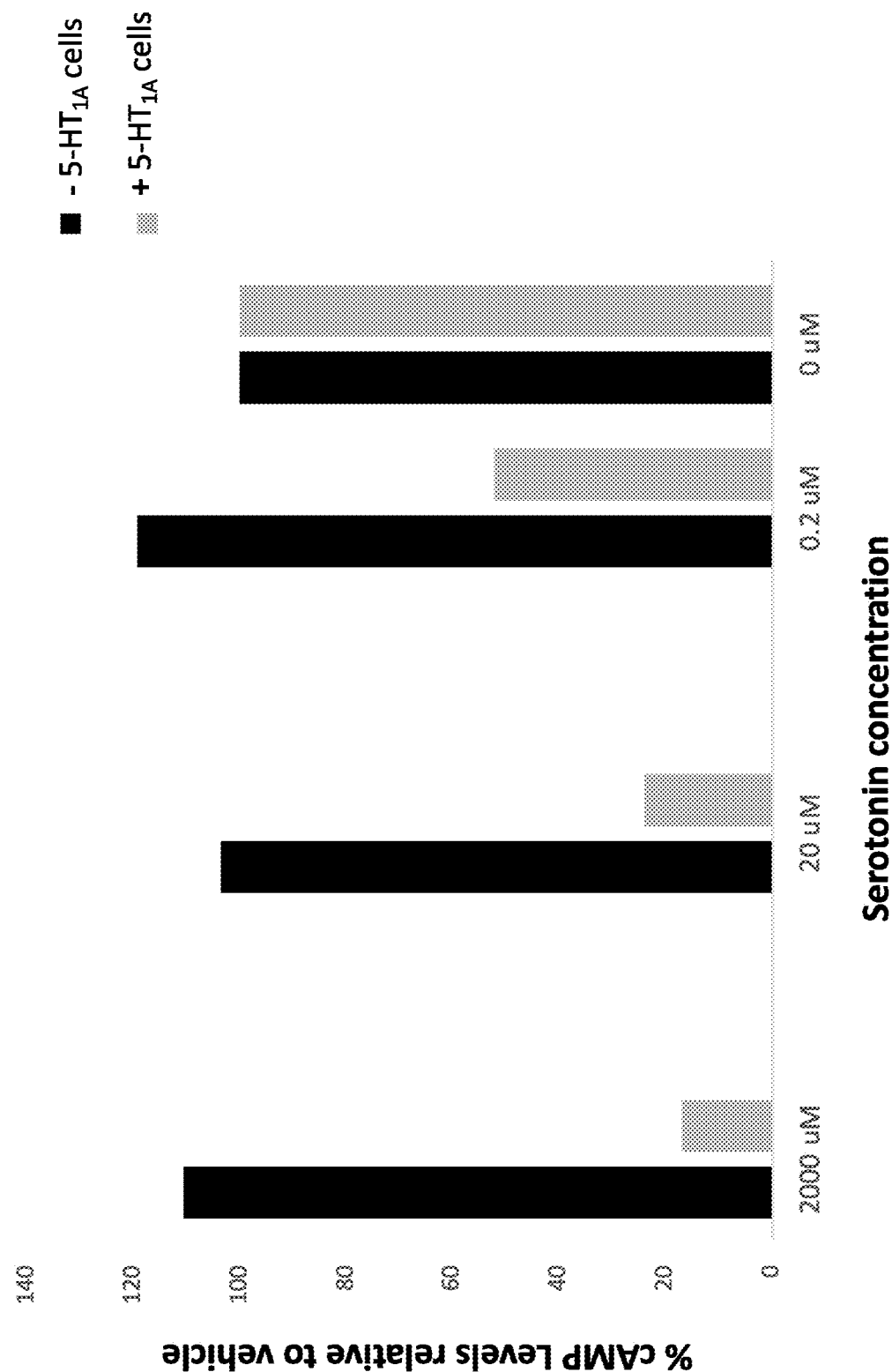
Figure 14E:
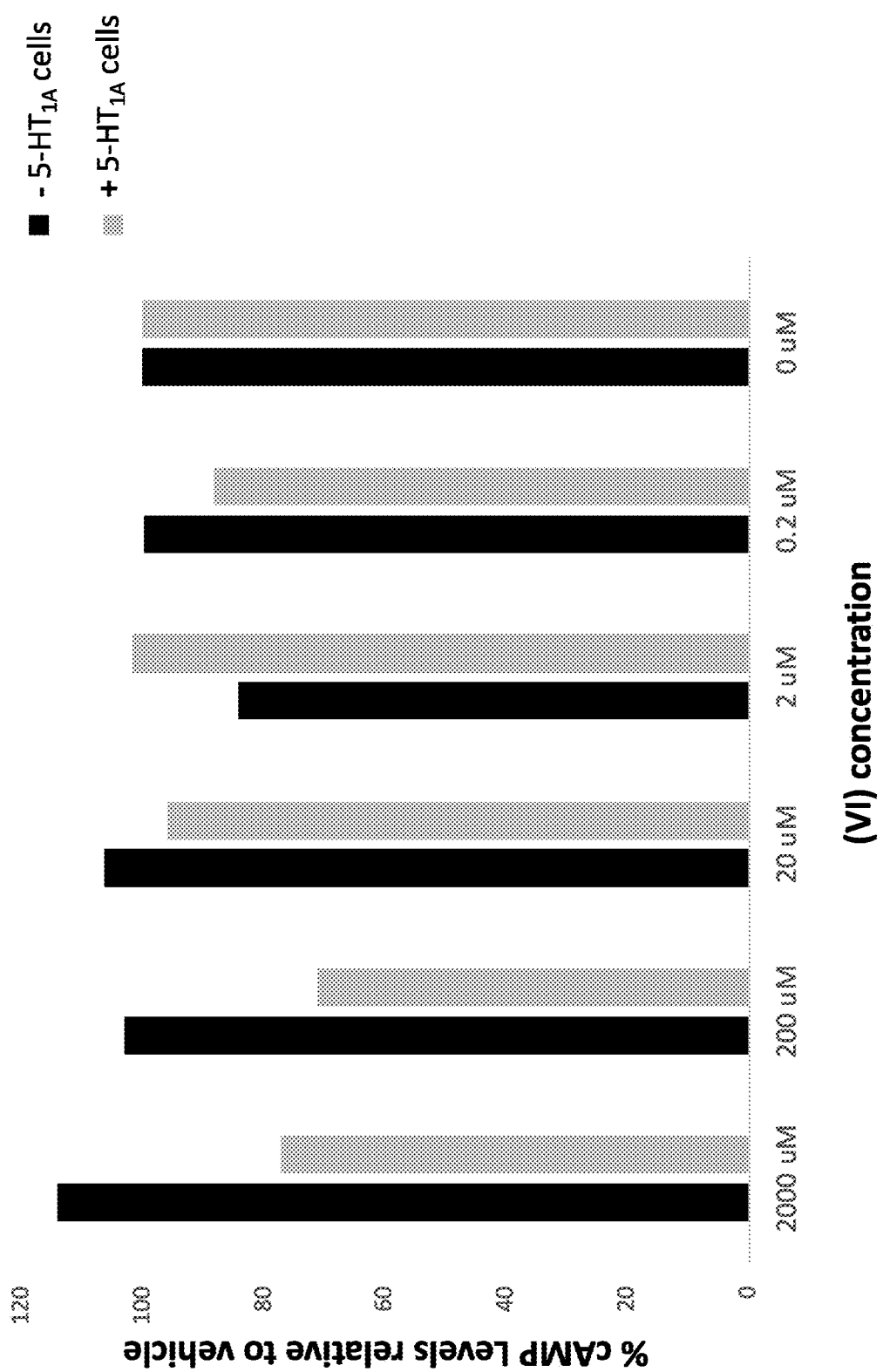
Figure 14F:
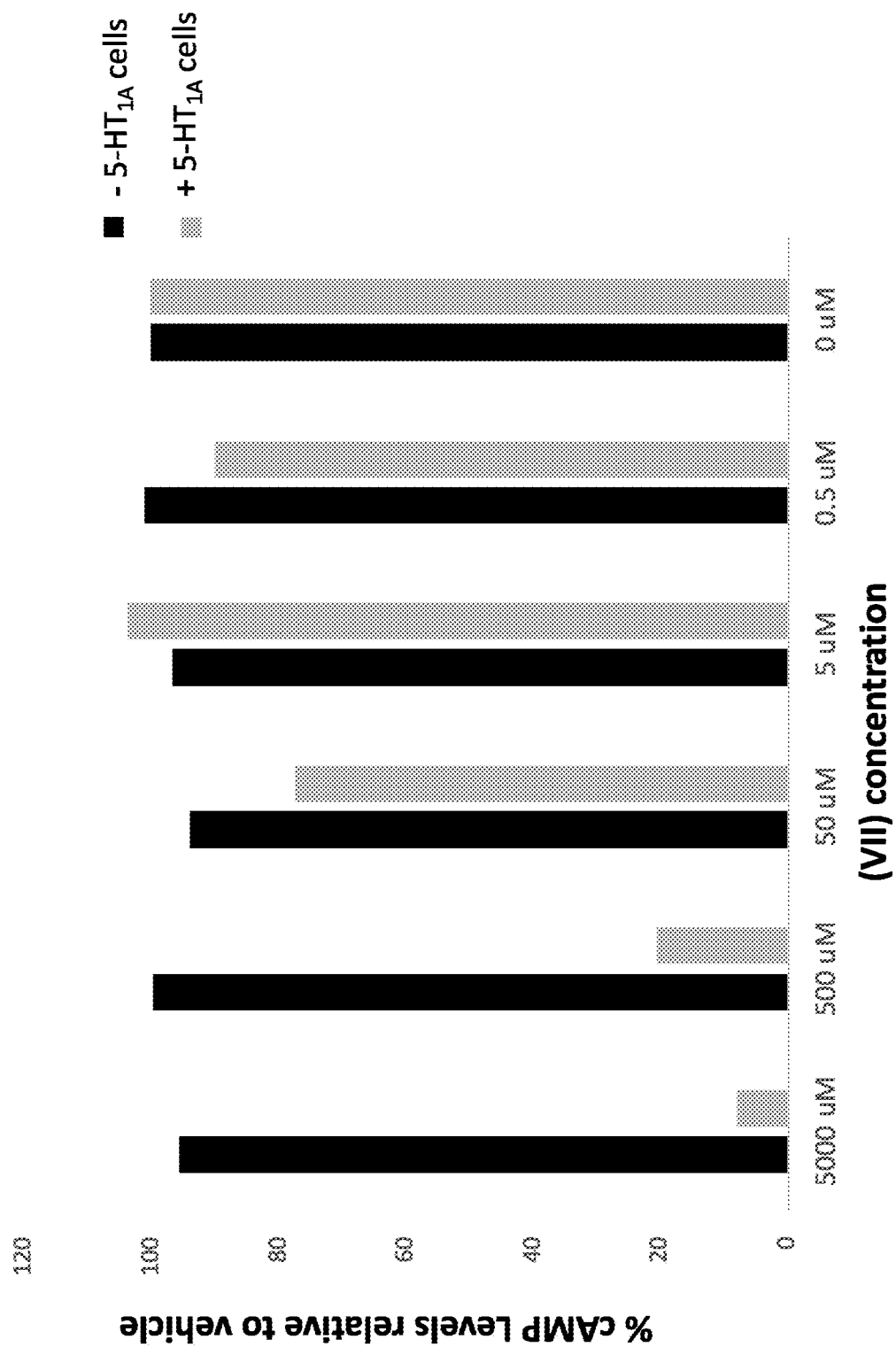

FIGS. 14A, 14B, 14C, 14D, 14E and 14F depict various further graphs, obtained in the performance of experimental assays to evaluate the efficacy of example carboxylated psilocybin derivatives having the chemical formula (VI) and (VII) set forth herein, notably a luminescence assay in +5HT$_{1A}$ cell cultures at various forskolin concentrations (FIG. 14A), a luminescence assay in +5HT$_{1A}$ cell cultures at various DMT concentrations (FIG. 14B), a luminescence assay in +5HT$_{1A}$ cell cultures at various tryptophan concentrations (FIG. 14C), a cAMP assay in the presence of constant (4 μM) forskolin but with increasing serotonin concentration in +5HT$_{1A}$ cells and −5HT$_{1A}$ cells (FIG. 14D), a cAMP assay in the presence of constant (4 μM) forskolin but with increasing concentration of a carboxylated psilocybin compound having formula (VI), designated "VI" in +5HT$_{1A}$ cells and −5HT$_{1A}$ cells ("CHO-K1") cells (FIG. 14E), and a cAMP assay in the presence of constant (4 μM) forskolin but with increasing concentration of a carboxylated psilocybin compound having formula (VI), designated "VII" in +5HT$_{1A}$ cells and −5HT$_{1A}$ cells ("CHO-K1") cells (FIG. 14F).

Figure 15A:
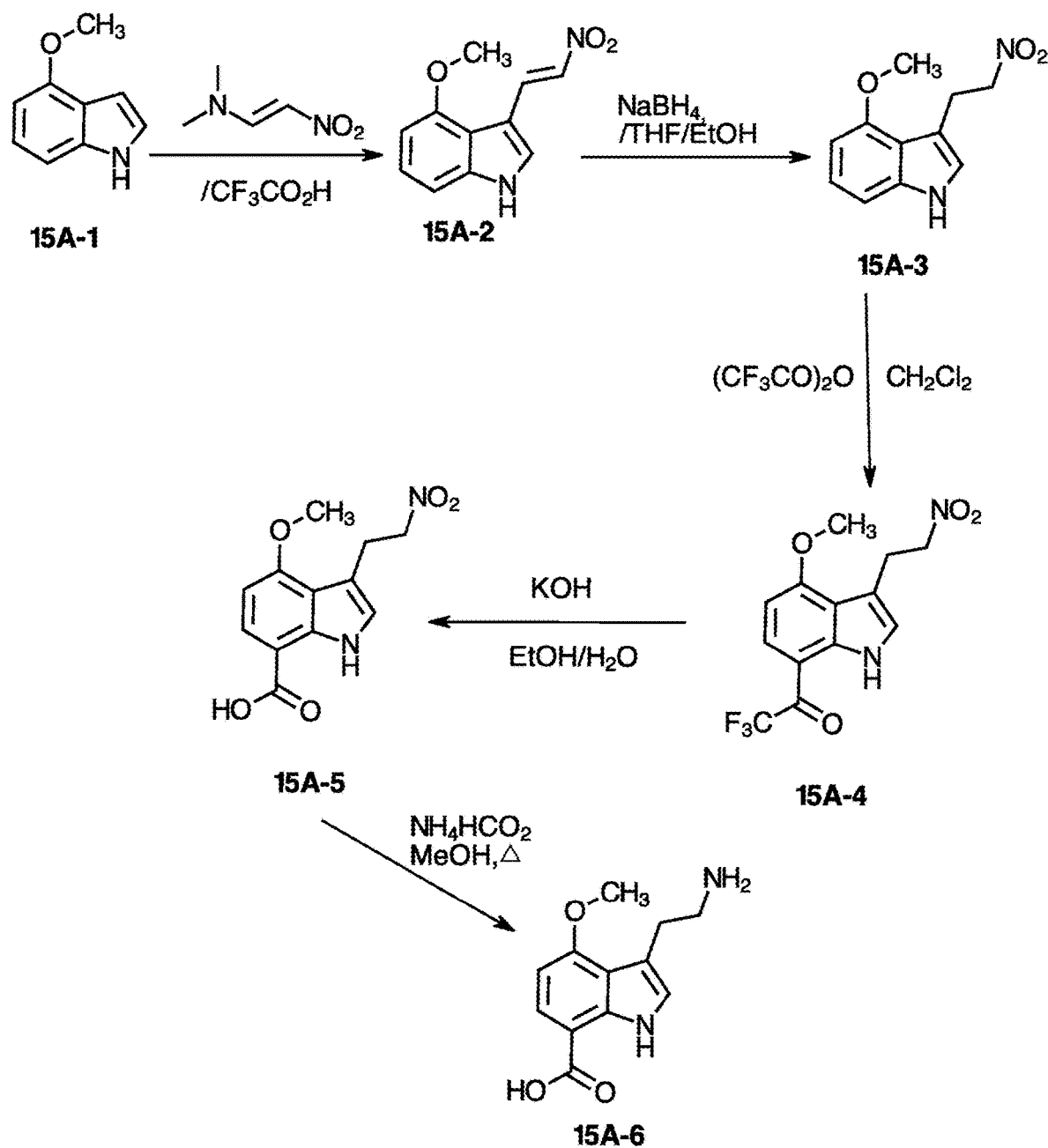
Figure 15B:
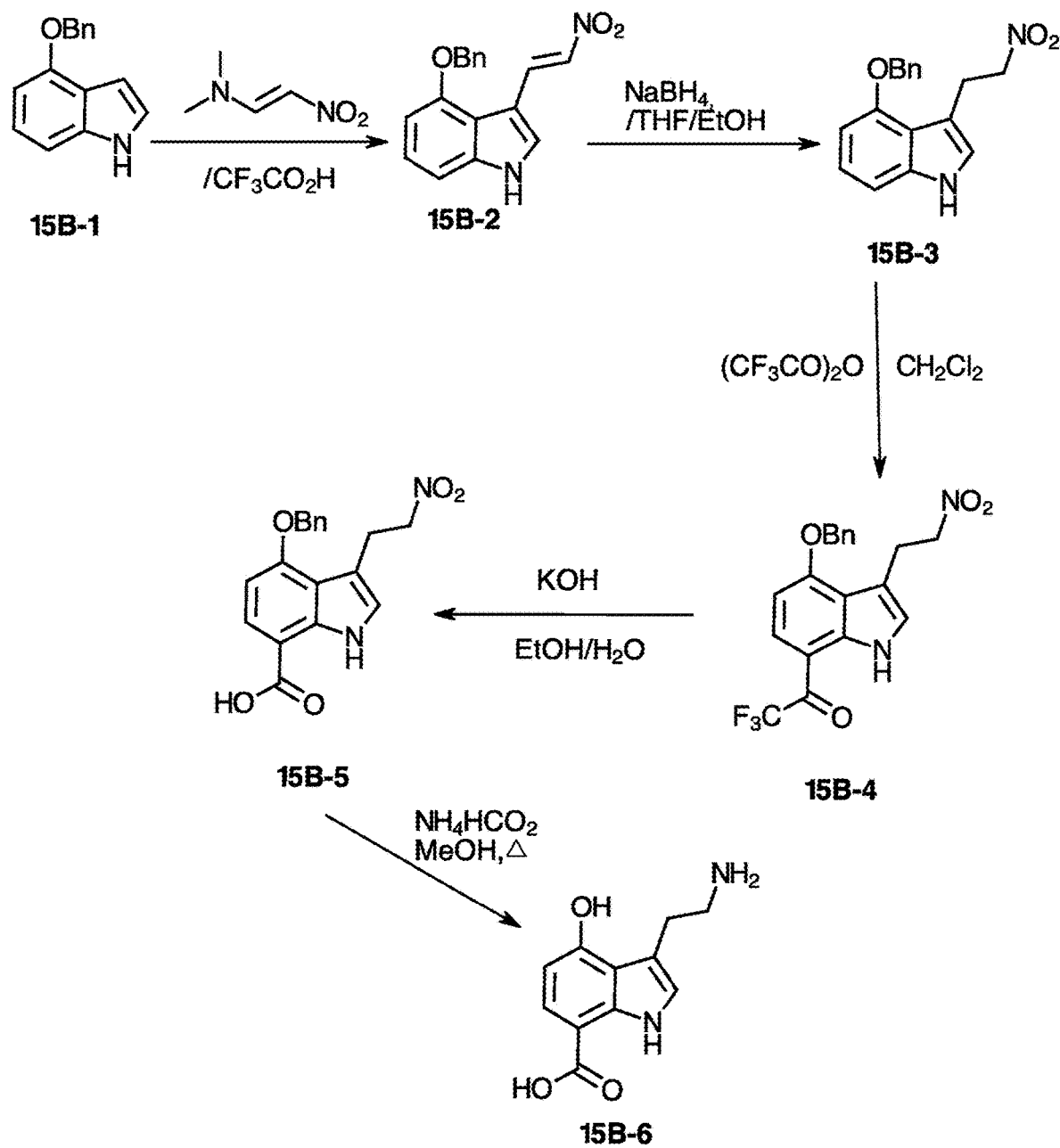

FIGS. 15A and 15B depict example chemical synthesis methods for making carboxylated psilocybin compounds, notably a chemical synthesis method for making a compound having formula (VI) set forth herein (FIG. 15A), and a compound having formula (VII) set forth herein (FIG. 15B).

Figure 16:
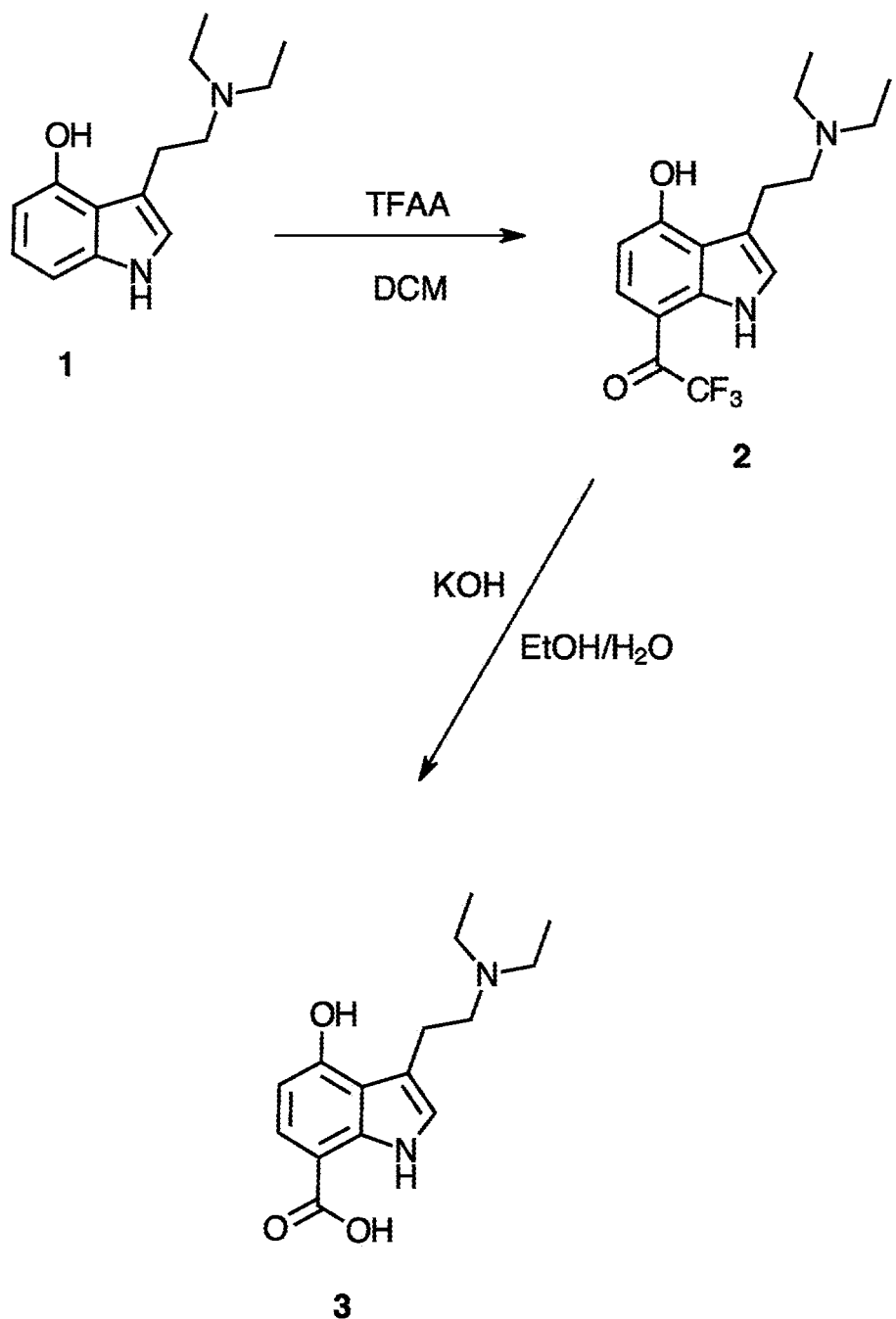

FIG. 16 depicts another example chemical synthesis method for making carboxylated psilocybin compounds, notably a chemical synthesis method for making a compound having formula (VIII) set forth herein.

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore any range of values described herein is intended to specifically include the limiting values of the range, and any intermediate value or sub-range within the given range, and all such intermediate values and sub-ranges are individually and specifically disclosed (e.g., a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent, or patent application was specifically and individually indicated to be incorporated by reference in its entirety.

Terms and Definitions

Figure 1:
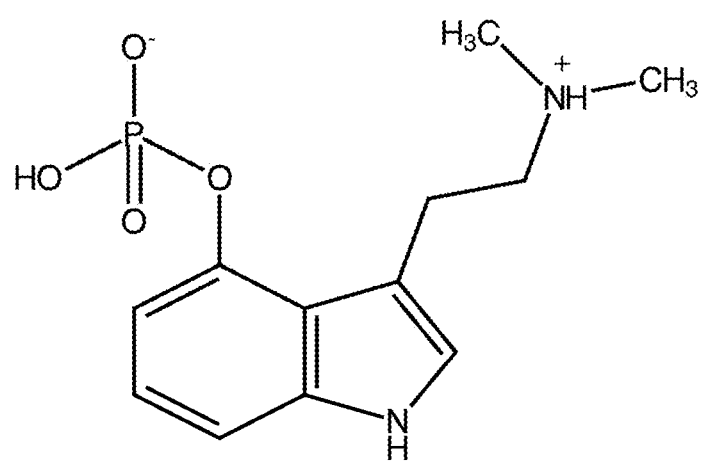

The term "psilocybin", refers to a chemical compound having the structure set forth in FIG. 1.

Figure 2:
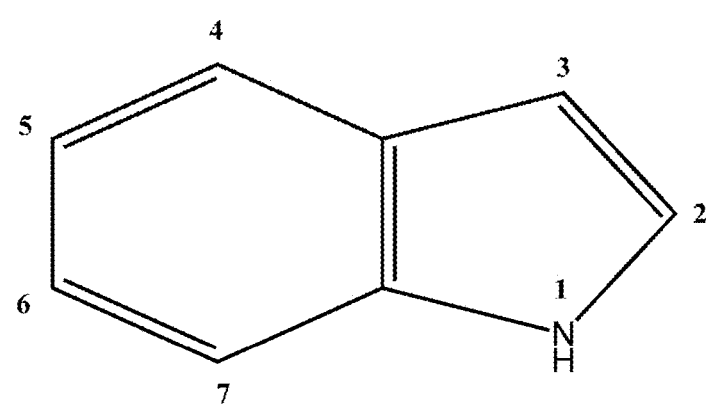

The term "indole prototype structure" refers to the chemical structure shown in FIG. 2. It is noted that specific carbon atoms and a nitrogen atom in the indole prototype structure are numbered. Reference may be made to these carbon and nitrogen numbers herein, for example $C_2$, $C_4$, $N_1$, and so forth. Furthermore, reference may be made to chemical groups attached to the indole prototype structure in accordance with the same numbering, for example $R_4$ and $R_6$ reference chemical groups attached to the $C_4$ and $C_6$ atom, respectively. In addition, $R_{3A}$ and $R_{3B}$, in this respect, reference chemical groups extending from the ethyl-amino group extending in turn from the $C_3$ atom of the prototype indole structure.

The term "carboxylated psilocybin derivative" refers to a psilocybin derivative compound to which a carboxyl group has been bonded to psilocybin or a psilocybin derivative. The hydroxy group of the carboxyl group may be substituted (i.e., a carboxylic acid derivative). OH-substituents can result in the formation of an ester. Reference may be made to specific carbon atoms which may be carboxylated. For example, a 5-carboxyl-psilocybin derivative refers to a psilocybin derivative in which carbon atom number 5 (as identified in the indole prototype structure) possesses a carboxyl group or a carboxylic acid derivative, or, similarly, 7-carboxyl-psilocybin derivative refers to a psilocybin derivative in which carbon atom number 7 (as identified in the indole prototype structure) possess a carboxyl group or a carboxylic acid derivative. Thus, for example, carboxylated psilocybin derivatives include, single carboxyl derivatives, 2-carboxyl, 4-carboxyl, 5-carboxyl, 6-carboxyl, and 7-carboxyl psilocybin derivatives, for example, and multiple carboxyl derivatives, such as, for example, 5,7-di-carboxyl psilocybin derivatives, and 2,5,7-tri-carboxyl psilocybin derivatives. The term carboxylated psilocybin derivatives further includes chemical compounds having the chemical formula (I):

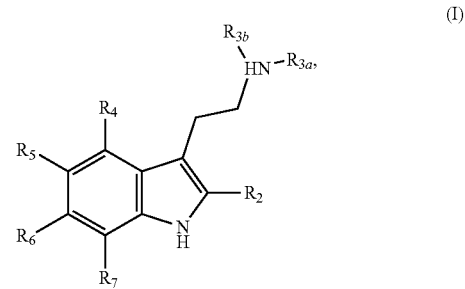

(I)

wherein, at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, an alkyl group, or an O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are a hydrogen atom, an alkyl group, acyl group or an aryl group. Furthermore, it is noted that when $R_4$ is a phosphate group, the term carboxylated psilocybin derivatives includes compounds having the formula (III):

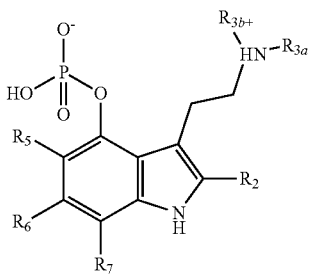

(III)

wherein, at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, an alkyl group, or an O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group. The term further includes salts of carboxylated psilocybins, such as a sodium salt, a potassium salt etc.

The term "phosphate group", as used herein, is a molecule containing one atom of phosphorus, covalently bound to four oxygen atoms (three single bonds and one double bond). Of the four oxygen atoms one oxygen atom may be a hydroxy group, and one of the non-hydroxylated oxygen atom may be chemically bonded to another entity.

The terms "hydroxy group", and "hydroxy", as used herein refers to a molecule containing one atom of oxygen bonded to one atom of hydrogen, and having the formula —OH. A hydroxy group through its oxygen atom may be chemically bonded to another entity.

The terms "carboxyl group", "carboxyl", and "carboxy", as used herein, refer to a molecule containing one atom of carbon bonded to an oxygen atom and a hydroxy group and having the formula —COOH. A carboxyl group includes a deprotonated carboxyl group, i.e., a carboxyl ion, having the formula —COO⁻. In its deprotonated form a carboxyl group may form a carboxyl salt, for example, a sodium or potassium carboxyl salt, or an organic carboxyl salt, all of which may be represented herein as COO⁻M⁺. It is further to be understood that a carboxyl group through its carbon atom may be chemically bonded to another entity. Furthermore, it is noted that an entity attached to a carboxyl group may be referred to herein as a "carboxylated" entity, e.g., a carboxylated psilocybin derivative is a psilocybin derivative possessing either a carboxyl group or a carboxylic acid derivative.

The term "carboxylic acid derivative", as used herein, refers to a carboxyl group wherein the hydroxy group of the carboxyl group has been substituted by another atom or group, such as, for example, an —OR' group. Thus, a carboxylic acid derivative include chemical group (IV):

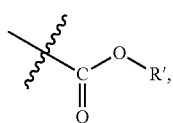

(IV)

Wherein, R', is from an alkyl group, an aryl group and a hydrogen atom. It is noted that chemical group (IV) is an ester. It is further noted that R' can herein additionally include numerical subscripts, such as $_{5a}$, $_{6b}$, $_{7b}$ etc., and be represented, for example, as $R'_{5a}$, $R''_{6b}$ or $R'''_{7a}$, respectively. Where such numerical values are included, they reference chemical entity extending from the carboxyl group extending in turn from the thus numbered C atom of the prototype indole structure. Thus, for example, $R'5a$ is a chemical entity extending from a carboxylated group attached to the $C_5$ atom of the indole ring structure, $R'_{2a}$ is a chemical entity extending from a carboxylated group attached to the $C_2$ atom of the indole ring structure, and so forth. Furthermore, it is noted that an entity attached to a carboxylic acid derivative may be referred to herein as an "carboxylated" entity, e.g., a carboxylated psilocybin derivative is a psilocybin derivative possessing either a carboxyl group or a carboxylic acid derivative.

The terms "glycosylated" or "glycosyl", as used herein, refer to a saccharide group, such as a mono-, di-, tri-oligo- or a poly-saccharide group, which can be or has been bonded from its anomeric carbon either in the pyranose or furanose form, either in the a or the P conformation. When bonded through its anomeric carbon via an oxygen atom to another entity, the bonded saccharide group, inclusive of the oxygen atom, may be referred to herein as a "glycosyloxy" group. Example monosaccharide groups include, but are not limited to, a pentosyl, a hexosyl, or a heptosyl group. The glycosyloxy group may also be substituted with various groups. Such substitutions may include lower alkyl, lower alkoxy, acyl, carboxy, carboxyamino, amino, acetamido, halo, thio, nitro, keto, and phosphatyl groups, wherein the substitution may be at one or more positions on the saccharide. Included in the term glycosyl are further stereoisomers, optical isomers, anomers, and epimers of the glycosyloxy group. Thus, a hexose group, for example, can be either an aldose or a ketose group, can be of D- or L-configuration, can assume either an a or P conformation, and can be a dextro- or levo-rotatory with respect to plane-polarized light. Example glycosyloxy groups further include, without limitation, glucosyl groups, glucuronic acid groups, galactosyl groups, fucosyl groups, xylose groups, arabinose groups, and rhamnose groups.

The term "alkyl group" refers to a straight and/or branched chain, saturated alkyl radical containing from one to "p" carbon atoms ("$C_1$-$C_p$-alkyl") and includes, depending on the identity of "p", methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl, and the like, where the variable p is an integer representing the largest number of carbon atoms in the alkyl radical. Alkyl groups further include hydrocarbon groups arranged in a chain having the chemical formula —$C_nH_{2n+1}$, including, without limitation, methyl groups (—$CH_3$), ethyl groups (—$C_2H_5$), propyl groups (—$C_3H_7$), and butyl groups (—$C_4H_9$).

The term "O-alkyl group", refers to a hydrocarbon group arranged in a chain having the formula —O—$C_nH_{2n+1}$. Alkyl groups include, without limitation, O-methyl groups (—O—$CH_3$), O-ethyl groups (—O—$C_2H_5$), O-propyl groups (—O—$C_3H_7$) and O-butyl groups (—O—$C_4H_9$).

The term "acyl group" refers to a carbon atom double bonded to an oxygen and single bonded to an alkyl group. The carbon atom further can be bonded to another entity. An acyl group can be described by the chemical formula: —C(=O)—$C_nH_{2n+1}$.

The term "O-acyl group" refers to an acyl group in which the carbon atom is single bonded to an additional oxygen atom. The additional oxygen atom can be bonded to another entity. An O-acyl group can be described by the chemical formula: —O—C(=O)—$C_nH_{2n+1}$. Furthermore, depending on the carbon chain, length specific O-acyl groups may be termed an acetyl group (n=1), a propanoyl group (n=2), propoxycarbonyl group (n=3), a butoxycarbonyl group (n=4) etc.

The term "halogen", "halogenated" and "halo-", as used herein, refers to the class of elements consisting of fluorine (F), chlorine ($C_1$), bromine (Br), and iodine (1). Accordingly, halogenated compounds can refer to "fluorinated", "chlorinated", "brominated", or "iodinated" compounds.

The term "5-$HT_{2A}$ receptor", as used herein, refers to a subclass of a family of receptors for the neurotransmitter and peripheral signal mediator serotonin. 5-$HT_{2A}$ receptors can mediate a plurality of central and peripheral physiologic functions of serotonin. Central nervous system effects can include mediation of hallucinogenic effects of hallucinogenic compounds.

The term "modulating 5-$HT_{2A}$ receptors", as used herein, refers to the ability of a compound disclosed herein to alter the function of 5-$HT_{2A}$ receptors. A 5-$HT_{2A}$ receptor modulator may activate the activity of a 5-$HT_{2A}$ receptor, may activate or inhibit the activity of a 5-$HT_{2A}$ receptor depending on the concentration of the compound exposed to the 5-$HT_{2A}$ receptor, or may inhibit the activity of a 5-$HT_{2A}$ receptor. Such activation or inhibition may be contingent on the occurrence of a specific event, such as activation of a signal transduction pathway, and/or maybe manifest only in particular cell types. The term "modulating 5-$HT_{2A}$ receptors," also refers to altering the function of a 5-$HT_{2A}$ receptor by increasing or decreasing the probability that a complex forms between a 5-$HT_{2A}$ receptor and a natural binding partner to form a multimer. A 5-$HT_{2A}$ receptor modulator may increase the probability that such a complex forms between the 5-$HT_{2A}$ receptor and the natural binding partner, may increase or decrease the probability that a complex forms between the 5-$HT_{2A}$ receptor and the natural binding partner depending on the concentration of the compound exposed to the 5-$HT_{2A}$ receptor, and or may decrease the probability that a complex forms between the 5-$HT_{2A}$ receptor and the natural binding partner.

The term "5-$HT_{2A}$ receptor-mediated disorder", as used herein, refers to a disorder that is characterized by abnormal 5-$HT_{2A}$ receptor activity. A 5-$HT_{2A}$ receptor-mediated disorder may be completely or partially mediated by modulating 5-$HT_{2A}$ receptors. In particular, a 5-$HT_{2A}$ receptor-mediated disorder is one in which modulation of 5-$HT_{2A}$ receptors results in some effect on the underlying disorder e.g., administration of a 5-$HT_{2A}$ receptor modulator results in some improvement in at least some of the subjects being treated.

The term "5-$HT_{1A}$ receptor", as used herein, refers to a subclass of a family of receptors for the neurotransmitter and peripheral signal mediator serotonin. 5-$HT_{1A}$ receptors can mediate a plurality of central and peripheral physiologic functions of serotonin. Ligand activity at 5-$HT_{1A}$ is generally not associated with hallucination, although many hallucinogenic compounds are known to modulate 5-$HT_{1A}$ receptors to impart complex physiological responses (Inserra et al., 2020, Pharmacol Rev 73: 202).

The term "modulating 5-$HT_{1A}$ receptors", as used herein, refers to the ability of a compound disclosed herein to alter the function of 5-$HT_{1A}$ receptors. A 5-$HT_{1A}$ receptor modulator may activate the activity of a 5-$HT_{1A}$ receptor, may activate or inhibit the activity of a 5-$HT_{1A}$ receptor depending on the concentration of the compound exposed to the 5-$HT_{1A}$ receptor, or may inhibit the activity of a 5-$HT_{1A}$ receptor. Such activation or inhibition may be contingent on the occurrence of a specific event, such as activation of a signal transduction pathway, and/or maybe manifest only in particular cell types. The term "modulating 5-$HT_{1A}$ receptors," also refers to altering the function of a 5-$HT_{1A}$ receptor by increasing or decreasing the probability that a complex forms between a 5-$HT_{1A}$ receptor and a natural binding partner to form a multimer. A 5-$HT_{1A}$ receptor modulator may increase the probability that such a complex forms between the 5-$HT_{1A}$ receptor and the natural binding partner, may increase or decrease the probability that a complex forms between the 5-$HT_{1A}$ receptor and the natural binding partner depending on the concentration of the compound exposed to the 5-$HT_{1A}$ receptor, and or may decrease the probability that a complex forms between the 5-$HT_{1A}$ receptor and the natural binding partner.

The term "5-$HT_{1A}$ receptor-mediated disorder", as used herein, refers to a disorder that is characterized by abnormal 5-$HT_{1A}$ receptor activity. A 5-$HT_{1A}$ receptor-mediated disorder may be completely or partially mediated by modulating 5-$HT_{1A}$ receptors. In particular, a 5-$HT_{1A}$ receptor-mediated disorder is one in which modulation of 5-$HT_{1A}$ receptors results in some effect on the underlying disorder e.g., administration of a 5-$HT_{1A}$ receptor modulator results in some improvement in at least some of the subjects being treated.

The term "pharmaceutical formulation", as used herein, refers to a preparation in a form which allows an active ingredient, including a psychoactive ingredient, contained therein to provide effective treatment, and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term "recreational drug formulation", as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term "effective for administration as a recreational drug", as used herein, refers to a preparation in a form which allows a subject to voluntarily induce a psychoactive effect for non-medical purposes upon administration, generally in the form of self-administration. The effect may include an altered state of consciousness, satisfaction, pleasure, euphoria, perceptual distortion, or hallucination.

The term "effective amount", as used herein, refers to an amount of an active agent, pharmaceutical formulation, or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms "treating" and "treatment", and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental and psychiatric diseases and disorders. Clinical evidence of the prevention or treatment may vary with the disorder, or disease, the subject, and the selected treatment.

The term "pharmaceutically acceptable", as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The terms "substantially pure" and "isolated", as may be used interchangeably herein describe a compound, e.g., a psilocybin derivative, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

General Implementation

As hereinbefore mentioned, the present disclosure relates to psilocybin derivatives. In particular, the present disclosure provides novel carboxylated psilocybin derivatives. In general, the herein provided compositions exhibit functional properties which deviate from the functional properties of psilocybin. Thus, for example, the carboxylated psilocybin derivatives, can exhibit pharmacological properties which deviate from psilocybin. Furthermore, the carboxylated derivatives may psilocybin derivatives may exhibit physicochemical properties which differ from psilocybin. Thus, for example, carboxylated psilocybin derivatives may exhibit superior solubility in a solvent, for example, an aqueous solvent. The carboxylated psilocybin derivatives in this respect are useful in the formulation of pharmaceutical and recreational drug formulations. In one embodiment, the carboxylated psilocybin derivatives of the present disclosure can conveniently be biosynthetically produced. The practice of this method avoids the extraction of psilocybin from mushrooms and the performance of subsequent chemical reactions to achieve carboxylated derivatives. Furthermore, the growth of mushrooms can be avoided thus limiting the dependence on climate and weather, and potential legal and social challenges associated with the cultivation of mushrooms containing psychoactive compounds. The method can efficiently yield substantial quantities of carboxylated psilocybin derivatives.

In what follows selected embodiments are described with reference to the drawings.

Initially example carboxylated psilocybin derivatives will be described. Thereafter example methods of using and making the carboxylated psilocybin derivatives will be described.

Accordingly, in one aspect the present disclosure provides derivatives of a compound known as psilocybin of which the chemical structure is shown in FIG. 1. The derivatives herein provided are, in particular, carboxylated derivatives including psilocybin derivatives possessing a carboxyl group or a carboxylic acid derivative.

Thus, in one aspect, the present disclosure provides, in accordance with the teachings herein, in at least one embodiment, a chemical compound having the formula (I):

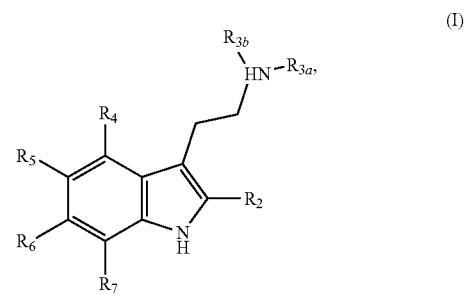

wherein, at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group.

Thus, referring to the chemical compound having the formula (I), initially it is noted that, in an aspect hereof, at least one of $R_2$, $R_5$, $R_6$, or $R_7$ is a carboxyl group or a carboxylic acid derivative.

Figure 4A:
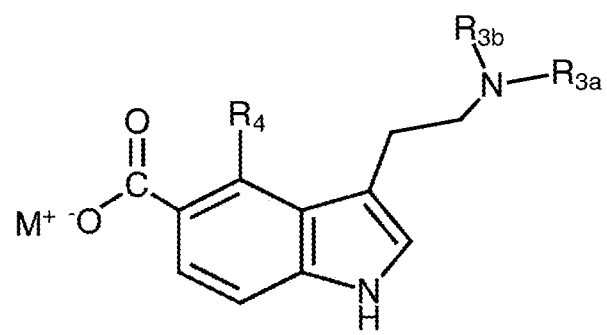

In one aspect, in an embodiment, the carboxyl group can be a carboxylate ion and form a carboxylic acid salt having the formula $COO^-M^+$. Thus for example $M^+$ can be sodium ($Na^+$), potassium ($K^+$), ammonium ($NR_4^+$, R=H, alkyl, aryl), or any other organic and inorganic cations, and the chemical compound having formula (I) can be a sodium salt, a potassium salt, an ammonium salt, or an ammonium derivative salt, respectively. An example, of such an embodiment is shown in FIG. 4A.

Figure 4B:
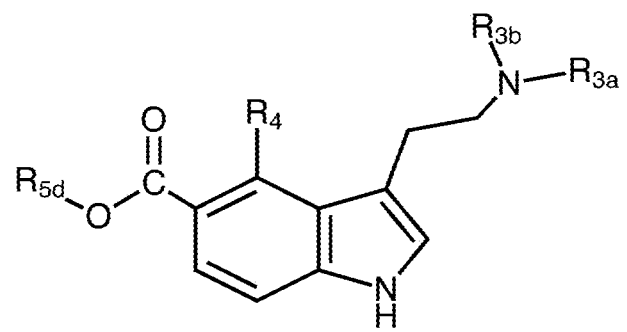

In one aspect, in a further embodiment, at least one of $R_2$, $R_5$, $R_6$, or $R_7$ can be a carboxylic acid derivative, wherein the hydroxy group of the carboxyl group is substituted by a substituent having the formula —OR', wherein R' is an alkyl group or an aryl group, to thereby form an ester. Thus, for example, in one embodiment, the carboxylic acid derivative can be a chemical group having formula (IV):

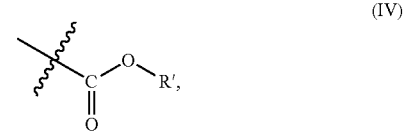

wherein R' is an alkyl group or an aryl group. An example of such embodiment is shown in FIG. 4B.

In a further aspect, $R_2$, $R_5$, $R_6$, or $R_7$ can be a carboxyl group or a carboxylic acid derivative wherein two, or at least two, hydrogen atoms are substituted by a carboxyl group or a carboxylic acid derivative.

In a further aspect hereof, $R_{3A}$ and $R_{3B}$ can be a hydrogen atom, an alkyl group, an acyl group, or an aryl group. Thus, $R_{3A}$ and $R_{3B}$ can each be a hydrogen atom, or $R_{3A}$ and $R_{3B}$ can each be an alkyl group, such as a methyl group, ethyl group, propyl group, or longer chain alkyl group, or $R_{3A}$ and $R_{3B}$ can be each be an acyl group, or $R_{3A}$ and $R_{3B}$ can each be an aryl group. Furthermore, one of $R_{3A}$ and $R_{3B}$ can be a hydrogen atom, and one of $R_{3A}$ and $R_{3B}$ can be an alkyl group. One of $R_{3A}$ and $R_{3B}$ can be a hydrogen atom, and one of $R_{3A}$ and $R_{3B}$ can be an acyl group. One of $R_{3A}$ and $R_{3B}$ can be a hydrogen atom, and one of $R_{3A}$ and $R_{3B}$ can be an aryl group. One of $R_{3A}$ and $R_{3B}$ can be an alkyl group, and one of $R_{3A}$ and $R_{3B}$ can be an aryl group. One of $R_{3A}$ and $R_{3B}$ can be an alkyl group, and one of $R_{3A}$ and $R_{3B}$ can be an acyl group. One of $R_{3A}$ and $R_{3B}$ can be an acyl group, and one of $R_{3A}$ and $R_{3B}$ can be an aryl group.

In a further aspect hereof, $R_4$ can be an O-alkyl group, an O-acyl group, a hydroxy group, a phosphate group, a glycosyloxy group, or a hydrogen atom.

Figure 3A:
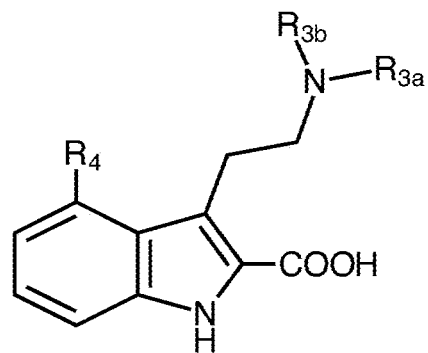
Figure 3B:
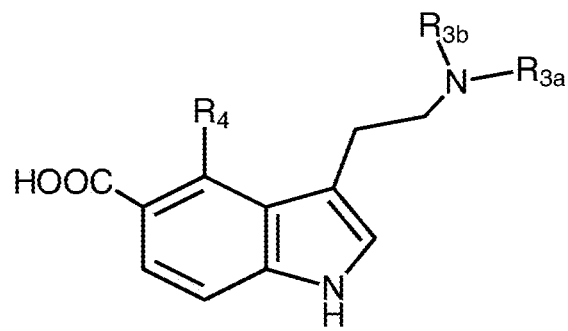
Figure 3C:
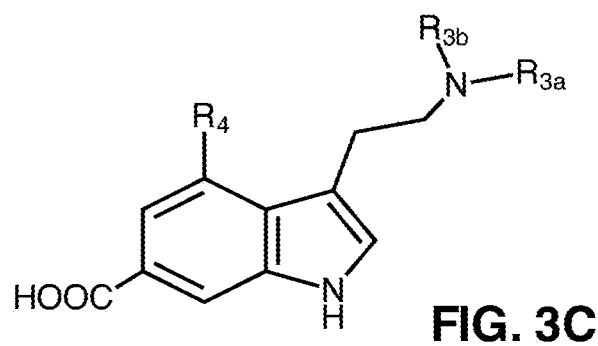
Figure 3D:
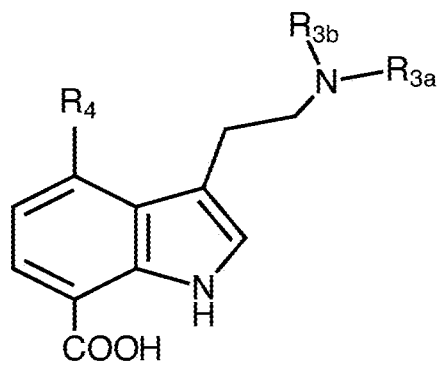
Figure 3E:
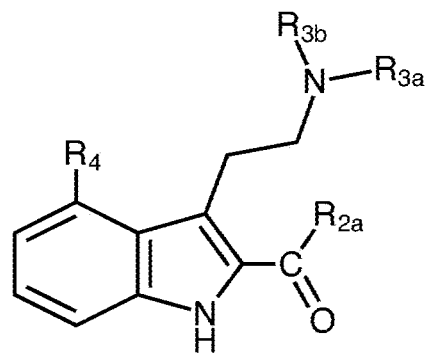
Figure 3F:
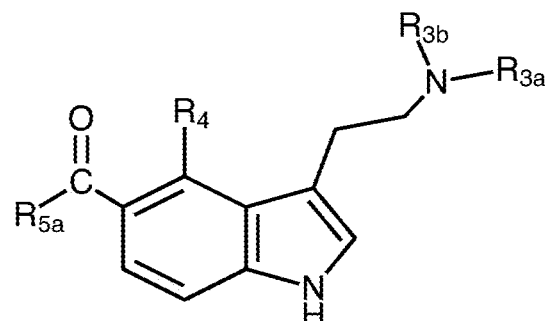
Figure 3G:
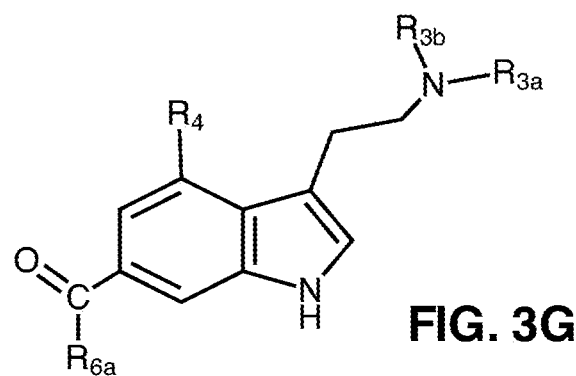
Figure 3H:
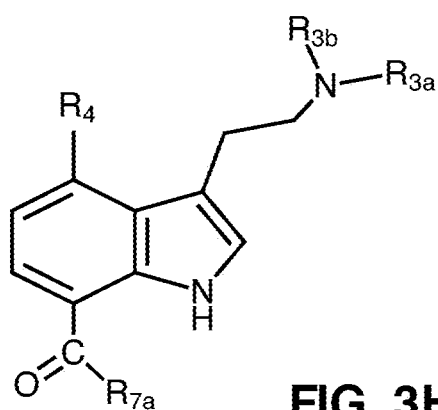

In a further aspect hereof, the non-carboxylated groups $R_2$, $R_5$, $R_6$, or $R_7$ can be a hydrogen atom, an alkyl group or O-alkyl group. Referring now to FIGS. 3A-3D, examples of carboxylated psilocybin derivatives in accordance herewith, wherein one of $R_2$, $R_5$, $R_6$, or $R_7$ are carboxylated, and the non-carboxylated groups $R_2$, $R_5$, $R_6$, or $R_7$ are hydrogen atoms are: the 2-carboxyl-psilocybin derivative compound depicted in FIG. 3A, the 5-carboxyl-psilocybin derivative depicted in FIG. 3B, the 6-carboxyl-psilocybin derivative depicted in FIG. 3C, the 7-carboxyl-psilocybin derivative depicted in FIG. 3D, Referring now to FIGS. 3E-3H, examples of carboxylated psilocybin derivatives in accordance herewith, wherein one of $R_2$, $R_5$, $R_6$, or $R_7$ are carboxylated, and the non-carboxylated groups $R_2$, $R_5$, $R_6$, or $R_7$ are hydrogen atoms are: the 2-OH-substituted carboxyl-psilocybin derivative compound depicted in FIG. 3E, the 5-OH-substituted carboxyl-psilocybin derivative depicted in FIG. 3F, the 6-OH-substituted carboxyl-psilocybin derivative depicted in FIG. 3G, and the 7-OH-substituted carboxyl-psilocybin derivative depicted in FIG. 3H. It is noted that in FIGS. 3E-3H, $R_{2a}$, $R_{5a}$, $R_{6a}$, and $R_{7a}$, can each be independently selected from an —OR' group, wherein R' is an alkyl group or an aryl group, to thereby form an ester.

Figure 5A:
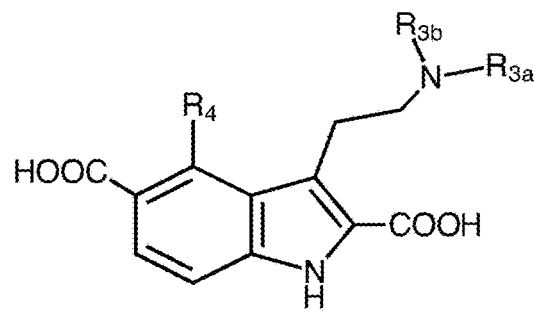
Figure 5B:
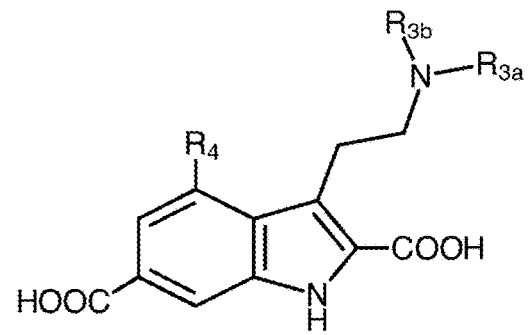
Figure 5C:
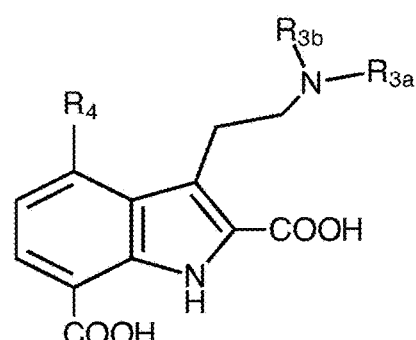
Figure 5D:
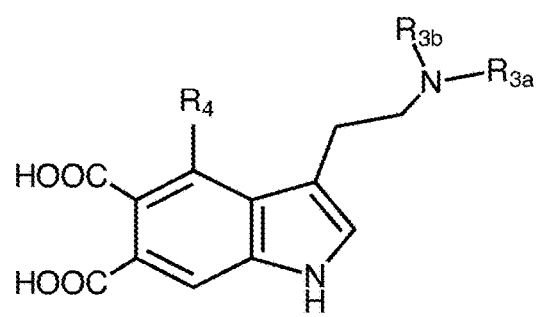
Figure 5E:
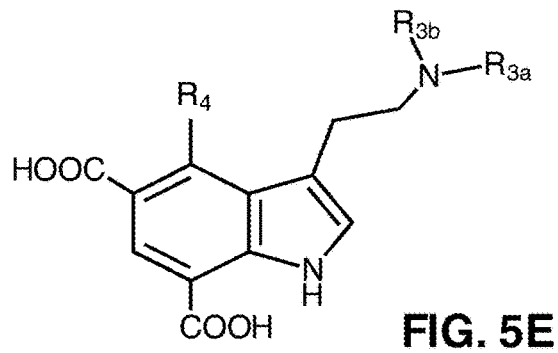
Figure 5F:
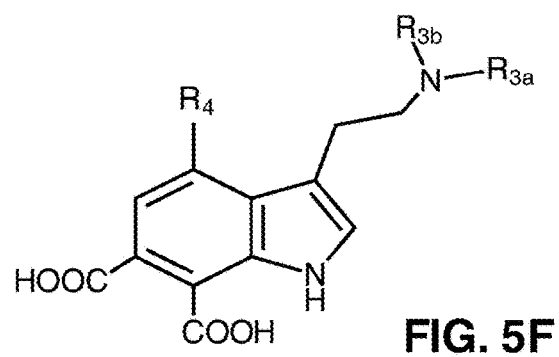

Referring now to FIGS. 5A-5F, examples of carboxylated psilocybin derivatives in accordance herewith, wherein two of $R_2$, $R_5$, $R_6$, or $R_7$ are carboxylated, and the non-carboxylated groups $R_2$, $R_5$, $R_6$, or $R_7$ are hydrogen atoms are: the 2,5-di-carboxyl-psilocybin derivative compound depicted in FIG. 5A, the 2,6-di-carboxyl-psilocybin derivative depicted in FIG. 5B, the 2,7-di-carboxyl-psilocybin derivative depicted in FIG. 5C, the 5,6-di-carboxyl-psilocybin derivative depicted in FIG. 5D, the 5,7-di-carboxyl-psilocybin derivative depicted in FIG. 5E, and the 6,7-di-carboxyl-psilocybin derivative depicted in FIG. 5F.

Figure 5G:
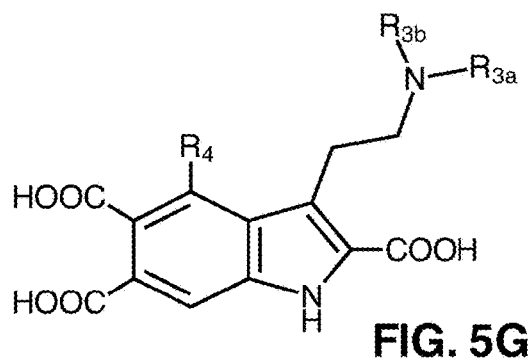
Figure 5H:
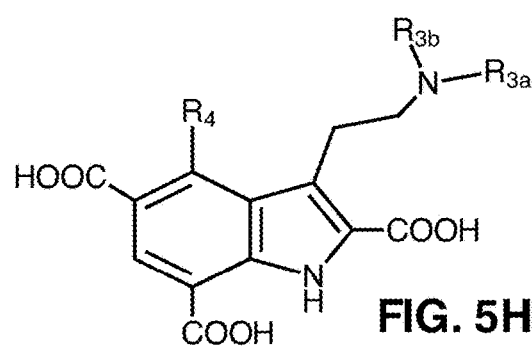
Figure 5I:
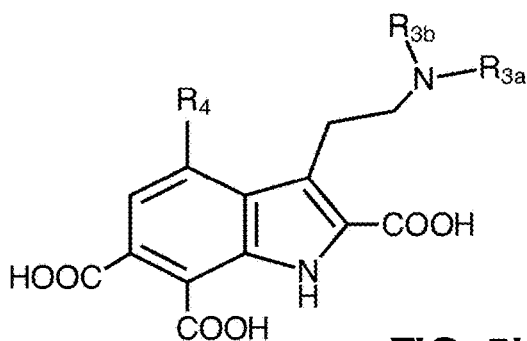
Figure 5J:
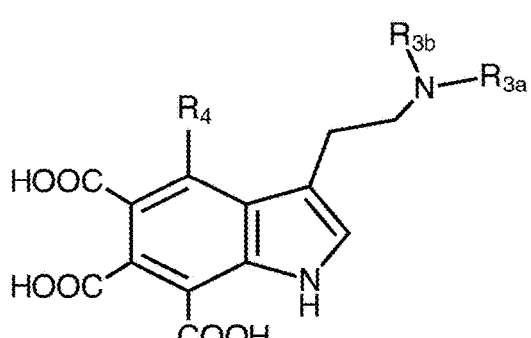

Referring now to FIGS. 5G-5J, examples of carboxylated psilocybin derivatives in accordance herewith, wherein three of $R_2$, $R_5$, $R_6$, or $R_7$ are carboxylated, and the non-carboxylated groups $R_2$, $R_5$, $R_6$, or $R_7$ are hydrogen atoms are: the 2,5,6-tri-carboxyl-psilocybin derivative compound depicted in FIG. 5G, the 2,57-tri-carboxyl-psilocybin derivative depicted in FIG. 5H, the 2,6,7-tri-carboxyl-psilocybin derivative depicted in FIG. 5I, and the 5,6,7-tri-carboxyl-psilocybin derivative depicted in FIG. 5J.

Figure 5K:
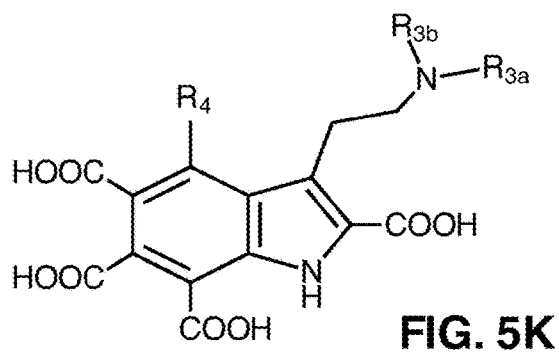

Referring now to FIG. 5K an example of a carboxylated psilocybin derivatives in accordance herewith, wherein all four of $R_2$, $R_5$, $R_6$, or $R_7$ are carboxylated is the 2,5,6,7-tetra-carboxyl-psilocybin derivative depicted in FIG. 4K.

Figure 5L:
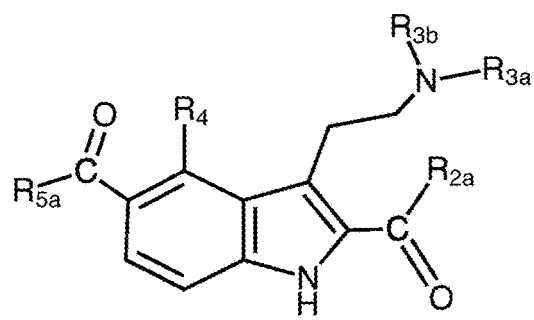
Figure 5M:
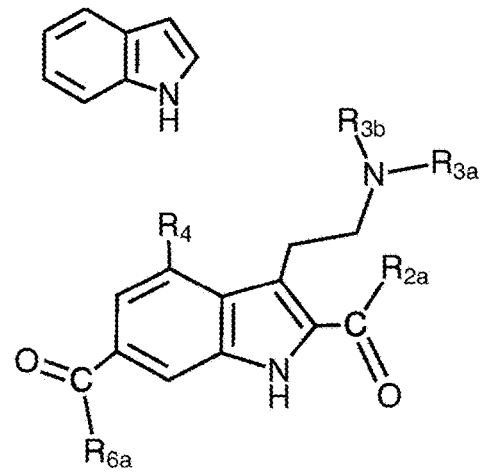
Figure 5N:
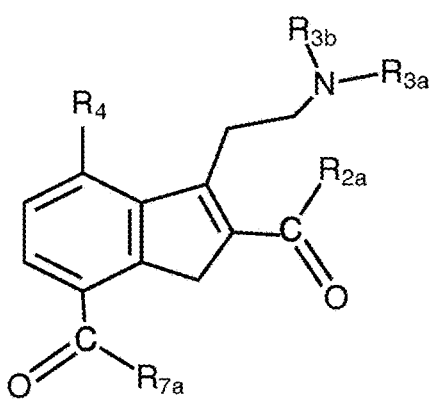
Figure 5O:
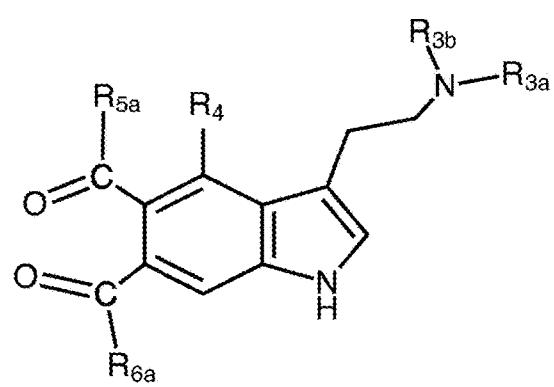
Figure 5P:
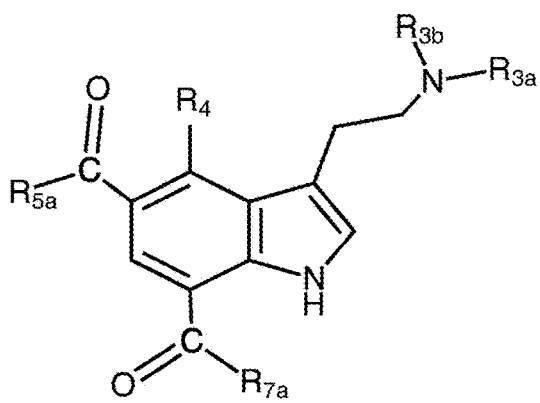
Figure 5Q:
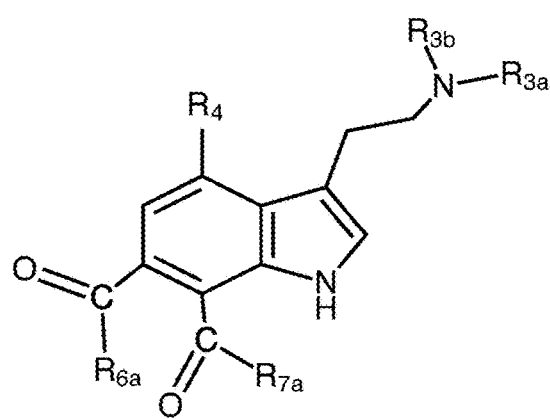

Referring now to FIGS. 5L-5Q, examples of carboxylated psilocybin derivatives in accordance herewith, wherein two of $R_2$, $R_5$, $R_6$, or $R_7$ are carboxylated, and the non-carboxylated groups $R_2$, $R_5$, $R_6$, or $R_7$ are hydrogen atoms are: the 2-OH,5-OH-di-substituted-carboxyl-psilocybin derivative compound depicted in FIG. 5L, the 2-OH,6-OH-di-substituted-carboxyl-psilocybin derivative depicted in FIG. 5M, the 2-OH,7-OH-di-substituted-carboxyl-psilocybin derivative depicted in FIG. 5N, the 5-OH,6-OH-di-substituted-carboxyl-psilocybin derivative depicted in FIG. 5O, the 5-OH,7-OH-di-substituted-carboxyl-psilocybin derivative depicted in FIG. 5P, and the 6-OH—,7-OH-di-substituted-carboxyl-psilocybin derivative depicted in FIG. 5Q. As hereinbefore noted, the substituents may be an —OR' group, wherein R' is an alkyl group or an aryl group, to thereby form an ester. Thus, by way of example only, in the 5-OH,6-OH-di-substituted-carboxyl-psilocybin derivative depicted in FIG. 5O $R_{5a}$, or $R_{6a}$, can be an —OR' group, wherein R' is an alkyl group or an aryl group, to thereby form an ester, wherein when $R_{5a}$, or $R_{6a}$ are not an —OR' group.

Figure 5R:
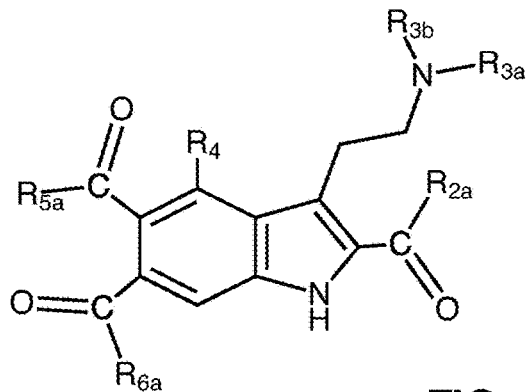
Figure 5S:
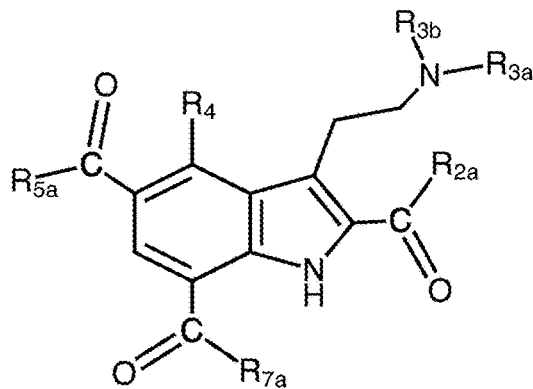
Figure 5T:
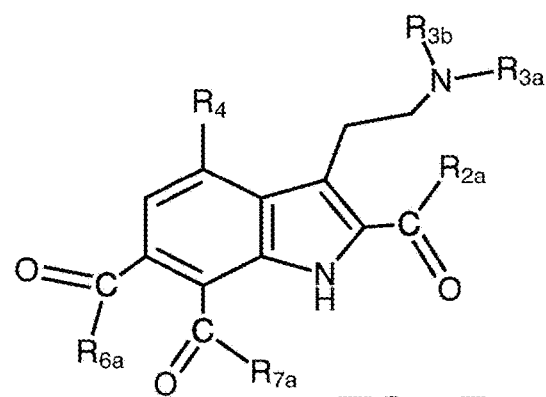
Figure 5U:
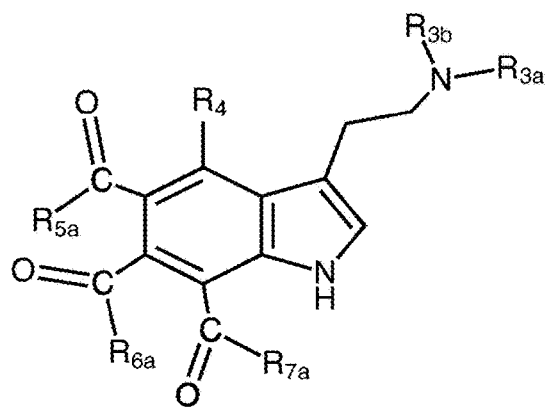
Figure 5V:
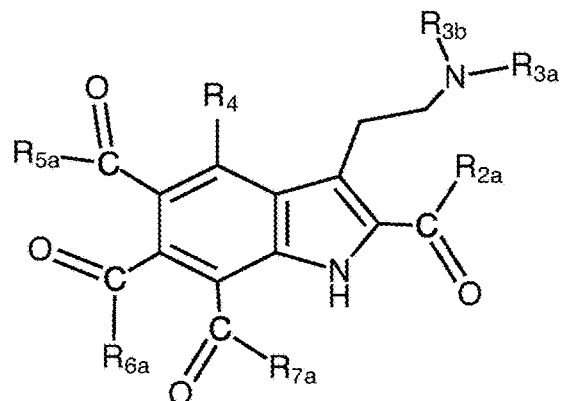
Figure 5W:
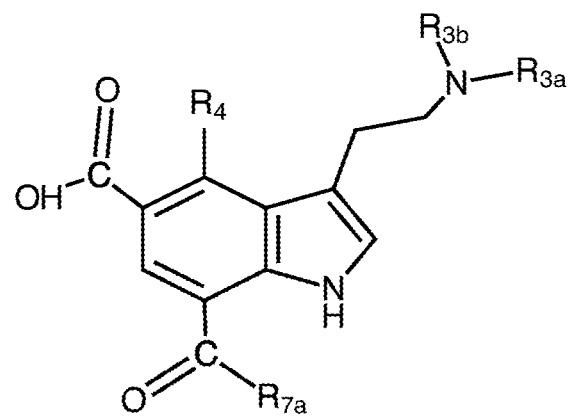
Figure 5X:
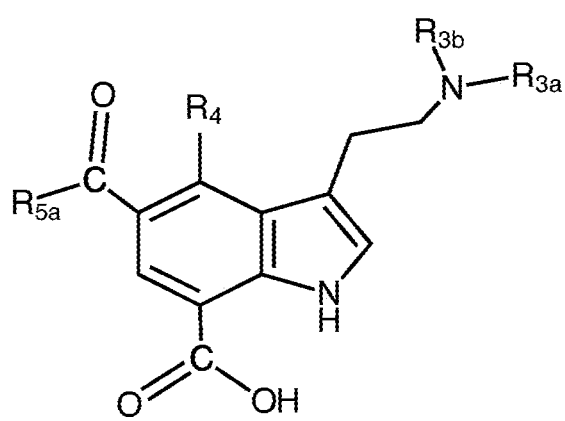

Referring next to FIGS. 5W-5X, it is noted that, in other embodiments, instead of being di-substituted, only one of the carboxylated groups may be a carboxylic acid derivative while the other carboxylated group is a carboxyl group. Thus, for example, referring to FIG. 5W, in such embodiments, only the $C_7$ carboxyl group is carboxylic acid derivative, while the $C_5$ carboxyl group is a non-substituted carboxyl group, or conversely, as shown in in FIG. 5X, only the $C_5$ carboxyl group may be carboxylic acid derivative, while the $C_7$ carboxyl group is a non-substituted carboxyl group. It is to be understood that any and all embodiments including di-carboxylated psilocybin derivatives include embodiments wherein none, one or two of the carboxyl groups are carboxylic acid derivative. As hereinbefore noted, the substituents may be an —OR' group, wherein R' is an alkyl group or an aryl group, to thereby form an ester.

Referring now to FIGS. 5R-5U, examples of carboxylated psilocybin derivatives in accordance herewith, wherein three of $R_2$, $R_5$, $R_6$, or $R_7$ are carboxylated, and the non-carboxylated groups $R_2$, $R_5$, $R_6$, or $R_7$ are hydrogen atoms are: the 2-OH,5-OH,6-OH-tri-substituted-carboxyl-psilocybin derivative compound depicted in FIG. 5R, the 2-OH,5-OH,7-OH-tri-substituted-carboxyl-psilocybin derivative depicted in FIG. 5S, the 2-OH,6-OH,7-OH-tri-substituted carboxyl-psilocybin derivative depicted in FIG. 5T, and the 5-OH,6-OH,7-OH-tri-substituted-carboxyl-psilocybin derivative depicted in FIG. 5U. As hereinbefore noted, the substituents may be an —OR' group, wherein R' is an alkyl group or an aryl group, to thereby form an ester. Thus, by way of example only, in the 5-OH,6-OH,7-OH-tri-substituted-carboxyl-psilocybin derivative depicted in FIG. 4U, $R_{5a}$, $R_{6a}$, or $R_{7a}$ can be an —OR' group, wherein R' is an alkyl group or an aryl group, to thereby form an ester, wherein when $R_{5a}$, $R_{6a}$ or $R_{7a}$ are not an —OR' group.

it is noted that, in other embodiments, instead of being tri-substituted, only one or two of the carboxylated groups may be a carboxylic acid derivative group while the non-OH substituted carboxyl groups are a carboxyl group. Thus, for example, only the $C_7$ carboxyl group can be carboxylic acid derivative, while the $C_5$ and $C_2$ carboxyl groups are non-substituted carboxyl groups. It is to be understood that included herein are any and all embodiments comprising tri-carboxylated psilocybin derivatives, wherein none, one, two or three of the carboxyl groups are carboxylic acid derivatives. As hereinbefore noted, the substituents may be an —OR' group.

Referring now to FIG. 5V, an example of a carboxylated psilocybin derivative in accordance herewith, wherein all four of $R_2$, $R_5$, $R_6$, or $R_7$ are carboxylated is the 2-OH,5-OH,6-OH,7-OH-tetra-substituted-carboxyl-psilocybin derivative depicted in FIG. 5V. As hereinbefore noted, the substituents may be an —OR' group, wherein R' is an alkyl group or an aryl group, to thereby form an ester. Thus, by way of example only, in the 2-OH,5-OH,6-OH,7-OH-tetra-substituted-carboxyl-psilocybin derivative depicted in FIG. 5V, $R_{2a}$, $R_{5a}$, $R_{6a}$, or $R_{7a}$ can be an —OR' group, wherein R' is an alkyl group or an aryl group, to thereby form an ester. It is noted that, in other embodiments, instead of being tetra-substituted, only one or two or three of the carboxylated groups may be a carboxylic acid derivative while the non-OH substituted carboxyl groups are a carboxyl group. Thus, for example, only the $C_7$ carboxyl group can be carboxylic acid derivative, while the $C_6$, $C_5$ and $C_2$ carboxyl groups are non-substituted carboxyl groups. It is to be understood that included herein are any and all embodiments comprising tetra-carboxylated psilocybin derivatives, wherein none, one, two, three or four of the carboxyl groups are carboxylic acid derivatives. As hereinbefore noted, the substituents may be an —OR' group, wherein R' is an alkyl group or an aryl group, to thereby form an ester.

In a further aspect, $R_4$, can be an O-alkyl group. Referring now to FIGS. 6A, 6B, 7A, 7B, 8A, and 8B, examples of carboxylated psilocybin derivatives in accordance herewith, wherein $R_5$, and/or $R_7$ are carboxyl groups carboxyl groups and $R_4$ is an O-alkyl group are: the 4-O-methyl-5-carboxyl-psilocybin derivative depicted in FIG. 6A, the 4-O-ethyl-5-carboxyl-psilocybin derivative depicted in FIG. 6B, the 4-O-methyl-7-carboxyl-psilocybin derivative depicted in FIG. 7A, the 4-O-ethyl-7-carboxyl-psilocybin derivative depicted in FIG. 7B, the 4-O-methyl-5,7-di-carboxyl-psilocybin derivative depicted in FIG. 8A, the 4-O-ethyl-5,7-di-carboxyl-psilocybin derivative depicted in FIG. 8B. It is noted that in these specific examples only 5-carboxyl, 7-carboxyl, and 5,7-di-carboxyl-4-O-alkyl psilocybin derivatives are shown. Further examples of O-alkyl psilocybin derivatives included herein are any and all O-alkyl psilocybin derivatives which may be selected by referring to the chemical formulas shown in FIGS. 3A-3D and FIGS. 5A-5K, wherein $R_4$ is an O-alkyl group. It will thus be clearly understood that FIGS. 6A, 6B, 7A, 7B, 8A, and 8B represent examples only of carboxylated psilocybin derivatives having chemical formula (I) wherein non-carboxylated groups $R_2$, $R_5$, $R_6$, or $R_7$ are a hydrogen atom. Other carboxylated psilocybin derivatives wherein non-carboxylated groups $R_2$, $R_5$, $R_6$, or $R_7$ are a hydrogen atom can readily be selected, and thus are included in the O-alkylated carboxylated psilocybin derivatives compounds of the present disclosure.

It is noted that the example carboxylated psilocybin derivatives shown in FIGS. 6A, 6B, 7A, 7B, 8A, and 8B are carboxylated psilocybin derivatives compounds by virtue of their carboxyl groups. Considering, FIGS. 6A, 6B, 7A, 7B, 8A, and 8D in conjunction with FIGS. 3E-3H and FIGS. 5L-5X, it is noted, and it will be clear that, in other embodiments, included herein are, further, carboxylated psilocybin derivatives wherein instead of a carboxyl group the psilocybin derivative possesses at least one carboxylic acid derivative, wherein the substituents may be an —OR' group, wherein R' is an alkyl group or an aryl group, to thereby form an ester.

In a further aspect, $R_4$, can be an O-acyl group. Referring now to FIGS. 6C, 6D, 7C, 7D, 8C, and 8D, examples of carboxylated psilocybin derivatives in accordance herewith, wherein $R_5$, and/or $R_7$ are carboxyl groups and $R_4$ is an O-acyl group are: the 4-acetyl-5-carboxyl-psilocybin derivative depicted in FIG. 6C, the 4-propanoyl-5-carboxyl-psilocybin derivative depicted in FIG. 6D, the 4-acetyl-7-carboxyl-psilocybin derivative depicted in FIG. 7C, the 4-propanoyl-7-carboxyl-psilocybin derivative depicted in FIG. 7D, the 4-acetyl-5,7-di-carboxyl-psilocybin derivative depicted in FIG. 8C, the 4-propanoyl-5,7-di-carboxyl-psilocybin derivative depicted in FIG. 8D. It is noted that in these specific examples only 5-carboxyl, 7-carboxyl, and 5,7-di-O-acyl psilocybin derivatives are shown. Further examples of O-acyl psilocybin derivatives included herein are any and all O-acyl psilocybin derivatives which may be selected by referring to the chemical formulas shown in FIGS. 3A-3D and FIGS. 5A-5K, wherein $R_4$ is an O-acyl group. It will thus be clearly understood that FIGS. 6C, 6D, 7C, 7D, 8C, and 8D represent examples only of O-acylated psilocybin derivatives having chemical formula (I) wherein non-carboxylated groups $R_2$, $R_5$, $R_6$, or $R_7$ are a hydrogen atom. Other carboxylated psilocybin derivatives wherein non-carboxylated groups $R_2$, $R_5$, $R_6$, or $R_7$ are a hydrogen atom can readily be selected, and thus are included in the carboxylated O-acylated psilocybin derivatives compounds of the present disclosure.

It is noted that the example carboxylated psilocybin derivatives shown in FIGS. 6C, 6D, 7C, 7D, 8C, and 8D are carboxylated psilocybin derivatives compounds by virtue of their carboxyl groups. Considering, FIGS. 6C, 6D, 7C, 7D, 8C, and 8D in conjunction with FIGS. 3E-3H and FIGS. 5L-5X, it is noted, and it will be clear that, in other embodiments, included herein are, further, carboxylated psilocybin derivatives wherein instead of a carboxyl group the psilocybin derivative possesses at least one carboxylic acid derivative, wherein the substituents may be an —OR' group, wherein R' is an alkyl group or an aryl group, to thereby form an ester.

In a further aspect, $R_4$, can be a hydroxy group. Referring now to FIGS. 6E, 7E, and 8E examples of carboxylated psilocybin derivatives in accordance herewith, wherein $R_5$, and/or $R_7$ are carboxyl groups and are $R_4$ is a hydroxy group are: the 4-hydroxy-5-carboxyl-psilocybin derivative depicted in FIG. 6E, the 4-hydroxy-7-carboxyl-psilocybin derivative depicted in FIG. 7E, and the 4-hydroxy-5,7-di-carboxyl-psilocybin derivative depicted in FIG. 8E, It is noted that in these specific examples only 5-carboxyl, 7-carboxyl, and 5,7-di-hydroxy-psilocybin derivatives are shown. Further examples of hydroxy-psilocybin derivatives included herein are any and all hydroxy-psilocybin derivatives which may be selected by referring to the chemical formulas shown in FIGS. 3A-3D and FIGS. 5A-5K, wherein $R_4$ is a hydroxy group. It will thus be clearly understood that FIGS. 6E, 7E, and 8E represent examples only of hydroxy psilocybin derivatives having chemical formula (I) wherein non-carboxylated groups $R_2$, $R_5$, $R_6$, or $R_7$ are a hydrogen atom. Other carboxylated psilocybin derivatives wherein non-carboxylated groups $R_2$, $R_5$, $R_6$, or $R_7$ are a hydrogen atom can readily be selected, and thus are included in the carboxylated hydroxy psilocybin derivatives compounds of the present disclosure.

It is noted that the example carboxylated psilocybin derivatives shown in FIGS. 6E, 7E, and 8E are carboxylated psilocybin derivatives compounds by virtue of their carboxyl groups. Considering, FIGS. 6E, 7E and 8E in conjunction with FIGS. 3E-3H and FIGS. 5L-5X, it is noted, and it will be clear that, in other embodiments, included herein are, further, carboxylated psilocybin derivatives wherein instead of a carboxyl group the psilocybin derivative possesses at least one carboxylic acid derivative, wherein the substituents may be an —OR' group, wherein R' is an alkyl group or an aryl group, to thereby form an ester.

Figure 6F:
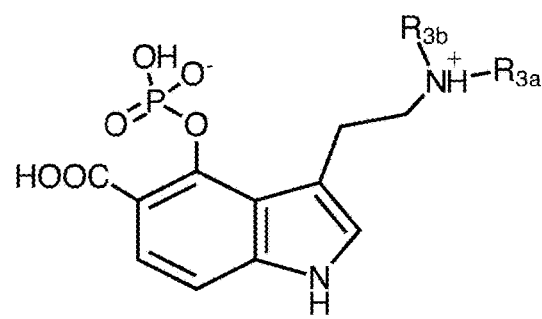

In a further aspect, $R_4$, can be a phosphate group. Referring now to FIGS. 6F, 7F, and 8F, examples of carboxylated psilocybin derivatives in accordance herewith, wherein $R_5$, and/or $R_7$ are carboxyl groups and are $R_4$ is a phosphate group are: the 4-phosphate-5-carboxyl-psilocybin derivative depicted in FIG. 6F, the 4-phosphate-7-carboxyl-psilocybin derivative depicted in FIG. 7F, and the 4-phosphate-5,7-carboxyl-psilocybin derivative depicted in FIG. 8F, It is noted that in these specific examples only 5-carboxyl, 7-carboxyl, and 5,7-di-phosphate-psilocybin derivatives are shown. Further examples of phosphate-psilocybin derivatives included herein are any and all phosphate-psilocybin derivatives which may be selected by referring to the chemical formulas shown in FIGS. 3A-3D and FIGS. 5A-5K, wherein $R_4$ is a phosphate group. It will thus be clearly understood that FIGS. 6F, 7F, and 8F represent examples only of phosphate psilocybin derivatives having chemical formula (I) wherein non-carboxylated groups $R_2$, $R_5$, $R_6$, or $R_7$ are a hydrogen atom. Other carboxylated psilocybin derivatives wherein non-carboxylated groups $R_2$, $R_5$, $R_6$, or $R_7$ are a hydrogen atom can readily be selected, and thus are included in the carboxylated phosphate psilocybin derivatives compounds of the present disclosure.

It is noted that the example carboxylated psilocybin derivatives shown in FIGS. 6F, 7F, and 8F are carboxylated psilocybin derivatives compounds by virtue of their carboxyl groups. Considering, FIGS. 6F, 7F and 8F in conjunction with FIGS. 3E-3H and FIGS. 5L-5X, it is noted, and it will be clear that, in other embodiments, included herein are, further, carboxylated psilocybin derivatives wherein instead of a carboxyl group the psilocybin derivative possesses at least one carboxylic acid derivative, wherein the substituents may be an —OR' group, wherein R' is an alkyl group or an aryl group, to thereby form an ester.

Figure 6G:
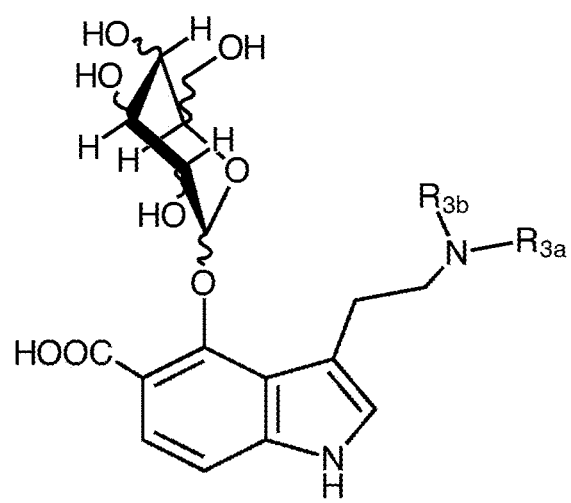

In a further aspect, $R_4$, can be a glycosyloxy group. Referring now to FIGS. 6G, 7G, and 8G examples of carboxylated psilocybin derivatives in accordance herewith, wherein $R_5$, and/or $R_7$ are carboxyl groups and are $R_4$ is a glycosyloxy group are: the 4-O-glycosyl-5-carboxyl-psilocybin derivative depicted in FIG. 6G, the 4-O-glycosyl-7-carboxyl-psilocybin derivative depicted in FIG. 7G, and the 4-O-glycosyl-5,7-di-carboxyl-psilocybin derivative depicted in FIG. 8G, It is noted that in these specific examples only 5-carboxyl, 7-carboxyl, and 5,7-di-carboxyl-psilocybin derivatives are shown. Further examples of glycosyl-psilocybin derivatives included herein are any and all glycosyl-psilocybin derivatives which may be selected by referring to the chemical formulas shown in FIGS. 3A-3D and FIGS. 5A-5K, wherein $R_4$ is a glycosyloxy group. It will thus be clearly understood that FIGS. 6G, 7G, and 8G represent examples only of glycosyloxy psilocybin derivatives having chemical formula (I) wherein non-carboxylated groups $R_2$, $R_5$, $R_6$, or $R_7$ are a hydrogen atom. Other carboxylated psilocybin derivatives wherein non-carboxylated groups $R_2$, $R_5$, $R_6$, or $R_7$ are a hydrogen atom can readily be selected, and thus are included in the carboxylated glycosyloxy psilocybin derivatives compounds of the present disclosure.

It is noted that the example carboxylated psilocybin derivatives shown in FIGS. 6G, 7G, and 8G are carboxylated psilocybin derivatives compounds by virtue of their carboxyl groups. Considering, FIGS. 6G, 7G and 8G in conjunction with FIGS. 3E-3H and FIGS. 5L-5X, it is noted, and it will be clear that, in other embodiments, included herein are, further, carboxylated psilocybin derivatives wherein instead of a carboxyl group the psilocybin derivative possesses at least one carboxylic acid derivative, wherein the substituents may be an —OR' group, wherein R' is an alkyl group or an aryl group, to thereby form an ester.

Figure 6H:
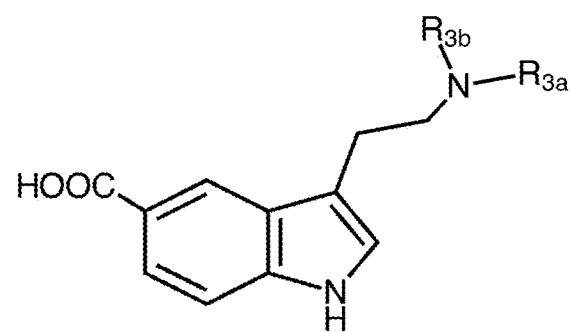

In a further aspect, $R_4$, can be a hydrogen atom. Referring now to FIGS. 6H, 7H, and 8H examples of carboxylated psilocybin derivatives in accordance herewith, wherein $R_5$, and/or $R_7$ are carboxyl groups and are $R_4$ is a hydrogen atom are: the 5-carboxyl-psilocybin derivative depicted in FIG. 6H, the 7-carboxyl-psilocybin derivative depicted in FIG. 7H, and the 5,7-di-carboxyl-psilocybin derivative depicted in FIG. 8H, It is noted that in these specific examples only 5-carboxyl, 7-carboxyl, and 5,7-di-carboxyl-hydro-psilocybin derivatives are shown. Further examples of hydro-psilocybin derivatives included herein are any and all hydro-psilocybin derivatives which may be selected by referring to the chemical formulas shown in FIGS. 3A-3D and FIGS. 5A-5K, wherein $R_4$ is a hydrogen atom. It will thus be clearly understood that FIGS. 6H, 7H, and 8H represent examples only of hydro psilocybin derivatives having chemical formula (I) wherein non-carboxylated groups $R_2$, $R_5$, $R_6$, or $R_7$ are a hydrogen atom. Other carboxylated psilocybin derivatives wherein non-carboxylated groups $R_2$, $R_5$, $R_6$, or $R_7$ are a hydrogen atom can readily be selected, and thus are included in the carboxylated hydro psilocybin derivatives compounds of the present disclosure.

It is noted that the example carboxylated psilocybin derivatives shown in FIGS. 6H, 7H, and 8H are carboxylated psilocybin derivatives compounds by virtue of their carboxyl groups. Considering, FIGS. 6H, 7H and 8H in conjunction with FIGS. 3E-3H and FIGS. 5L-5X, it is noted, and it will be clear that, in other embodiments, included herein are, further, carboxylated psilocybin derivatives wherein instead of a carboxyl group the psilocybin derivative possesses at least one carboxylic acid derivative, wherein the substituents may be an —OR' group, wherein R' is an alkyl group or an aryl group, to thereby form an ester.

Furthermore, in one embodiment, a carboxylated psilocybin derivative according to the present disclosure can be a chemical compound having the formula (VI), (VII) or (VIII):

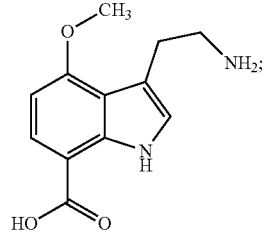

(VI)

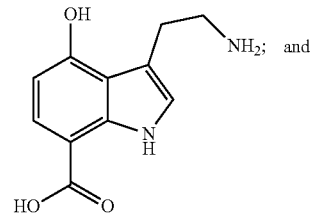

(VII)

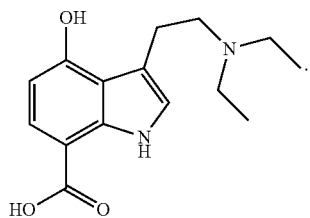

(VIII)

In one embodiment, the alkyl groups (including O-alkyl, and the alkyl groups present in acyl and O-acyl) in any of the definitions of the Formulas of the disclosure is $C_1$-$C_{20}$-alkyl. In another embodiment, the alkyl group is $C_1$-$C_{10}$-alkyl. In another embodiment, the alkyl group is $C_1$-$C_6$-alkyl. In another embodiment, the alkyl group is methyl, ethyl, propyl, butyl or pentyl.

In one embodiment, the aryl groups in any of the definitions of the Formulas of the disclosure is optionally substituted $C_6$-$C_{14}$-aryl. In another embodiment, the aryl group is optionally substituted $C_6$-$C_{10}$-aryl, or phenyl. In another embodiment, the aryl group is phenyl, naphthyl, tetrahydronaphthyl, phenanthrenyl, biphenylenyl, indanyl, or indenyl and the like.

Furthermore, it is noted that the carboxylated psilocybin derivatives of the present disclosure include salts thereof, including pharmaceutically acceptable salts. Thus, the nitrogen atom of the ethyl-amino group extending in turn from the $C_3$ atom may be protonated, and the positive charge may be balanced by, for example, chloride or sulfate ions, to thereby form a chloride salt or a sulfate salt. Furthermore, in compounds wherein $R_4$ is a phosphate group, the phosphate group may be de-protonated, and the negative charge may be balanced by, for example, sodium ions or potassium ions, to thereby form a sodium salt or a potassium salt.

Furthermore, it is noted that when $R_4$ is a phosphate group, the term carboxylated psilocybin derivative also includes compounds having the formula (V):

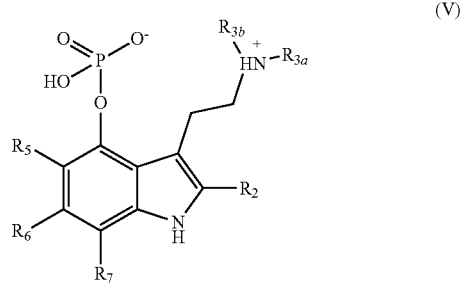

(V)

wherein at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group. Further included are salts of carboxylated psilocybins having the formula (V), such as a sodium salt, a potassium salt etc.

Thus, to briefly recap, the present disclosure provides carboxylated psilocybin derivatives. The disclosure provides, in particular, a chemical compound having the formula (I):

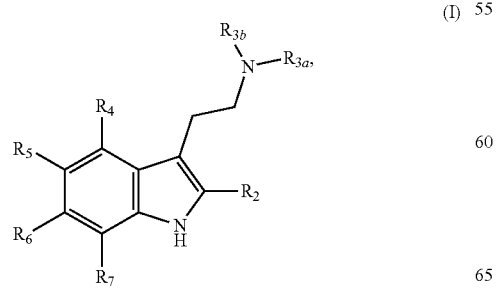

(I)

wherein, at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, an alkyl group, or O-alkyl group wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group.

In one embodiment, at least one of $R_2$, $R_4$, $R_5$, $R_6$, or $R_7$ is a carboxyl group or a carboxylic acid derivative, and wherein each non-carboxylated $R_2$, $R_5$, $R_6$, or $R_7$ is a hydrogen atom or a ($C_1$-$C_{20}$)-alkyl group or ($C_1$-$C_{20}$)—O-alkyl group. In another embodiment, each non-carboxylated $R_2$, $R_5$, $R_6$, or $R_7$ is a hydrogen atom, a methyl group, ethyl group, a propyl group, an O-methyl group, an O-ethyl group, or an O-propyl group.

In another embodiment, each non-carboxylated $R_2$, $R_5$, $R_6$, or $R_7$ is a hydrogen atom or a ($C_1$-$C_{10}$)-alkyl group or ($C_1$-$C_{10}$)—O-alkyl group. In another embodiment, each non-carboxylated $R_2$, $R_5$, $R_6$, or $R_7$ is a hydrogen atom, a methyl group, ethyl group, a propyl group, an O-methyl group, an O-ethyl group, or an O-propyl group.

In another embodiment, when $R_4$ is not carboxylated, $R_4$ is a hydrogen atom, a ($C_1$-$C_{20}$)-alkyl group or ($C_1$-$C_{20}$)—O-alkyl group, a hydroxy group, a glycosyloxy group, or a phosphate group. In another embodiment, when $R_4$ is not carboxylated, $R_4$ is a hydrogen atom, a ($C_1$-$C_{10}$)-alkyl group or ($C_1$-$C_{10}$)—O-alkyl group, a hydroxy group, a glycosyloxy group, or a phosphate group. In another embodiment, when $R_4$ is not carboxylated, $R_4$ is a hydrogen atom, a ($C_1$-$C_6$)-alkyl group or ($C_1$-$C_6$)—O-alkyl group, a hydroxy group, a glycosyloxy group, or a phosphate group. In another embodiment, when $R_4$ is not carboxylated, $R_4$ is a hydrogen atom, a methyl group, an ethyl group, a propyl group, a glycosyloxy group, a phosphate group, an O-methyl group, an O-ethyl group, or an O-propyl group.

In another embodiment, $R_{3A}$ and $R_{3B}$ are a hydrogen atom, a ($C_1$-$C_{20}$)-alkyl group, a ($C_6$-$C_{14}$)-aryl group, or a —C(=O)($C_1$-$C_{20}$)-alkyl group. In another embodiment, $R_{3A}$ and $R_{3B}$ are a hydrogen atom, a ($C_1$-$C_{10}$)-alkyl group, a ($C_6$-$C_{10}$)-aryl group, or a —C(=O)($C_1$-$C_{10}$)-alkyl group. In another embodiment, $R_{3A}$ and $R_{3B}$ are a hydrogen atom, a ($C_1$-$C_6$)-alkyl group, a phenyl group, or a —C(=O)($C_1$-$C_6$)-alkyl group. In another embodiment, $R_{3A}$ and $R_{3B}$ are a hydrogen atom, a methyl group, ethyl group, a propyl group, a phenyl group, —C(=O)—CH$_3$, —C(=O)—CH$_2$CH$_3$, or —C(=O)—CH$_2$CH$_2$CH$_3$.

In one embodiment of the disclosure, a chemical compound or salt thereof having formula (I) is included:

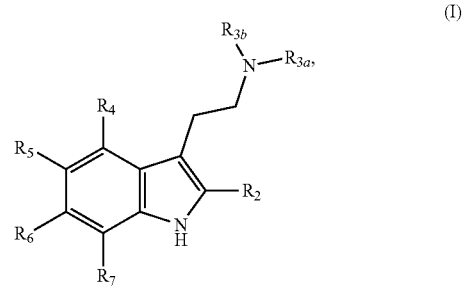

(I)

wherein $R_2$, $R_5$, $R_6$, and $R_7$ are independently or simultaneously H, an alkyl group, or O-alkyl group or a carboxy group or carboxylic acid derivative, $R_{3A}$ and $R_{3B}$ are each independently a hydrogen atom, an alkyl group, an aryl group, or an acyl group; and $R_4$ is hydrogen atom, alkyl group or O-alkyl group, a carboxy group or carboxylic acid derivative, a hydroxy group, a glycosyloxy group, or a phosphate group; wherein at least one of $R_2$, $R_4$, $R_5$, $R_6$, and $R_7$ is a carboxy group or carboxylic acid derivative.

In one embodiment, $R_2$, $R_5$, $R_6$, and $R_7$ are independently or simultaneously H, $(C_1-C_{20})$-alkyl group or $(C_1-C_{20})$—O-alkyl group or a carboxy group or carboxylic acid derivative. In one embodiment, $R_2$, $R_5$, $R_6$, and $R_7$ are independently or simultaneously H, $(C_1-C_{10})$-alkyl group or $(C_1-C_{10})$—O-alkyl group or a carboxy group or carboxylic acid derivative. In one embodiment, $R_2$, $R_5$, $R_6$, and $R_7$ are independently or simultaneously H, $(C_1-C_6)$-alkyl group or $(C_1-C_6)$—O-alkyl group or a carboxy group or carboxylic acid derivative. In one embodiment, $R_2$, $R_5$, $R_6$, and $R_7$ are independently or simultaneously H, methyl, ethyl, propyl, O-methyl, O-ethyl, O-propyl, or a carboxy group or carboxylic acid derivative.

In one embodiment, $R_7$ is a carboxy group or carboxylic acid derivative.

In one embodiment, $R_4$ is H, $(C_1-C_{20})$-alkyl group or $(C_1-C_{20})$—O-alkyl group, a carboxy group or carboxylic acid derivative, a glycosyloxy group, or a phosphate group. In one embodiment, $R_4$ is H, $(C_1-C_{10})$-alkyl group or $(C_1-C_{10})$—O-alkyl group, a carboxy group or carboxylic acid derivative, a glycosyloxy group, or a phosphate group. In one embodiment, $R_4$ is H, $(C_1-C_6)$-alkyl group or $(C_1-C_6)$—O-alkyl group, a glycosyloxy group, a hydroxy group, or a phosphate group. In one embodiment, $R_4$ is H, methyl, ethyl, propyl, O-methyl, O-ethyl, O-propyl, a carboxy group or carboxylic acid derivative, a glycosyloxy group, a hydroxy group, or a phosphate group.

In another embodiment, $R_{3A}$ and $R_{3B}$ are a hydrogen atom, a $(C_1-C_{20})$-alkyl group, a $(C_6-C_{14})$-aryl group, or a —C(=O)$(C_1-C_{20})$-alkyl group. In another embodiment, $R_{3A}$ and $R_{3B}$ are a hydrogen atom, a $(C_1-C_{10})$-alkyl group, a $(C_6-C_{10})$-aryl group, or a —C(=O)$(C_1-C_{10})$-alkyl group or O-alkyl group. In another embodiment, $R_{3A}$ and $R_{3B}$ are a hydrogen atom, a $(C_1-C_6)$-alkyl group, a phenyl group, or a —C(=O)$(C_1-C_6)$-alkyl group. In another embodiment, $R_{3A}$ and $R_{3B}$ are a hydrogen atom, a methyl group, an ethyl group, a propyl group, a phenyl group, —C(=O)—CH$_3$, —C(=O)—CH$_2$CH$_3$, or —C(=O)—CH$_2$CH$_2$CH$_3$.

The carboxylated psilocybin derivatives of the present disclosure may be used to prepare a pharmaceutical or recreational drug formulation. Thus in one embodiment, the present disclosure further provides in another aspect, pharmaceutical and recreational drug formulations comprising carboxylated psilocybin derivatives. Accordingly, in one aspect, the present disclosure provides in a further embodiment a pharmaceutical or recreational drug formulation comprising a chemical compound having the formula (I):

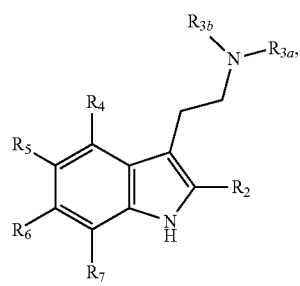

(I)

wherein, at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group, together with a diluent, carrier or excipient.

The dose when using the compounds of the present disclosure can vary within wide limits, and as is customary and is known to those of skill in the art, the dose can be tailored to the individual conditions in each individual case. The dose depends, for example, on the nature and severity of the illness to be treated, on the condition of the patient, on the compound employed or on whether an acute or chronic disease state is treated or prophylaxis is conducted, on the mode of delivery of the compound, or on whether further active compounds are administered in addition to the compounds of the present disclosure. Representative doses of the present invention include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to about 100 mg, about 0.001 mg to about 50 mg, and about 0.001 mg to about 25 mg. Representative doses of the present disclosure include, but are not limited to, about 0.0001 to about 1,000 mg, about 10 to about 160 mg, about 10 mg, about 20 mg, about 40 mg, about 80 mg or about 160 mg. Multiple doses may be administered during the day, especially when relatively large amounts are deemed to be needed, for example 2, 3 or 4, doses. Depending on the subject and as deemed appropriate from the patient's physician or care giver it may be necessary to deviate upward or downward from the doses described herein.

The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the carboxylated psilocybin compound together with an excipient. The term "excipient" as used herein means any ingredient other than the chemical compound of the disclosure. As will readily be appreciated by those of skill in art, the selection of excipient may depend on factors such as the particular mode of administration, the effect of the excipient on solubility of the chemical compounds of the present disclosure and methods for their preparation will be readily apparent to those skilled in the art. Such compositions and methods for their preparation may be found, for example, in "Remington's Pharmaceutical Sciences", 22$^{nd}$ Edition (Pharmaceutical Press and Philadelphia College of Pharmacy at the University of the Sciences, 2012).

The pharmaceutical and drug formulations comprising the carboxylated psilocybin derivatives of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nanoparticulates, gels, solid solutions, liposomal preparations, microencapsulated preparations, creams, films, ovules, suppositories, and sprays.

Liquid formulations include suspensions, solutions, syrups, and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally comprise surface active agents, such as sodium lauryl sulfate and polysorbate 80. When present, surface active agents may comprise from 0.2% (w/w) to 5% (w/w) of the tablet.

Tablets may further contain lubricants such as magnesium stearate, calcium stearate, zinc stearate, sodium stearyl fumarate, and mixtures of magnesium stearate with sodium lauryl sulphate. Lubricants generally comprise from 0.25% (w/w) to 10% (w/w), from 0.5% (w/w) to 3% (w/w) of the tablet.

In addition to the carboxylated psilocybin derivative, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1% (w/w) to 25% (w/w) or from 5% (w/w) to 20% (w/w) of the dosage form.

Other possible auxiliary ingredients include anti-oxidants, colourants, flavouring agents, preservatives, and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90% (w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1-Vol. 3, by CRC Press (2008).

The pharmaceutical and recreational drug formulations comprising the carboxylated psilocybin derivatives of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates and buffering agents (in one embodiment, to a pH of from 3 to 9), but, for some applications, they may be more suitably formulated as a sterile non-aqueous solution or as a dried form to be used in conjunction with a suitable vehicle such as sterile water.

Formulations comprising the carboxylated psilocybin derivatives of the present disclosure for parenteral administration may be formulated to be immediate and/or modified release. Modified release formulations include delayed-, sustained-, pulsed-, controlled-, targeted and programmed release. Thus the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The pharmaceutical or recreational drug formulations of the present disclosure also may be administered topically to the skin or mucosa, i.e., dermally or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T. M., 1999 J. Pharm. Sci, 88 (10), 955-958).

Other means of topical administration include delivery by electroporation, iontophoresis, phonophoresis, sonophoresis and microneedle or needle-free (e.g., Powderject™, Bioject™, etc.) injection.

Pharmaceutical and recreational drug formulations for inhalation or insufflation include solutions and suspensions in pharmaceutically acceptable, aqueous, or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally, or nasally, from devices that deliver the formulation in an appropriate manner.

In further embodiments, in which the carboxylated psilocybin derivative compounds of present disclosure are used as a recreational drug, the compounds may be included in compositions such as a food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

Thus it will be clear the carboxylated psilocybin derivative compounds may be used as a pharmaceutical or recreational drug. Accordingly, in another aspect the present disclosure provides, in at least one embodiment, a use of a chemical compound having the formula (I):

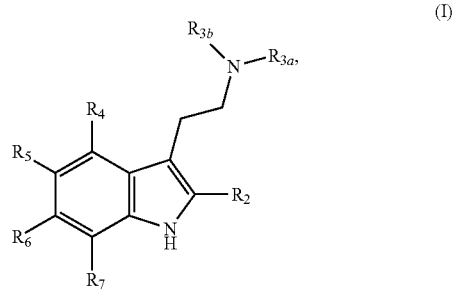

(I)

wherein, at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group, together with a diluent, carrier, or excipient as a pharmaceutical or recreational drug formulation.

The pharmaceutical formulations comprising the chemical compounds of the present disclosure may be used to treat a subject, and in particular to treat a psychiatric disorder in a subject. Accordingly, the present disclosure includes in a further embodiment, a method for treating a psychiatric disorder, the method comprising administering to a subject in need thereof a pharmaceutical formulation comprising a chemical compound having the formula (I):

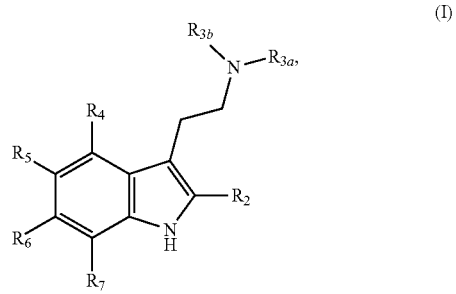

(I)

wherein, at least one of $R_2$, $R_5$, $R_6$, or $R_7$ is a carboxyl group or a carboxylic acid derivative, and wherein each non-carboxylated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group, together with a diluent, carrier or excipient.

Psychiatric disorders that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder, persistent depressive disorder (dysthymia), premenstrual dysphoric disorder, substance/medication-induced depressive disorder, postpartum depression, and depressive disorder caused by another medical condition, for example, psychiatric and existential distress within life-threatening cancer situations (ACS Pharmacol. Transl. Sci. 4: 553-562; J Psychiatr Res 137: 273-282); substance-related disorders, such as alcohol-related disorders, cannabis related disorders, inhalant-use related disorders, stimulant use disorders, and tobacco use disorders; neurocognitive disorders, such as delirium; schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder.

In an aspect, the compounds of the present disclosure may be used to be contacted with a $5\text{-HT}_{2A}$ receptor to thereby modulate the $5\text{-HT}_{2A}$ receptor. Such contacting includes bringing a compound of the present disclosure and $5\text{-HT}_{2A}$ receptor together under in vitro conditions, for example, by introducing the compounds in a sample containing a $5\text{-HT}_{2A}$ receptor, for example, a sample containing purified $5\text{-HT}_{2A}$ receptors, or a sample containing cells comprising $5\text{-HT}_{2A}$ receptors. In vitro conditions further include the conditions described in Example 1 hereof. Contacting further includes bringing a compound of the present disclosure and $5\text{-HT}_{2A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the $5\text{-HT}_{2A}$ receptor, the compound may activate the $5\text{-HT}_{2A}$ receptor or inhibit the $5\text{-HT}_{2A}$ receptor.

Thus, in a further aspect, the condition that may be treated in accordance herewith can be any $5\text{-HT}_{2A}$ receptor mediated disorder. Such disorders include, but are not limited to schizophrenia, psychotic disorder, attention deficit hyperactivity disorder, autism, and bipolar disorder.

In an aspect, the compounds of the present disclosure may be used to be contacted with a $5\text{-HT}_{1A}$ receptor to thereby modulate the $5\text{-HT}_{1A}$ receptor. Such contacting includes bringing a compound of the present disclosure and $5\text{-HT}_{1A}$ receptor together under in vitro conditions, for example, by introducing the compounds in a sample containing a $5\text{-HT}_{1A}$ receptor, for example, a sample containing purified 5-HT$_{1A}$ receptors, or a sample containing cells comprising 5-HT$_{1A}$ receptors. In vitro conditions further include the conditions described in Example 1 hereof. Contacting further includes bringing a compound of the present disclosure and 5-HT$_{1A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the 5-HT$_{2A}$ receptor, the compound may activate the 5-HT$_{1A}$ receptor or inhibit the 5-HT$_{1A}$ receptor.

Thus, in a further aspect, the condition that may be treated in accordance herewith can be any 5-HT$_{1A}$ receptor mediated disorder. Such disorders include, but are not limited to schizophrenia, psychotic disorder, attention deficit hyperactivity disorder, autism, and bipolar disorder.

Turning now to methods of making the carboxylated psilocybin derivatives of the present disclosure, it is initially noted that the carboxylated psilocybin derivatives of the present disclosure may be prepared in any suitable manner, including by any organic chemical synthesis methods, biosynthetic methods, or a combination thereof.

One suitable method of making the carboxylated psilocybin derivatives of the present disclosure initially involves selecting and obtaining or preparing a reactant psilocybin derivative compound and selecting and obtaining or preparing a compound selected from a carboxyl containing compound.

Suitable reactant psilocybin derivative compounds include compounds comprising an indole prototype structure (see: FIG. 2), including, for example, a chemical compound having formula (II)

(II)

wherein, at least one of $R_2$, $R_5$, $R_6$, or $R_7$ is a hydrogen atom, an alkyl group, O-alkyl group, or a halogen, wherein $R_4$ is an O-alkyl group, an O-acyl group, a hydroxy group, a phosphate group, a glycosyloxy group, or a hydrogen atom and wherein $R_{3A}$ and $R_{3B}$ are each independently a hydrogen atom, an alkyl group, acyl group or an aryl group. Reactant psilocybin derivative compound (II) comprises a plurality of compounds, some examples of which will next be described.

Figure 9A:
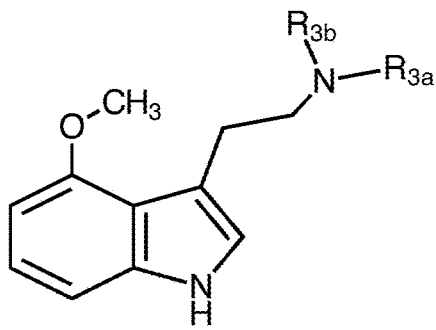
Figure 9B:
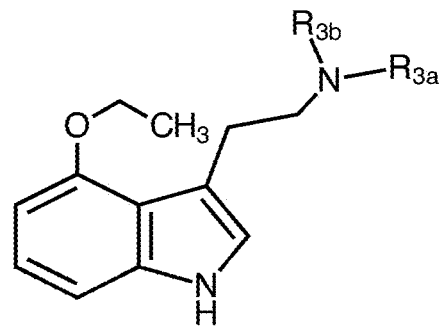

In one example embodiment, the reactant psilocybin derivative can be selected to be a chemical compound wherein $R_4$ is an O-alkyl group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIGS. 9A and 9B.

Figure 9C:
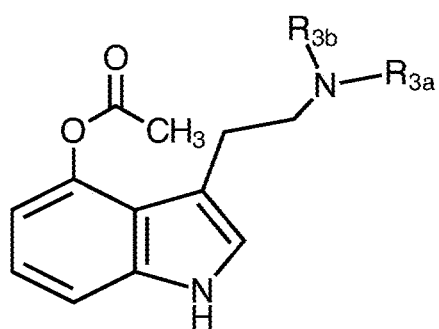
Figure 9D:
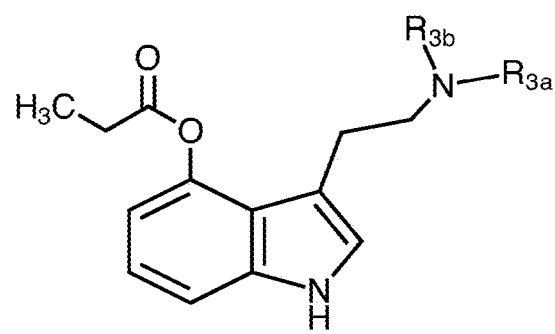

In one example embodiment, the reactant psilocybin derivative can be selected to be a chemical compound wherein $R_4$ is an O-acyl group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIGS. 9C and 9D.

Figure 9E:
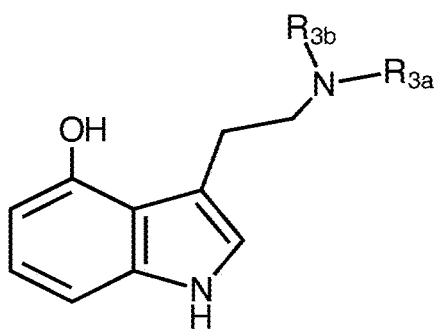

In one example embodiment, the reactant psilocybin derivative can be selected to be a chemical compound wherein $R_4$ is a hydroxyl group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIG. 9E.

Figure 9F:
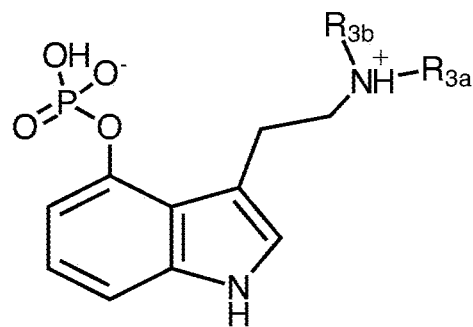

In one example embodiment, the reactant psilocybin derivative can be selected to be a chemical compound wherein $R_4$ is a phosphate group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIG. 9F.

Figure 9G:
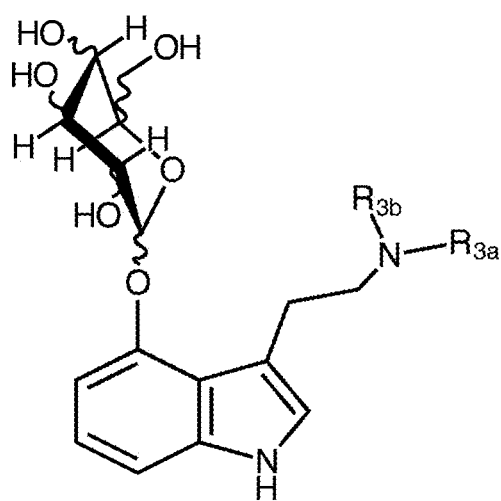

In one example embodiment, the reactant psilocybin derivative can be selected to be a chemical compound wherein $R_4$ is a glycosyloxy group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIG. 9G.

Figure 9H:
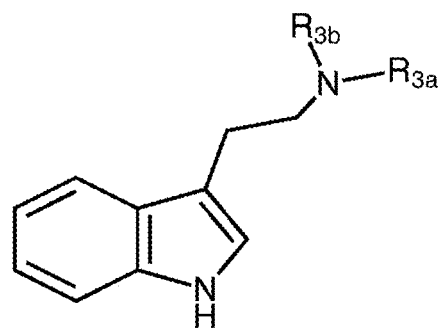

In one example embodiment, the reactant psilocybin derivative can be selected to be a chemical compound wherein $R_4$ is a hydrogen atom, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIG. 9H.

The reactant psilocybin derivative compounds may be provided in a more or less chemically pure form, for example, in the form of a psilocybin derivative preparation having a purity of at least about 95%, at least about 96%, at least about 97%, at least about 98%, at least about 99%, or at least 99.9%. The psilocybin derivative may be chemically synthesized, or obtained from a fine chemical manufacturer.

The carboxyl group containing compound may be provided in a more or less chemically pure form, for example, having a purity of at least about 95%, at least about 96%, at least about 97%, at least about 98%, at least about 99%, or at least 99.9%. The azido or nitro group containing compound may be synthesized or purified, or can be conveniently obtained from a fine chemical manufacturer.

Thus, initially, in an aspect hereof, a reactant psilocybin derivative is provided, and the reactant psilocybin derivative is employed to react in a chemical reaction resulting in the formation of a carboxylated psilocybin derivatives.

Figure 10A:
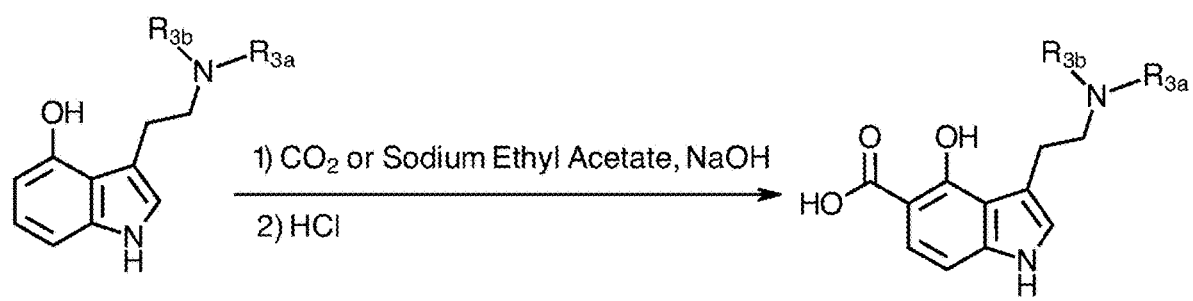
Figure 10B:
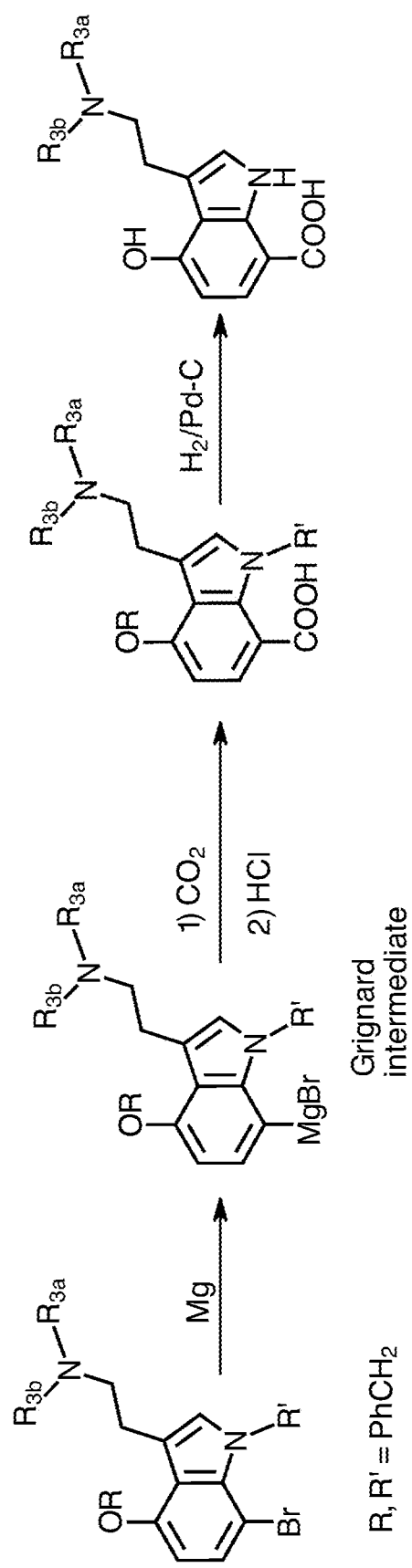
Figure 10C:
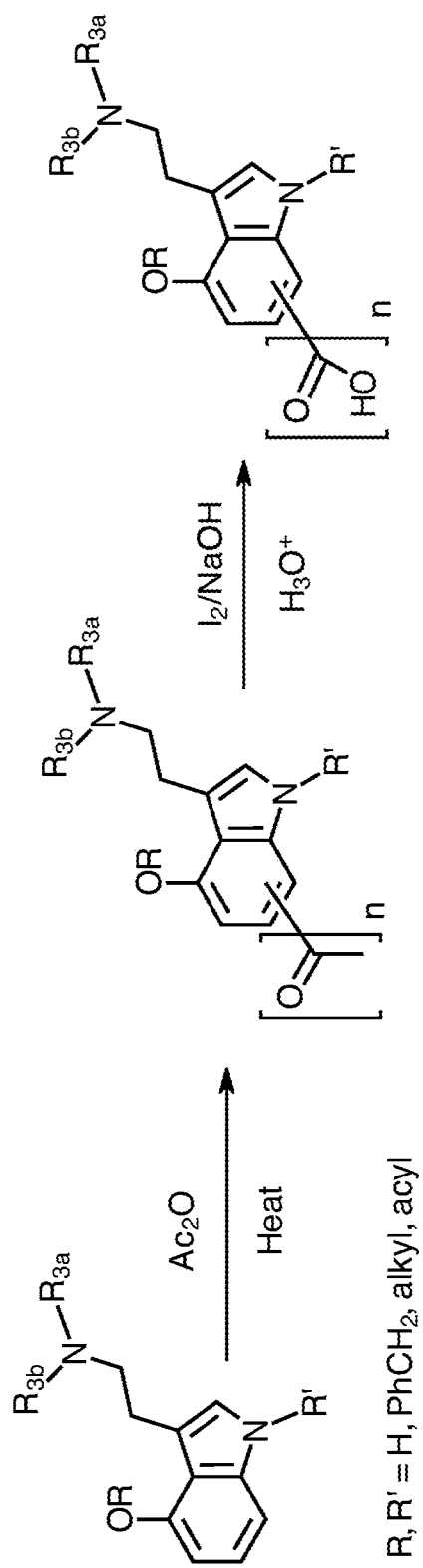

Referring now to FIGS. 10A, 10B and 10C, shown therein are various example reactions to prepare carboxylated psilocybin derivatives. FIG. 10A shows an example chemical reaction wherein a 4-hydroxy-psilocybin derivative (FIG. 9E) is reacted in a chemical reaction in the presence carbon dioxide (or sodium ethyl carbonate), and sodium hydroxide followed by an acidification with hydrochloric acid which results in the formation of a 4-hydroxy-5-carboxyl psilocybin derivative (Kolbe-Schmitt reaction).

Carboxylated psilocybin derivatives can also be prepared with a $N_{1/O4}$-protected psilocybin derivative (e.g., a benzyl protected derivative) that is halogenated at the desired position (FIG. 10B). For example, using the $N_{1/O4}$-di-benzyl-$C_7$-bromo-psilocin derivative, it is possible to convert the aryl halide to an organometallic intermediate by reacting with magnesium or to an aryl lithium by reacting with sec-butyllithium (not shown), the obtained organometallic intermediate (also known as Grignard intermediate) can then be reacted with carbon dioxide followed by an acidification to form the desired 7-carboxy intermediate in each case, and deprotecting both the $N_1/O_4$-di-benzyl groups by catalytic hydrogenation affords the desired 7-carboxypsilocin. The method illustrated in FIG. 10B can also be used to prepare psilocybin derivatives containing two or more carboxyl groups, notably by initiating the reaction with an aryl halide halogenated at multiple carbon atoms.

A further example method, shown in FIG. 10C, involves the performance of a Friedel-Craft acylation reaction (reaction with acetic anhydride) to install one or more acetyl groups onto a psilocybin derivative, such as psilocin (see: FIG. 9E), or on an $O_4$-protected psilocybin derivative (R may be alkyl, acyl, or benzyl ($PhCH_2$)). The acetyl group(s) can subsequently be converted to carboxylic acid group(s) via a haloform reaction (Fuson R. C. and Bull, B. A., 1934, Chem. Rev. 15 (3), 275-309), as illustrated in FIG. 10C.

Referring now to FIG. 15A, shown therein is an example multistep synthesis of 4-O-methyl-7-carboxy-substituted psilocybin derivative 15A-6 using 4-methoxyindole (15A-1) as a reactant. Compound 15A-1 can first be subjected to a 2-nitrovinylation at C-3 by reacting with N,N-dimethylamino-2-nitroethylene in trifluoroacetic acid. This afforded the desired I-3-(2-nitrovinyl) derivative (15A-2). The conjugated compound 15A-2 can then directly be reduced by sodium borohydride in a mixture of ethanol-THF to furnished 3-(2-nitroethyl)-4-methoxyindole (15A-3) in two steps. The reactive compound 15A-3 can then be subjected to a Friedel-Crafts acylation with trifluoroacetic anhydride in dichloromethane. The reaction can provide the corresponding 7-trifluoroacetyl derivative (15A-4). Subsequently, a base (KOH)-mediated transformation can be carried out with compound 15A-4 to provide the corresponding 7-carboxy derivative 15A-5. Finally, the nitro functionality of compound 11A-5 can be reduced in methanol at 40° C. by catalytic hydrogenolysis using ammonium formate as a reagent in the presence of 10% palladium on charcoal. This can yield the desired 4-O-methylated psilocybin derivative 15A-6.

Referring next to FIG. 15B, shown therein is another example multistep synthesis of 4-hydroxy-7-carboxy-substituted psilocybin derivative 15B-6 using 4-benzyloxyindole (15B-1) as a reactant. Compound 15B-1 can first be subjected to a similar 2-nitrovinylation at C-3 by reacting with N,N-dimethylamino-2-nitroethylene in trifluoroacetic acid. This can provide the desired (E)-3-(2-nitrovinyl) derivative (15B-2). Compound 15B-2 can subsequently be reduced by sodium borohydride in a mixture of ethanol-THF to furnished 3-(2-nitroethyl)-4-benzyloxyindole (15B-3). The reactive compound 15B-3 can also be subjected to a Friedel-Crafts acylation with trifluoroacetic anhydride in dichloromethane, and the reaction can provide the corresponding 7-trifluoroacetyl derivative (15B-4). Subsequently, a base (KOH)-mediated transformation can be carried out with compound 15B-4 to provide the corresponding 7-carboxy derivative 15B-5. Finally, the 4-O-benzyl can be removed, and the nitro functionality of compound 15B-5 can be reduced in methanol at 50° C. by catalytic hydrogenolysis, using ammonium formate as a reagent in the presence of 10% palladium on charcoal. This can yield the desired 4-hydroxy-7-carboxy substituted psilocybin derivative 15B-6.

Enzymatic carboxylation can also be realized in a carbonate buffer using a hydroxy substituted-psilocybin derivative such as FIG. 9E as a substrate. For example, with the help of a decarboxylase, ortho-carboxylation on phenol has been reported (see: Wuensch C. et al., 2012, Org Lett. 14 (8) 1974-1977). Additionally, phenol carboxylases have also been reported to regioselectively add a carboxyl group to the para-position of phenol (Lack, A. and Fuchs, G., 1992, J. Bacteriol. 174 (11) 3629-3636).

Thus, it will now be clear that, in an aspect hereof, the reactant psilocybin derivatives disclosed herein may be converted to a carboxylated psilocybin derivatives using one of the methods described above. Thus, in addition to reactant psilocybin derivative shown in FIG. 9E, the example reactant psilocybin derivatives shown in FIGS. 9B-9H may also be converted to a carboxylated psilocybin derivative using one of the methods disclosed in the present disclosure. The 4-O-methyl-psilocybin derivative depicted an FIG. 9A may be reacted to form, for example, the 4-O-methyl-5-carboxyl-psilocybin derivative depicted in FIG. 6A (as already noted), the 4-O-methyl-7-carboxyl-psilocybin derivative depicted in FIG. 7A, and the 4-O-methyl-5,7-di-carboxyl-psilocybin depicted in FIG. 8A.

Figure 6A:
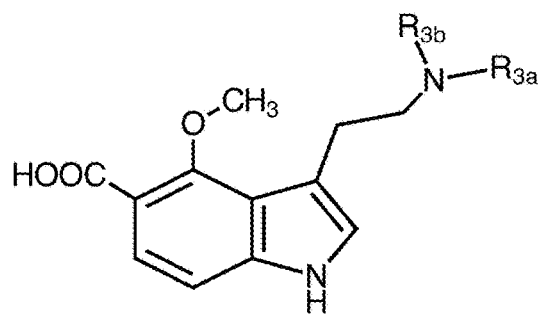
Figure 6B:
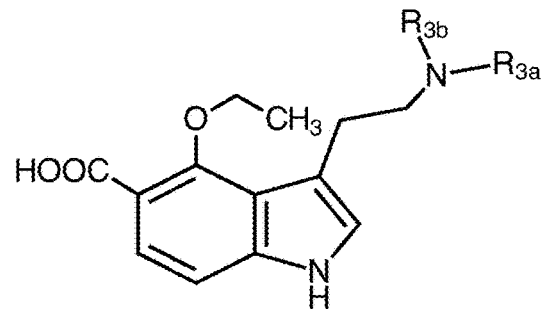
Figure 7A:
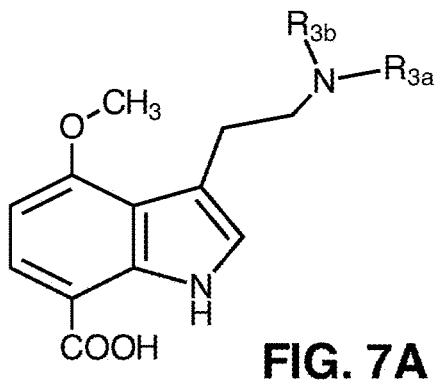
Figure 7B:
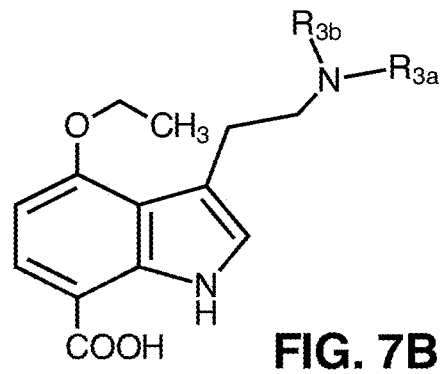
Figure 8A:
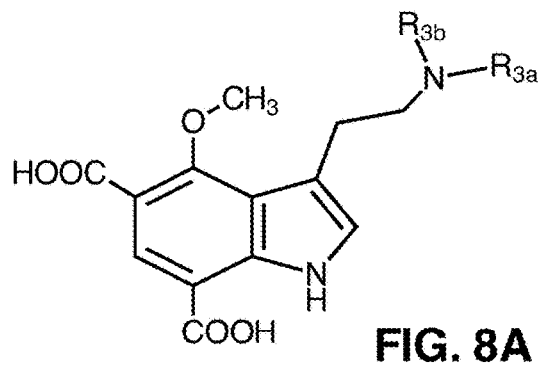
Figure 8B:
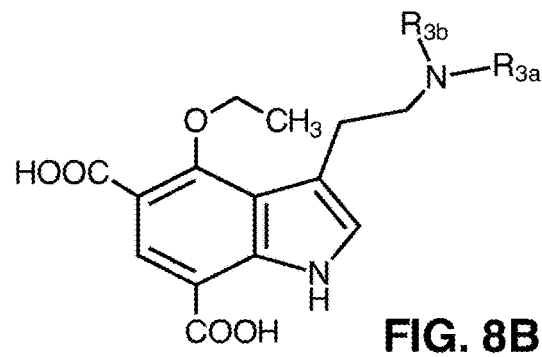

Similarly, the 4-O-ethyl-psilocybin derivative depicted an FIG. 9B may be reacted in similar reaction sequence to form, for example, the 4-O-ethyl-5-carboxyl-psilocybin derivative depicted in FIG. 6B, the 4-O-ethyl-7-carboxyl-psilocybin derivative depicted in FIG. 7B, and the 4-O-ethyl-5,7-di-carboxyl-psilocybin depicted in FIG. 8B.

Figure 6C:
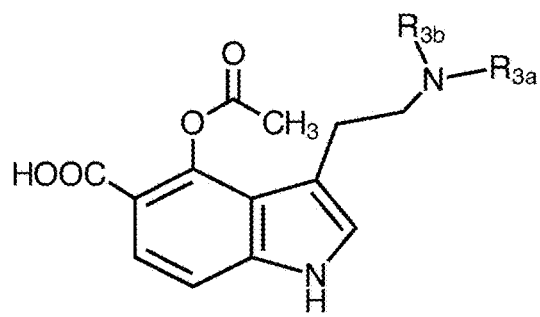
Figure 7C:
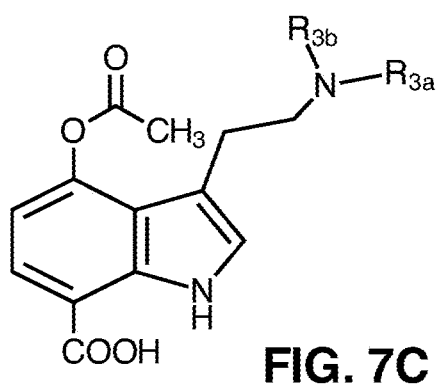
Figure 8C:
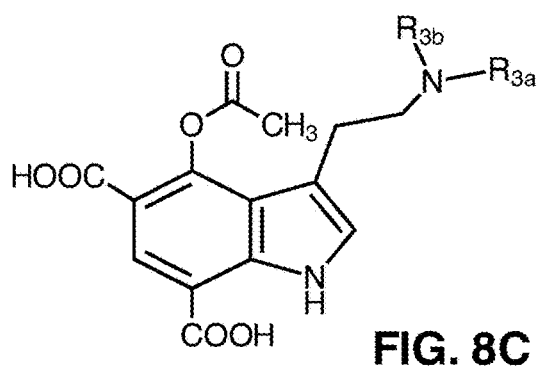
Figure 8D:
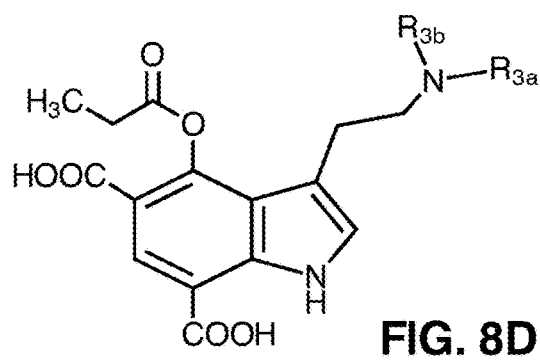
Figure 8E:
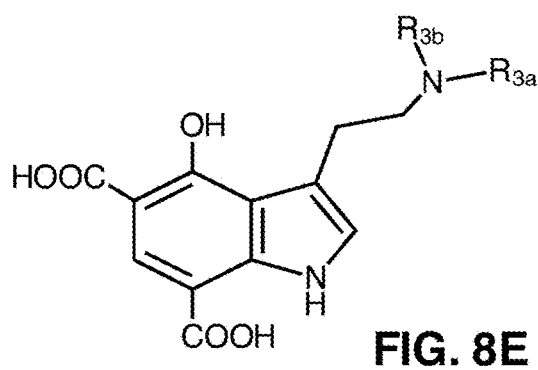
Figure 8F:
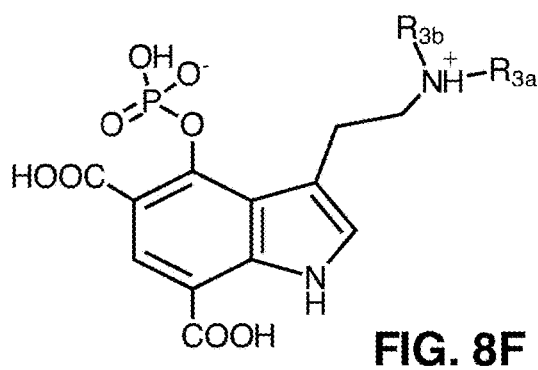
Figure 8G:
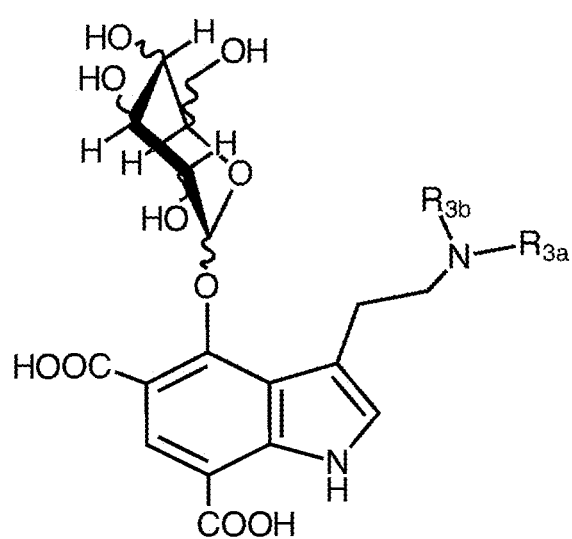
Figure 8H:
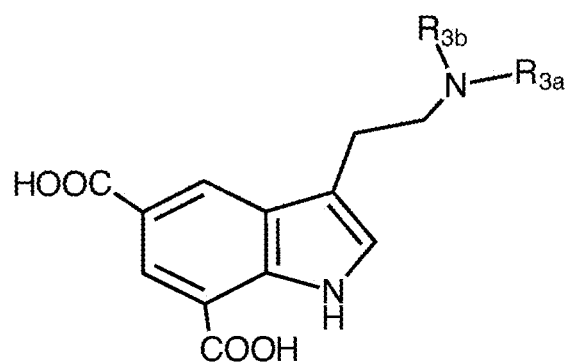

Similarly, the 4-acetyl-psilocybin derivative depicted an FIG. 9C may be reacted in similar reaction sequence to form, for example, the 4-O-acetyl-5-carboxyl-psilocybin derivative depicted in FIG. 6C, the 4-O-acetyl-7-carboxyl-psilocybin derivative depicted in FIG. 7C, and the 4-O-acetyl-5,7-di-carboxyl-psilocybin depicted in FIG. 8C.

Figure 6D:
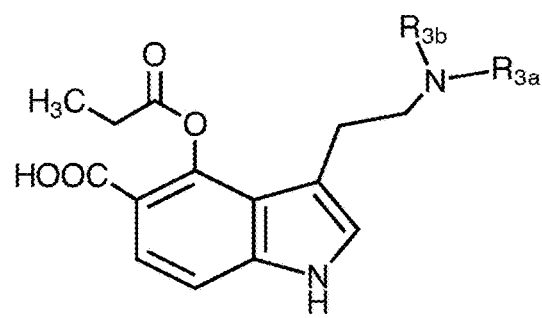
Figure 6E:
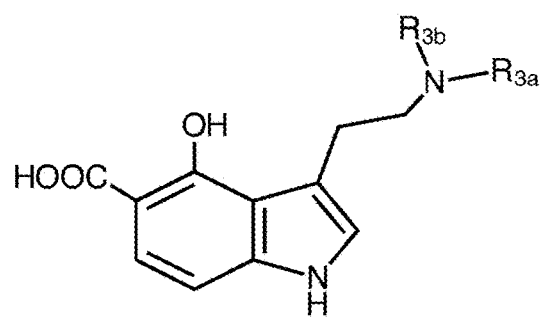
Figure 7D:
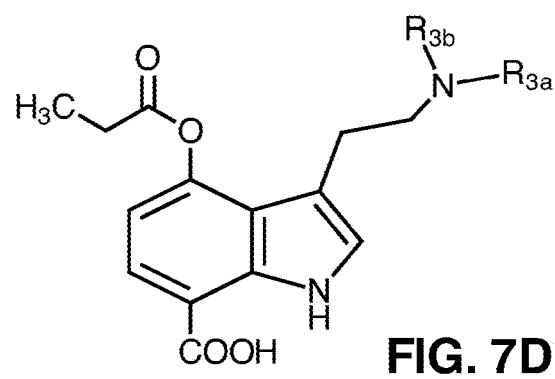
Figure 7E:
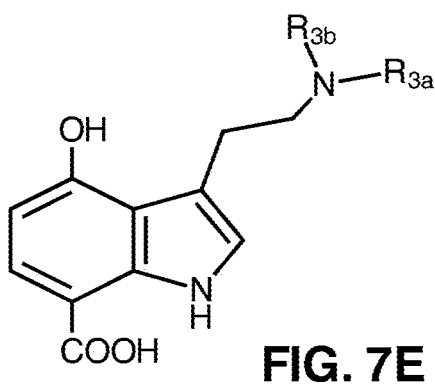
Figure 7F:
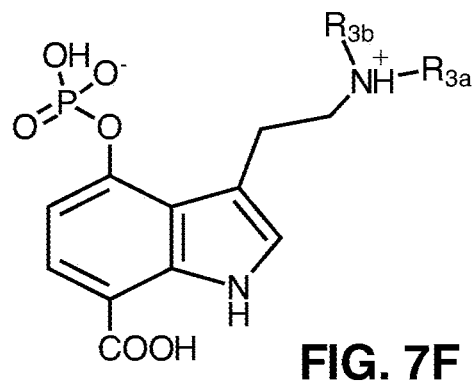
Figure 7G:
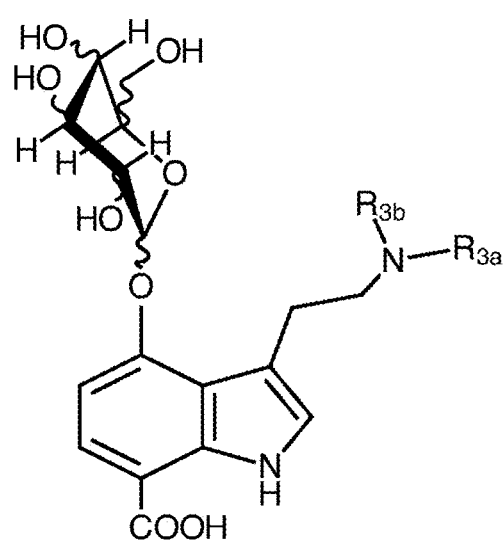
Figure 7H:
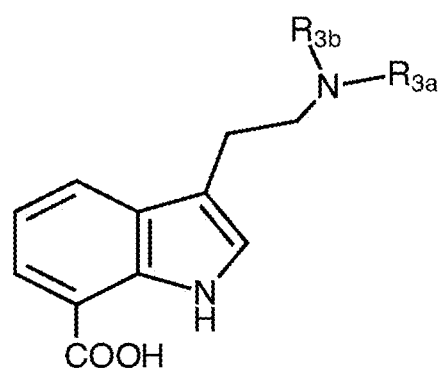

Similarly, the 4-propanoyl-psilocybin derivative depicted an FIG. 9D may be reacted in similar reaction sequence to form, for example, the 4-O-propanoyl-5-carboxyl-psilocybin derivative depicted in FIG. 6D, the 4-O-propanoyl-7-carboxyl-psilocybin derivative depicted in FIG. 7D, and the 4-O-propanoyl-5,7-di-carboxyl-psilocybin depicted in FIG. 7E.

Similarly, the 4-hydroxy-psilocybin derivative depicted an FIG. 9E may be reacted in similar reaction sequence to form, for example, the 4-hydroxy-5-carboxyl-psilocybin derivative depicted in FIG. 6E, the 4-hydroxy-7-carboxyl-psilocybin derivative depicted in FIG. 7E, and the 4-hydroxy-5,7-di-carboxyl-psilocybin depicted in FIG. 8E.

Similarly, the 4-phosphate-psilocybin derivative depicted an FIG. 9F may be reacted in similar reaction sequence to form, for example, the 4-phosphate-5-carboxyl-psilocybin derivative depicted in FIG. 6F, the 4-phosphate-7-carboxyl-psilocybin derivative depicted in FIG. 7F, and the 4-phosphate-5,7-di-carboxyl-psilocybin depicted in FIG. 8F.

Similarly, the 4-O-glycosyl-psilocybin derivative depicted an FIG. 9G may be reacted in similar reaction sequence to form, for example, the 4-O-glycosyl-5-carboxyl-psilocybin derivative depicted in FIG. 6G, the 4-O-glycosyl-7-carboxyl-psilocybin derivative depicted in FIG. 7G, and the 4-O-glycosyl-5,7-di-carboxyl-psilocybin depicted in FIG. 8G.

Similarly, the 4-hydro-psilocybin derivative depicted an FIG. 9H may be reacted to form, for example, the 4-hydro-5-carboxyl-psilocybin derivative depicted in FIG. 5H, the 4-hydro-7-carboxyl-psilocybin derivative depicted in FIG. 7H, and the 4-hydro-5,7-di-carboxyl-psilocybin depicted in FIG. 9H, as well as other analogs.

Furthermore, it is noted that the performance of the reactions, in example different embodiments, may involve carboxylation of different carbon atoms, i.e., the $C_2$, $C_5$, $C_6$, and/or $C_7$ atom. In general, reaction conditions may be selected so that different carbon atoms or combinations thereof are carboxylated. The methods can be used to prepare any other mono-, di- or multi-carboxylated psilocybin derivatives, as hereinbefore noted in particular with reference to FIGS. 10B and 10C.

Figure 10D:
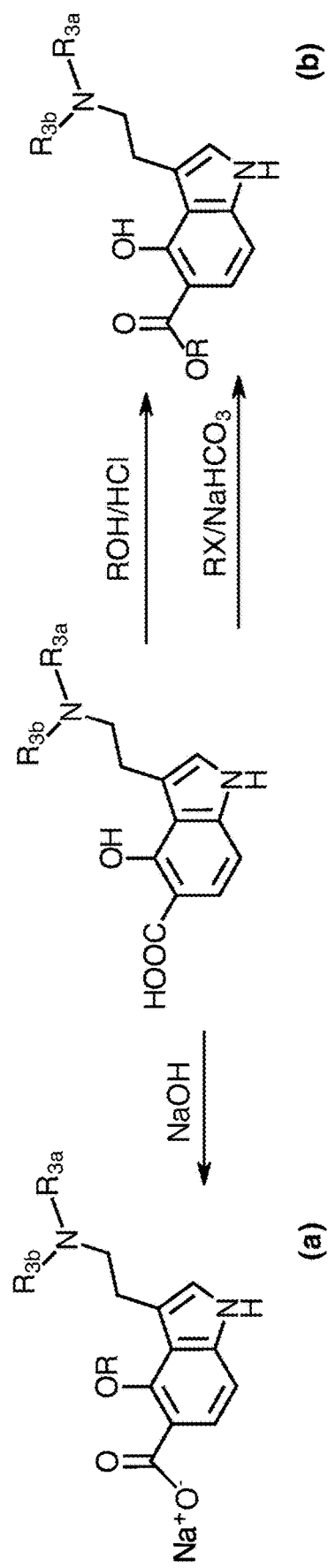

Referring now to FIG. 10D, carboxy-psilocybin derivatives may be used for further chemical derivatization of the carboxyl groups to further generate the derivatives such as, for example, the carboxyl-psilocybin derivatives depicted in FIGS. 3E-3H, 4A-4C, 5L-5X. For example, using 5-carboxy-psilocin (FIG. 6E), the carboxyl group can be neutralized with a suitable base such as NaOH to generate the carboxylate (see: FIG. 10D (a)). The carboxy group in 5-carboxyl-psilocin (FIG. 6E) can also be esterified using either an acidic condition with a suitable alcohol such as methanol, or using a basic condition by reacting with a suitable electrophile such as iodomethane (see: FIG. 10D (b)).

Referring again to FIGS. 15A and 15B, which illustrate a flexible synthesis to carboxylated psilocybin derivatives from 4-substituted indole derivatives. The substituents at 4-position of the indole can be other groups than the methoxy or benzyloxy groups, including an O-alkyl group, an O-acyl group, a hydroxy group, a phosphate group, a glycosyloxy group, etc., and these groups can occupy positions other than $C_4$ position of the indole. The acylating reagent used in the Friedel-crafts acylation step can be other organic anhydrides, acyl chlorides etc. Furthermore, the Friedel-Crafts acylation reactions can also provide additional products that are acylated at positions other than the 7-position. This can provide psilocybin derivatives bearing carboxy groups at other positions such a 2-carboxy, 5-carboxy, 6-carboxy derivatives.

The reactions, such as the example reaction shown in FIGS. 10A, 10B, 10C, 10D, 15A and 15B may be conducted in any suitable reaction vessel (e.g., a tube, bottle). Suitable solvents that may be used are for example, water, alcohol (such as methanol, ethanol, tetrahydrofuran (THF), N,N-dimethylformamide (DMF), dimethylsulfoxide (DMSO), or a combination of solvents. Suitable temperatures may range from, for example, e.g., from about 20° C. to about 100° C. Furthermore, reaction times may be varied. As will readily be appreciated by those of skill in the art, the reaction conditions may be optimized, for example, by preparing several psilocybin derivative reactants preparations and azido and reacting these in different reaction vessels under different reaction conditions, for example, at different temperatures, using different solvents, using different catalysts etc., evaluating the obtained carboxylated psilocybin derivative reaction product, adjusting reaction conditions, and selecting a desired reaction condition. Further general guidance regarding appropriate reaction conditions for performing carboxylation reactions may be found in, for example, Luo J. and Larrosa I., 2017, ChemSusChem, 10, 3317-3332.

It will now be clear from the foregoing that novel carboxylated psilocybin derivatives are disclosed herein, as well as methods of making carboxylated psilocybin derivatives. The carboxylated psilocybin compounds may be formulated for use as a pharmaceutical drug or recreational drug.

EXAMPLES

Example 1—Preparation and Pharmaceutical Efficacy Assays of a First Carboxylated Psilocybin Compound (a 4-O-methyl-7-carboxy psilocybin Derivative Preparation of carboxylated psilocybin derivative was performed according to the scheme shown in FIG. 15A.

Thus, referring to FIG. 15A, the first step involved the 3-nitrovinylation of 4-methyloxyindole. Trifluoroacetic acid (32.6 mL) was added to a mixture of 4-methoxyindole (see: FIG. 15A, compound 15A-1, 4.80 g, 32.6 mmol) and dimethylamino-2-nitroethylene (4.16 g, 35.8 mmol). The reaction mixture was stirred at room temperature for an hour before being poured into a mixture of EtOAc (208 mL) and 10% aqueous $Na_2CO_3$ (576 mL). The organic layer was separated, and the aqueous solution was extracted with EtOAc (3×300 mL). The combined organic solutions were washed with brine, dried over anhydrous $Na_2SO_4$ and concentrated in vacuo. The crude product (see: FIG. 15A, compound 15A-2) was used directly without further purification.

The second step involved the conjugated reduction of the vinyl functional group. To the crude material (15A-2) in EtOH (160 mL) and THF (160 mL) was added sodium borohydride (10.0 g, 264.20 mmol). The reaction mixture was stirred at room temperature overnight. The reaction mixture was carefully quenched with ice-water (852 mL) and extracted with dichloromethane (3×400 mL). The combined organic solutions were washed with brine, dried over anhydrous $Na_2SO_4$ and concentrated in vacuo. The crude product was purified by flash chromatography on silica gel using a gradient of hexanes-dichloromethane (20:80→0:100) to afford compound 15A-3 (see: FIG. 15A) as a red solid. Yield: 23%. $^1$H NMR (400 MHz, CDCl$_3$) δ 7.99 (s, 1H), 7.12 (t, J=8.0 Hz, 1H), 6.97 (dd, J=8.2, 0.7 Hz, 1H), 6.92 (d, J=2.3 Hz, 1H), 6.52 (d, J=7.8 Hz, 1H), 4.73 (t, J=7.2 Hz, 2H), 3.94 (s, 3H), 3.54 (t, J=7.2 Hz, 2H).

The third step involved the introduction of trifluoroacetyl group to the 7-position of indole using Friedel-Crafts acylation. Compound 15A-3 (0.42 g, 1.92 mmol) was dissolved in anhydrous dichloromethane (26 mL) at 0° C. Trifluoroacetic anhydride (1.60 mL) was added, and the reaction mixture was warmed up to room temperature. After 4 hours, the yellow precipitates were filtered, and dried under vacuum to afford compound 3. The filtrate was quenched with water (50 mL), extracted with DCM (3×50 mL), dried over anhydrous $Na_2SO_4$, and concentrated in vacuo. The crude product was 59 crystallized from a mixture of ethyl acetate-hexanes (1:1) to afford compound 15A-4 (see: FIG. 15A) as a yellow solid. Yield: 71%. $^1$H NMR (400 MHz, (CD$_3$)$_2$CO) δ 11.06 (s, 1H), 7.96 (dq, J=8.8, 2.2 Hz, 1H), 7.33-7.27 (m, 1H), 6.88 (d, J=8.7 Hz, 1H), 4.83 (t, J=7.0 Hz, 2H), 4.16 (s, 3H), 3.57 (td, J=7.1, 0.9 Hz, 2H). HRMS (ESI, positive) m/z for $C_{13}H_{12}F_3N_2O_4$ [M+H]$^+$ calcd. 317.0744, found 317.0743.

The fourth step involved the cleavage of the trifluoromethyl group from the 7-trifluoroacetylated substrate using a strong base. Compound 15A-4 (94 mg, 0.30 mmol) and potassium hydroxide (0.25 g, 4.53 mmol) were dissolved in anhydrous ethanol (5.5 ml) and water (5.5 mL). The reaction mixture was heated to reflux for 4 hour and 30 minutes then cooled to room temperature. Concentrated hydrochloric acid was added to the ice-cooled reaction mixture and the formed precipitates were filtered and dried under vacuum to afford compound 15A-5 (see: FIG. 15A) as a grey solid. Yield: 69%. $^1$H NMR (400 MHz, CD$_3$OD) δ 10.42 (bs, 1H), 7.84 (d, J=8.4 Hz, 1H), 7.05 (d, J=2.1 Hz, 1H), 6.63 (d, J=8.4 Hz, 1H), 4.74 (t, J=7.1 Hz, 2H), 4.00 (s, 3H), 3.50 (t, J=7.1 Hz, 2H). HRMS (ESI, positive) m/z for $C_{12}H_{13}N_2O_5$ [M+H]$^+$ calcd. 265.0819, found 265.0818.

The fifth step involved the reduction of the 2-nitroethyl group to generated the desired 2-aminoethyl functionality. To a solution of compound 15A-5 (100 mg, 0.38 mmol) was dissolved in MeOH (10 mL) was added 10% Pd/C (26 mg)

and ammonium formate (0.48 g, 7.6 mmol). The reaction mixture was heated at 40° C. for 4 hours. The catalyst was removed, and the filtrate was concentrated in vacuo. The crude mixture was purified through column chromatography on C18 silica gel using a 0% to 95% acetonitrile-water gradient to afford compound 15A-6 as a white solid (18 mg, 0.077 mmol, 20%). $^1$H NMR (400 MHz, D$_2$O) δ 7.74 (d, J=8.2 Hz, 1H), 7.19 (s, 1H), 6.69 (d, J=8.6 Hz, 1H), 4.00 (s, 3H), 3.32 (t, J=6.4 Hz, 2H), 3.20 (t, J=6.6 Hz, 2H). HRMS (ESI, positive) m/z for $C_{12}H_{15}N_2O_3$ [M+H]$^+$ calcd. 235.1077, found 235.1073. Purity was determined to be 95%. It is noted that compound 15A-6 corresponds with the chemical compound having formula (VI):

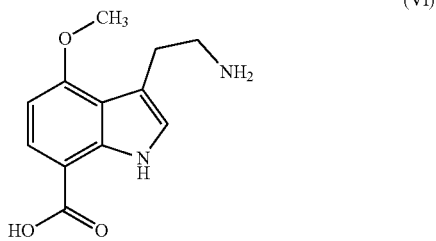

(VI)

set forth herein.

Figure 11:
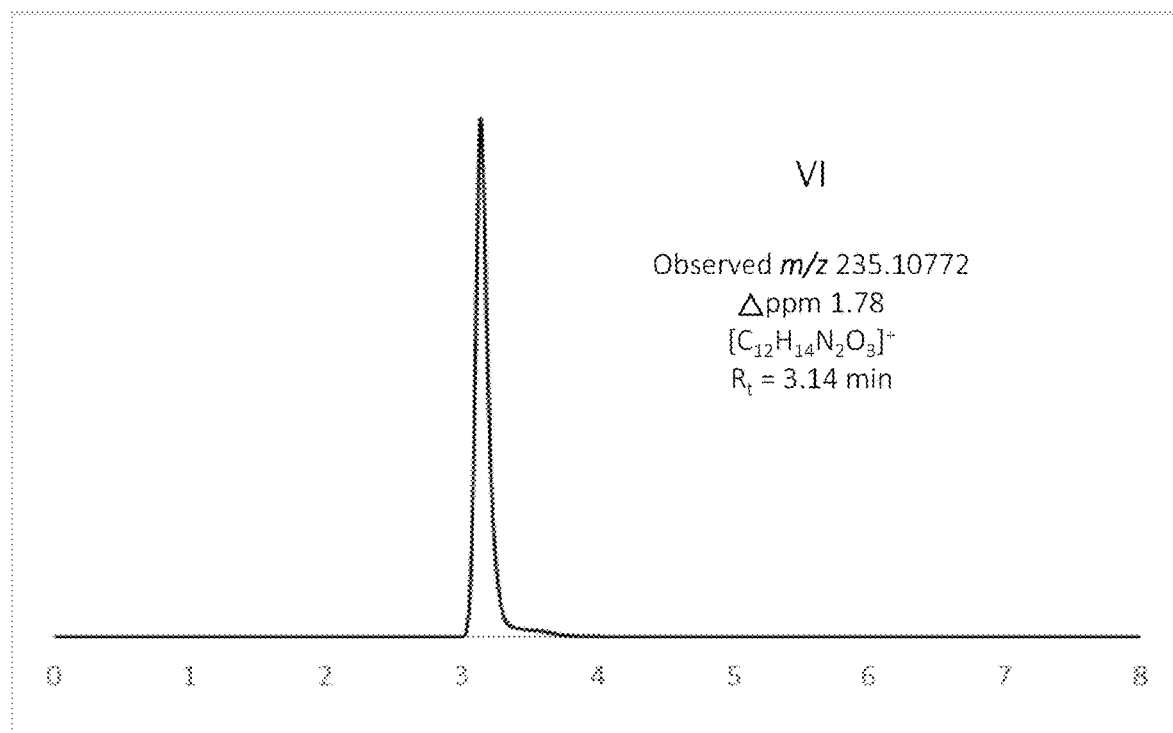
FIG. 11 depicts a representation of mass spectrometry data in the form of a chromatogram, notably a chromatogram obtained in the performance of an experiment to synthesize an example carboxylated psilocybin derivative compound having the chemical formulas (VI) set forth herein.

Further analysis was carried out using high-resolution LC-HESI-LTQ-Orbitrap-XL MS (Thermo Fisher Scientific), employing a modified version of a method described previously (Chang et al., 2015, Plant Physiol. 169: 1127-1140), with the exception that liquid chromatography was carried out using an UltiMate 3000 HPLC (Thermo Fisher Scientific) equipped with a Poroshell 120 SB-C18 column (Agilent Technologies) instead of an Accela HPLC system (Thermo Fisher Scientific) equipped with a Zorbax C18 column (Agilent Technologies). Briefly, 10 microliters of 1 uM methanolic solution of pure compound with formula (VI) was injected at a flow rate of 0.5 mL/min and a gradient of solvent A (water with 0.1% of formic acid) and solvent B (I with 0.1% formic acid) as follows: 100% to 0% (v/v) solvent A over 5 min; isocratic at 0% (v/v) for 1 min; 0% to 100% (v/v) over 0.1 min; and isocratic at 100% (v/v) for 1.9 min. Total run time was 8 minutes. Heated ESI source and interface conditions were operated in positive ion mode as follows: vaporizer temperature, 400° C.; source voltage, 3 kV; sheath gas, 60 au, auxiliary gas, 20 au; capillary temperature, 380° C.; capillary voltage, 6 V; tube lens, 45 V. Instrumentation was performed as a single, HR scan event using Orbitrap detection of m/z in the range of 100-500 m/z. Ion injection time was 300 ms with scan time of 1 s. External and internal calibration procedures ensured <2 ppm error to facilitate elemental formulae predictions. Singly protonated product with exact m/z and expected elemental formula matching the singly protonated form of compound with formula (VI) eluted at 3.14 minutes (EIC, see: FIG. 11).

Figure 12A:
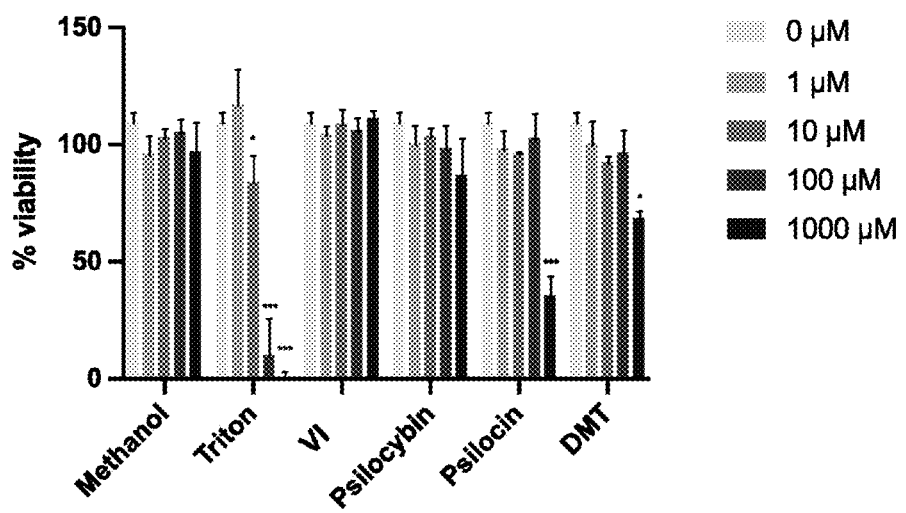
FIGS. 12A and 12B depicts a graph obtained in the performance of an experimental assay to evaluate the efficacy of example carboxylated psilocybin derivatives, notably a cell viability assay involving an example carboxylated psilocybin derivative compound having the chemical formula (VI) (FIG. 12A) and (VII) (FIG. 12B) set forth herein.

Assessment of Cell Viability Upon Treatment of a Carboxylated Psilocybin Derivative To establish suitable ligand concentrations for competitive binding assays, PrestoBlue assays were first performed. The PrestoBlue assay measures cell metabolic activity based on tetrazolium salt formation, and is a preferred method for routine cell viability assays (Terrasso et al., 2017, J Pharmacol Toxicol Methods 83: 72). Results of these assays were conducted using both control ligands (e.g., psilocybin, psilocin, DMT) and novel derivatives, in part as a pre-screen for any remarkable toxic effects on cell cultures up to concentrations of 1 mM. A known cellular toxin (Triton X-100, Pyrgiotakis G. et al., 2009, Ann. Biomed. Eng. 37: 1464-1473) was included as a general marker of toxicity. Drug-induced changes in cell health within simple in vitro systems such as the HepG2 cell line are commonly adopted as first-line screening approaches in the pharmaceutical industry (Weaver et al., 2017, Expert Opin Drug Metab Toxicol 13: 767). HepG2 is a human hepatoma that is most commonly used in drug metabolism and hepatotoxicity studies (Donato et al., 2015, Methods Mol Biol 1250: 77). Herein, HepG2 cells were cultured using standard procedures using the manufacture's protocols (ATCC, HB-8065). Briefly, cells were cultured in Eagle's minimum essential medium supplemented with 10% fetal bovine serum and grown at 37° C. in the presence of 5% CO$_2$. To test the various compounds with the cell line, cells were seeded in a clear 96-well culture plate at 20,000 cells per well. After allowing cells to attach and grow for 24 hours, compounds were added at 1 μM, 10 μM, 100 M, and 1 mM. Methanol was used as vehicle, at concentrations 0.001, 0.01, 0.1, and 1%. As a positive control for toxicity, TritonX concentrations used were 0.0001, 0.001, 0.01 and 0.1%. Cells were incubated with compounds for 48 hours before accessing cell viability with the PrestoBlue assay following the manufacture's protocol (ThermoFisher Scientific, P50200). PrestoBlue reagent was added to cells and allowed to incubate for 1 hour before reading. Absorbance readings were performed at 570 nm with the reference at 600 nm on a SpectraMax iD3 plate reader. Non-treated cells were assigned 100% viability. Bar graphs show the mean+/−SD, n=3. Significance was determined by 2-way ANOVA followed by Dunnett's multiple comparison test and is indicated by *(P<0.0001), (P<0.001), *(P<0.005). Data acquired for the derivative having chemical formula (VI) is displayed as "VI" on the x-axis of FIG. 12A.

Radioligand Receptor Binding Assays.

Evaluation of drug binding is an essential step to characterization of all drug-target interactions (Fang 2012, Exp Opin Drug Discov 7:969). The binding affinity of a drug to a target is traditionally viewed as an acceptable surrogate of its in vivo efficacy (Núñez et al., 2012, Drug Disc Today 17: 10). Competition assays, also called displacement or modulation binding assays, are a common approach to measure activity of a ligand at a target receptor (Flanagan 2016, Methods Cell Biol 132: 191). In these assays, standard radioligands acting either as agonists or antagonists are ascribed to specific receptors. In the case of G protein-coupled receptor 5-HT$_{2A}$, [$^3$H]ketanserin is a well-established antagonist used routinely in competition assays to evaluate competitive activity of novel drug candidates at the 5-HT$_{2A}$ receptor (Maguire et al., 2012, Methods Mol Biol 897: 31). Thus, to evaluate activity of novel carboxylic acid-containing psilocybin derivatives at the 5-HT$_{2A}$ receptor, competition assays using [$^3$H]ketanserin were employed as follows. SPA beads (RPNQ0010), [$^3$H] ketanserin (NET1233025UC), membranes containing 5-HT$_{2A}$ (ES-313-M400UA), and isoplate-96 microplate (6005040) were all purchased from PerkinElmer. Radioactive binding assays were carried out using Scintillation Proximity Assay (SPA). For saturation binding assays, mixtures of 10 ug of membrane containing 5-HT$_{2A}$ receptor was pre-coupled to 1 mg of SPA beads at room temperature in a tube rotator for 1 hour in binding buffer (50 mM Tris-HCl pH7.4, 4 mM CaCl$_2$, 1 mM ascorbic acid, 10 μM pargyline HCl). After pre-coupling, the beads and membrane were aliquoted in an isoplate-96 microplate with increasing amounts of [$^3$H]ketanserin (0.1525 nM to 5 nM) and incubated for two hours at room temperature in the dark with shaking. After incubation, the samples were read on a MicroBeta 2 Microplate Counter (Perkin Elmer). Determination of non-specific binding was carried out in the presence of 20 µM of spiperone (S7395-250MG, Sigma). Equilibrium binding constants for ketanserin ($K_d$) were determined from saturation binding curves using the 'one-site saturation binding analysis' method of GraphPad PRISM software (Version 9.2.0). Competition binding assays were performed using fixed (1 nM) [$^3$H] ketanserin and different concentrations of tryptophan (3 nM to 1 mM), psilocin (30 pM to 10 µM) or unlabeled test compound (3 nM to 1 mM) similar to the saturation binding assay. $K_i$ values were calculated from the competition displacement data using the competitive binding analysis from GraphPad PRISM software. Tryptophan was included as a negative control as it has no activity at the 5-$HT_{2A}$ receptor. In contrast, psilocin was used as a positive control since it has established binding activity at the 5-$HT_{2A}$ receptor (Kim et al., 2020, Cell 182: 1574). FIG. 13A depicts the saturation binding curves for [$^3$H]ketanserin at the 5-$HT_{2A}$ receptor. Panel 1 shows the specific saturation ligand binding of [$^3$H]ketanserin (from 0.1525 nM to 5 nM) to membranes containing 5-$HT_{2A}$ receptor, which was obtained after subtracting non-specific binding values (shown in Panel 2). Specific binding in counts per minute (cpm) was calculated by subtracting non-specific binding from total binding. Specific binding (pmol/mg) was calculated from pmol of [$^3$H]ketanserin bound per mg of protein in the assay. The $K_d$ was calculated by fitting the data with the one-site binding model of PRISM software (version 9.2.0). FIG. 13B shows the competition binding curve for psilocin as a positive control (binding). FIG. 13C shows the competition binding curve for tryptophan as a negative control (no binding). FIG. 13D shows competition binding curve for compound with formula (VI), designated "VI" in the figure.

Cell Lines and Control Ligands Used to Assess Activity at 5-$HT_{1A}$.

CHO-K1/G$\alpha_{15}$ (GenScript, M00257) (−5-$HT_{1A}$) and CHO-K1/5-$HT_{1A}$/G$\alpha_{15}$ (GenScript, M00330) (+5-$HT_{1A}$) cells lines were used. Briefly, CHO-K1/G$\alpha_{15}$ is a control cell line that constitutively expresses G$\alpha_{15}$ which is a promiscuous $G_q$ protein. This control cell line lacks any transgene encoding 5-$HT_{1A}$ receptors, but still responds to forskolin; thus, cAMP response to forskolin should be the same regardless of whether or not 5-$HT_{1A}$ agonists are present. Conversely, CHO-K1/5-$HT_{1A}$/G$\alpha$15 cells stably express 5-$HT_{1A}$ receptor in the CHO-K1 host background. Notably, G$\alpha_{15}$ is a promiscuous G protein known to induce calcium flux response, present in both control and 5-$HT_{1A}$ cell lines. In +5-$HT_{1A}$ cells, G$\alpha_{15}$ may be recruited in place of $G_{\alpha i/o}$, which could theoretically dampen cAMP response (Rojas and Fiedler 2016, Front Cell Neurosci 10: 272). Thus, we included two known 5-$HT_{1A}$ agonists, DMT (Cameron and Olson 2018, ACS Chem Neurosci 9: 2344) and serotonin (Rojas and Fiedler 2016, Front Cell Neurosci 10: 272) as positive controls to ensure sufficient cAMP response was observed, thereby indicating measurable recruitment of $G_{\alpha i/o}$ protein to activated 5-$HT_{1A}$ receptors. In contrast, tryptophan is not known to activate 5-$HT_{1A}$ receptors, and was thus used as a negative control. Cells were maintained in complete growth media as recommended by supplier (GenScript) which is constituted as follows: Ham's F12 Nutrient mix (HAM's F12, GIBCO #11765-047) with 10% fetal bovine serum (FBS) (Thermo Scientific #12483020), 200 µg/ml zeocin (Thermo Scientific #R25005) and/or 100 µg/ml hygromycin (Thermo Scientific #10687010). The cells were cultured in a humidified incubator with 37° C. and 5% $CO_2$. Cells maintenance was carried out as recommended by the cell supplier. Briefly, vials with cells were removed from the liquid nitrogen and thawed quickly in 37° C. water bath. Just before the cells were completely thawed the vial's outside was decontaminated by 70% ethanol spray. The cell suspension was then retrieved from the vial and added to warm (37° C.) complete growth media, and centrifuged at 1,000 rpm for 5 minutes. The supernatant was discarded, and the cell pellet was then resuspended in another 10 ml of complete growth media, and added to the 10 cm cell culture dish (Greiner Bio-One #664160). The media was changed every third day until the cells were about 90% confluent. The ~90% confluent cells were then split 10:1 for maintenance or used for experiment.

Evaluation of 5-$HT_{1A}$ Activation by Carboxylated Psilocybin Derivatives

As 5-$HT_{1A}$ activation inhibits cAMP formation, the agonist activity of test molecules on 5-$HT_{1A}$ was measured via the reduction in the levels of cAMP produced due to application of 4 µM forskolin. The change in intracellular cAMP levels due to the treatment of novel molecules was measured using cAMP-Glo Assay kit (Promega #V1501). Briefly, +5-$HT_{1A}$ cells were seeded on 1-6 columns and base −5-$HT_{1A}$ cells were seeded on columns 7-12 of the white walled clear bottom 96-well plate (Corning, #3903). Both cells were seeded at the density of 30,000 cells/well in 100 µl complete growth media and cultured 24 hrs in humidified incubator at 37° C. and 5% $CO_2$. On the experiment day, the media of cells was replaced with serum/antibiotic free culture media. Then the cells were treated for 20 minutes with test molecules dissolved in induction medium (serum/antibiotic free culture media containing 4 µM forskolin, 500 µM IBMX (isobutyl-1-methylxanthine, Sigma-Aldrich, Cat. #17018) and 100 µM (RO 20-1724, Sigma-Aldrich, Cat. #B8279)). Forskolin induced cAMP formation whereas IBMX and RO 20-1724 inhibited the degradation of cAMP. PKA was added to the lysate, mixed, and subsequently the substrate of the PKA was added. PKA was activated by cAMP, and the amount of ATP consumed due to PKA phosphorylation directly corresponded to cAMP levels in the lysate. Reduced ATP caused reduced conversion of luciferin to oxyluciferin, conferring diminished luminescence as the result of 5-$HT_{1A}$ activation. FIG. 14A shows increased luminescence resulting from decreased dosages of forskolin (and decreased cAMP) in +5$HT_{1A}$ cell culture. FIG. 14B illustrates reduced luminescence (i.e., increased cAMP) in the presence of fixed (4 µM) forskolin as dosages of DMT decrease, revealing 5-$HT_{1A}$ activity of DMT. FIG. 14C illustrates no trend in luminescence (i.e., no trend in cAMP levels) in the presence of fixed (4 µM) forskolin, as dosages of tryptophan decrease, revealing a lack of 5-$HT_{1A}$ activity for tryptophan. FIG. 14D illustrates increased % cAMP levels in the presence of fixed (4 µM) forskolin as dosages of serotonin decrease, revealing 5-$HT_{1A}$ binding activity of serotonin in +5$HT_{1A}$ cell cultures. Conversely, this trend of increasing % cAMP levels with decreasing serotonin is not observed in −5$HT_{1A}$ cell cultures. FIG. 14E illustrates subtly increased % cAMP levels in the presence of fixed (4 µM) forskolin as dosages of compound (VI) decrease, revealing mild 5-$HT_{1A}$ binding activity of compound (VI) in +5$HT_{1A}$ cell cultures. Conversely, this trend of increasing % cAMP levels with decreasing compound (VI) is not observed in −5$HT_{1A}$ cell cultures. Note that compound (VI) is shown simply as (VI) along the x-axis. For FIGS. A-C, error bars represent results of three experiments (n=3).

Example 2—Preparation and Pharmaceutical Efficacy Assays of a Second Carboxylated Psilocybin Compound (a 4-hydroxy-7-carboxy psilocybin Derivative Preparation of carboxylated psilocybin derivative was performed according to the scheme shown in FIG. 15-B. Thus, referring to FIG. 15B, the first step involved the 3-nitrovinylation of 4-benzyloxyindole. Trifluoroacetic acid (22 mL) was added to a mixture of 4-benzyloxyindole (see: FIG. 15B, compound 15B-1, 5.0 g, 22.3 mmol) and dimethylamino-2-nitroethylene (2.86 g, 24.6 mmol). The reaction mixture was stirred at room temperature for an hour before being poured into a mixture of EtOAc (150 mL) and 10% aqueous $Na_2CO_3$ (200 mL). The organic layer was separated, and the aqueous solution was extracted with EtOAc (100 mL). The combined organic solutions were washed with brine, dried over anhydrous $Na_2SO_4$ and concentrated in vacuo. The crude mixture was purified by column chromatography on silica gel using a gradient of 5-20% EtOAc-hexane as the eluent to afford compound 15B-2 (see: FIG. 15B, 2.1 g, 32% yield). $^1$H NMR (400 MHz, $CDCl_3$) δ 8.79 (s, 1H, NH), 8.60 (d, J=13.5 Hz, 1H), 7.84 (d, J=13.5 Hz, 1H), 7.59 (d, J=2.8 Hz, 1H), 7.56-7.32 (m, 5H), 7.23 (t, J=8.0 Hz, 1H), 7.08 (d, J=8.1 Hz, 1H), 6.77 (d, J=7.9 Hz, 1H), 5.30 (s, 2H).

The second step involved the conjugated reduction of the vinyl functional group. To a solution of (E)-4-benzyloxy-3-(2-nitrovinyl)-1H-indole (15B-2, 0.91 g, 3.10 mmol) in a mixture of THF (15 mL) and anhydrous ethanol (15 mL), was added sodium borohydride (0.94 g, 24.83 mmol), and the reaction mixture was stirred at room temperature overnight. The reaction mixture was carefully quenched with ice-water (100 mL) and the solution extracted with dichloromethane (3×60 mL). The combined organic solutions were washed with brine, dried over anhydrous $Na_2SO_4$, and concentrated in vacuo. The crude product was purified by flash chromatography on silica gel using a gradient of hexanes-dichloromethane (20:80→0:100) to afford compound 15B-3 (see: FIG. 15B) as a yellow solid. Yield: 42%. $^1$H NMR (400 MHz, $CDCl_3$) δ 8.01 (s, 1H), 7.51-7.32 (m, 5H), 7.11 (t, J=8.0 Hz, 1H), 6.99 (d, J=8.2 Hz, 1H), 6.93 (d, J=2.3 Hz, 1H), 6.61 (d, J=7.8 Hz, 1H), 5.19 (s, 2H), 4.62 (t, J=7.0 Hz, 2H), 3.50 (t, J=7.1 Hz, 2H).

The third step involved the introduction of trifluoroacetyl group to the 7-position of indole using Friedel-Crafts acylation. A solution of compound 15B-3 (0.10 g, 0.34 mmol) in anhydrous DCM (5.0 mL) was cooled with an ice-water bath, and trifluoroacetic anhydride (0.42 mL) was added. After stirring reaction mixture for 7 hours at room temperature, the yellow precipitates were filtered off and dried under vacuum to afford compound 15B-4 (see: FIG. 15B). The filtrate was quenched with water (10 mL), and the mixture was extracted with dichloromethane (3×10 mL). The combined organic solutions were dried over anhydrous $Na_2SO_4$ and concentrated in vacuo. The crude product was recrystallized from a mixture of ethyl acetate and hexanes (1:1) to afford compound 15B-4 as a yellow solid. Yield: 40%. $^1$H NMR (400 MHz, $(CD_3)_2CO$) δ 11.07 (s, 1H), 7.95 (dq, J=8.7, 2.2 Hz, 1H), 7.64-7.59 (m, 2H), 7.49-7.36 (m, 3H), 7.31 (d, J=2.4 Hz, 1H), 6.99 (d, J=8.7 Hz, 1H), 5.50 (s, 2H), 4.76 (t, J=7.1 Hz, 2H), 3.54 (t, J=7.0 Hz, 2H). HRMS (ESI, positive) m/z for $C_{19}H_{16}F_3N_2O_4$ [M+H]$^+$ calcd. 393.1057, found 393.1058.

The fourth step involved the cleavage of the trifluoromethyl group from the 7-trifluoroacetylated substrate using a strong base. A solution of compound 15B-4 (52.8 mg, 0.13 mmol) and potassium hydroxide (73 mg, 1.30 mmol) in ethanol (2.5 ml) and water (2.5 mL) was heated to reflux for 3 hours. The reaction solution was then cooled to room temperature, and further to 0° C. with an ice-water bath, concentrated hydrochloric acid was then added to neutralize the reaction mixture. The precipitates were filtered and dried under vacuum to afford compound 15B-5 (see: FIG. 15B) as a greyish white solid. Yield: 40%. $^1$H NMR (400 MHz, d$^6$-DMSO) δ 12.66 (s, 1H), 10.91-10.85 (m, 1H), 7.72 (d, J=8.3 Hz, 1H), 7.54-7.49 (m, 2H), 7.43-7.32 (m, 3H), 7.06 (d, J=2.5 Hz, 1H), 6.74 (d, J=8.4 Hz, 1H), 5.30 (s, 2H), 4.74 (t, J=7.0 Hz, 2H), 3.41 (t, J=7.0 Hz, 2H). $^{13}$C NMR (100 μMHz, d$^6$-DMSO) δ 25.00, 70.11, 76.99, 101.17, 107.94, 109.62, 117.41, 124.49, 127.18, 128.07, 128.45, 129.00, 137.16, 137.41, 157.30, 167.95. HRMS (ESI, positive) m/z for $C_{18}H_{17}N_2O_5$ [M+H]$^+$ calcd. 341.1132, found 341.1133.

The fifth step involved the simultaneous remove of 4-O-benzyl group and the reduction of the 2-nitroethyl group to generated the desired 2-aminoethyl functionality. To a solution of compound 11B-5 (68 mg, 0.20 mmol) in MeOH (10 mL), was added 10% Pd/C (13 mg) and ammonium formate (0.25 g, 1.25 mmol), and the reaction mixture was stirred at room temperature for 3 hours then heated at 40° C. The catalyst was removed by filtration, and the filtrate was concentrated in vacuo to afford compound 15B-6 (see: FIG. 15B) as a brown solid. Yield: 38%. $^1$H NMR (400 MHz, $CD_3OD$) δ 8.52 (s, 9H), 7.68 (d, J=8.2 Hz, 1H), 7.08 (s, 1H), 6.45 (d, J=8.2 Hz, 1H), 3.33-3.28 (m, 2H), 3.22 (t, J=7.5 Hz, 2H). HRMS (ESI, positive) m/z for $C_{11}H_{13}N_2O_3$ [M+H]$^+$ calcd. 221.0921, found 221.0923. It is noted that compound 15B-6 corresponds with the chemical compound having formula (VII):

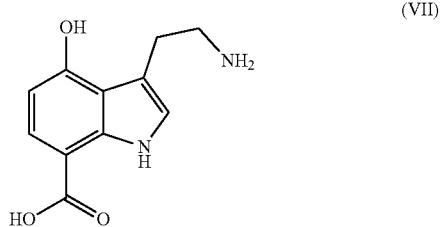 [SMILES: NCCc1c[nH]c2c(C(=O)O)ccc(O)c12]

(VII)

set forth herein.

Figure 12B:
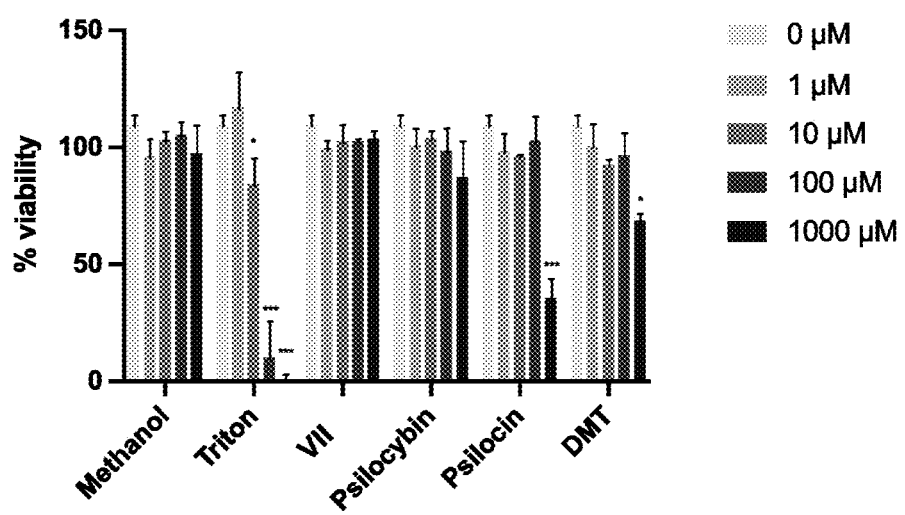

Assessment of Cell Viability Upon Treatment of Carboxylated Psilocybin Derivative Cell viability was assessed as described for Example 1, except the compound with formula (VII) was evaluated in place of the compound with formula (VI). FIG. 12B shows PrestoBlue assay results for compound with formula (VII), depicted on the x-axis as "VII".

Radioligand Receptor Binding Assays.

Activity at 5-HT$_{2A}$ receptor was assessed as described for Example 1, except the compound with formula (VII) was evaluated in place of the compound with formula (VI). FIG. 13E shows radioligand competition assay results for compound with formula (VII), depicted on the x-axis simply as "VII".

Cell Lines and Control Ligands Used to Assess Activity at 5-HT$_{1A}$ and Evaluation of 5-HT$_{1A}$ Activation by Carboxylated Psilocybin Derivatives Cell lines, cell line maintenance, and experimental procedures assessing binding of 5-HT$_{1A}$ were performed as described in Example 1, except that compound (VII) was evaluated in place of compound (VI). FIG. 14F illustrates increased % cAMP levels in the presence of fixed (4 mM) forskolin as dosages of compound (VII) decrease, revealing 5-$HT_{1A}$ binding activity of compound (VII) in +5$HT_{1A}$ cell cultures. Conversely, this trend of increasing % cAMP levels with decreasing compound (VII) is not observed in −5$HT_{1A}$ cell cultures. Note that compound (VII) is shown simply as (VI) along the x-axis.

Example 3—Preparation of a Third Carboxylated Psilocybin Compound

Preparation of carboxylated psilocybin derivative was performed according to the scheme shown in FIG. 16. Thus, referring to FIG. 16, a solution of compound 1 (see: FIG. 16) (120 mg) in anhydrous DCM (5.0 mL) was cooled with an ice-water bath, and trifluoroacetic anhydride (0.45 mL) was added. After stirring reaction mixture for 7 hours at room temperature, the reaction was quenched with water (10 mL), and the mixture was extracted with ethyl acetate (3×10 mL). The combined organic solutions were dried over anhydrous $Na_2SO_4$ and concentrated in vacuo. The crude product was purified by flash chromatography on silica gel column using hexanes/EtOAc as eluent to afford a crude compound 2 (see: FIG. 16) as a yellow solid. 1H NMR showed it was still crude mixture, but HRMS did observe the desired product. HRMS (ESI, positive) m/z for $C_{16}H_{20}F_3N_2O_2$ $[M+H]^+$ calcd. 329.1471, found 329.1466. A solution of compound 2 and potassium hydroxide (10 eq) in ethanol (2.5 ml) and water (2.5 mL) was heated to reflux for 3 hours. The reaction solution was then cooled to room temperature, and further to 0° C. with an ice-water bath; concentrated hydrochloric acid was then added to neutralize the reaction mixture. The precipitates were filtered and dried under vacuum to afford compound 3 (see: FIG. 16) as a pale yellow solid. Compound 3 is a compound having chemical formula (VIII). HRMS (ESI, positive) m/z for $C_{16}H_{21}N_2O_3$ $[M+H]^+$ calcd. 277.1547, found 277.1550.

The invention claimed is:

1. A chemical compound having the formula (I):

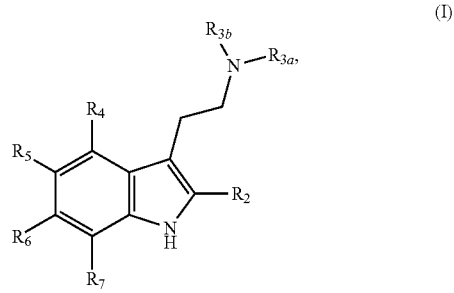

(I)

wherein $R_7$ is a carboxyl group and wherein $R_2$ is a hydrogen atom, $R_5$ or and $R_6$ are a hydrogen atom, an alkyl group, or O-alkyl group, wherein $R_4$ is an O-alkyl group, and wherein $R_{3a}$ and $R_{3b}$ are each independently a hydrogen atom, an alkyl group, acyl group or an aryl group.

2. A chemical compound according to claim 1, wherein the carboxyl group is a carboxylate ion and forms a carboxylic acid salt having the formula $COO^-M^+$, wherein $M^+$ is an organic or inorganic cation.

3. A chemical compound according to claim 2, wherein $M^+$ is selected from $Na^+$, $K^+NR_4^+$, wherein $R_{3a}$ and $R_{3b}$ independently are H, an alkyl, or an aryl.

4. A chemical compound according to claim 1, wherein $R_5$ and $R_6$ are a hydrogen atom.

5. A chemical compound according to claim 1, wherein $R_5$ and $R_6$ are a hydrogen atom, and $R_4$ is a ($C_1$-$C_{10}$)—O-alkyl group.

6. A chemical compound according to claim 1, wherein $R_5$ and $R_6$ are a hydrogen atom, and $R_4$ is a ($C_1$-$C_6$)—O-alkyl group.

7. A chemical compound according to claim 1, wherein $R_5$ and $R_6$ are a hydrogen atom, and $R_4$ is a ($C_1$-$C_3$)—O-alkyl group.

8. A chemical compound according to claim 1 wherein $R_5$ and $R_6$ are a hydrogen atom, and $R_4$ is a methoxy (—$OCH_3$) group.

9. A chemical compound according to claim 1, wherein $R_{3a}$ and $R_{3b}$ are each independently a hydrogen atom or an alkyl group.

10. A chemical compound according to claim 1, wherein $R_{3a}$ and $R_{3b}$ each are a hydrogen atom.

11. A chemical compound according to claim 1, wherein $R_{3a}$ and $R_{3b}$ each are an alkyl group.

12. A chemical compound according to claim 1, wherein $R_{3a}$ and $R_{3b}$ each are a ($C_1$-$C_6$) alkyl group.

13. A chemical compound according to claim 1, wherein $R_{3a}$ and $R_{3b}$ each are a methyl (—$CH_3$) or ethyl (—$CH_2$—$CH_3$) group.

14. A chemical compound according to claim 1, wherein the chemical compound is a compound having the formula: (VI):

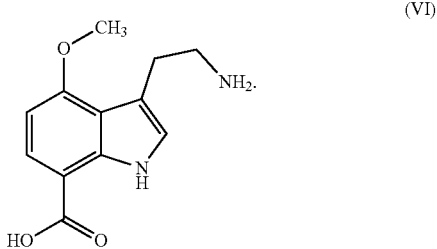 [SMILES: COc1ccc(C(=O)O)c2[nH]cc(CCN)c12]

(VI)

15. A chemical compound according to claim 1, wherein the compound is at least about 95% (w/w) pure.

16. A pharmaceutical drug formulation comprising an effective amount of a chemical compound according to claim 1, together with a pharmaceutically acceptable excipient, diluent, or carrier.

17. A pharmaceutical drug formulation comprising an effective amount of the chemical compound of claim 14 together with a pharmaceutically acceptable excipient, diluent, or carrier.

* * * * *